United States Patent [19]

Sum et al.

[11] Patent Number: 5,512,553

[45] Date of Patent: Apr. 30, 1996

[54] 7-(SUBSTITUTED)-8-(SUBSTITUTED)-9-(SUBSTITUTED AMINO)-6-DEMETHYL-6-DEOXYTETRACYCLINES

[75] Inventors: Phaik-Eng Sum, Pomona; Ving J. Lee, Monsey; Joseph J. Hlavka, Tuxedo Park, all of N.Y.; Raymond T. Testa, Cedar Grove, N.J.

[73] Assignee: American Cyanamid Company, Wayne, N.J.

[21] Appl. No.: 454,966

[22] Filed: May 31, 1995

Related U.S. Application Data

[62] Division of Ser. No. 214,992, Mar. 21, 1994, Pat. No. 5,430,162, which is a continuation of Ser. No. 928,598, Aug. 13, 1992.

[51] Int. Cl.⁶ .................................................. A61K 31/65
[52] U.S. Cl. .............................................................. 514/152
[58] Field of Search ...................................... 514/152

[56] References Cited

U.S. PATENT DOCUMENTS 5,430,162  7/1995  Sum et al. ............................... 552/205

*Primary Examiner*—Jerome D. Goldberg
*Attorney, Agent, or Firm*—T. S. Szatkowski

[57] ABSTRACT

The invention provides compounds of formula

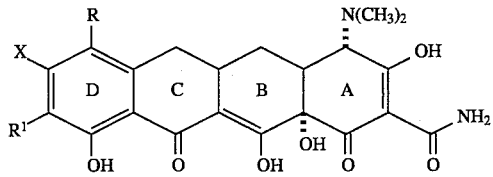

wherein X, R and R¹ are defined in the specification. These compounds are useful as antibiotic agents.

1 Claim, No Drawings

7-(SUBSTITUTED)-8-(SUBSTITUTED)-9-(SUBSTITUTED AMINO)-6-DEMETHYL-6-DEOXYTETRACYCLINES

This is a divisional of copending application(s) Ser. No. 08/214,992 filed on Mar. 21, 1994 U.S. Pat. No. 5,430,162 of Phaik-Eng Sum et al., for NOVEL 7-(SUBSTITUTED)-8-(SUBSTITUTED)-9-(SUBSTITUTED AMINO)-6-DEMETHYL DEOXYTETRACYCLINES which is a continuation of copending application Ser. No. 07/928,598 filed Aug. 13, 1992.

BACKGROUND OF THE INVENTION

1. Field of the Invention

The invention relates to novel [4S-(4alpha, 12aalpha)]-4-(dimethylamino)-7-(substituted)-8-(substituted)-9-(substituted)-1,4,4a,5,5a,6,11,12a-octahydro- 3,10,12,12a-tetrahydroxy-1,11-dioxo-2-naphthacenecarboxamides herein after called 7-(substituted)-8-(substituted)-9-(substituted)-6-demethyl- 6-deoxytetracyclines, which are useful as antibiotic agents and exhibit antibacterial activity against a wide spectrum of organisms including organisms which are resistant to tetracyclines.

The invention also relates to novel 7-(substituted)-S-(substituted)-9-(substituted)-6-demethyl- 6-deoxytetracycline intermediates useful for making the novel compounds of the present invention and to novel methods for producing the novel compounds and intermediate compounds.

SUMMARY OF THE INVENTION

This invention is concerned with novel 7-(substituted)-S-(substituted)-9-(substituted)-6-demethyl- 6-deoxytetracyclines, represented by formulas I and II, which have antibacterial activity; with method of treating infectious diseases in warm blooded animals employing these new compound; with methods of treating or controlling veterinary diseases; with pharmaceutical preparations containing these compounds; with novel intermediate compounds and processes for the production of these compounds. More particularly, this invention is concerned with compounds of formulas I and II which have enhanced in vitro and in vivo antibiotic activity against tetracycline resistant strains as well as a high level of activity against strains which are normally susceptible to tetracyclines.

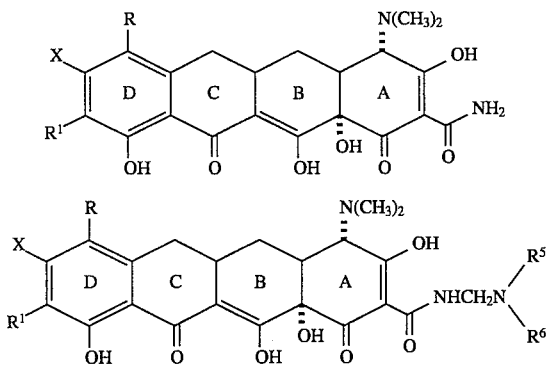

In formula I and II, X is selected from halogen or trifluoromethanesulfonyloxy; the halogen is selected from bromine, chlorine, fluorine or iodine; R and $R^1$ are the same or different and are selected from hydrogen; nitro; amino; halogen (selected from chlorine, bromine, fluorine or iodine); cyano; hydroxy; or $—NR^2R^3$;

and when R or $R^1=—NR^2R^3$ and $R^2=$ hydrogen, $R^3=$ methyl, ethyl, n-propyl, 1-methylethyl, n-butyl, 1-methylpropyl, 2-methylpropyl or 1,1-dimethylethyl; and when $R^2=$ methyl or ethyl, $R^3=$ methyl, ethyl, n-propyl, 1-methylethyl, n-butyl, 1-methylpropyl or 2-methylpropyl;
and when $R^2=$ n-propyl,
$R^3=$ n-propyl, 1-methylethyl, n-butyl, 1-methylpropyl or 2-methylpropyl;
and when $R^2=$1-methylethyl,
$R^3=$ n-butyl, 1-methylpropyl or 2-methylpropyl; and when $R^2=$n-butyl,
$R^3=$ n-butyl, 1-methylpropyl or 2-methylpropyl;
and when $R^2=$ 1-methylpropyl,
$R^3=$2-methylpropyl; and when R or $R^1=—NR^2R^3$ and $R^2=$ hydrogen,
$R^3$ is selected from $R^4(CH_2)_nCO—$ or $R^{4'}(CH_2)_nSO_2—$; and when $R^3= R^4(CH_2)_nCO—$ and n=0,
$R^4$ is selected from hydrogen; amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di($C_1$–$C_6$)alkylamino group selected from dimethylamino, diethylamino, methyl(ethyl)amino, ethyl(1-methylethyl)-amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo-[ 2.2.1]hept-2-yl, 7-azabicyclo [2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; carboxy($C_2$–$C_4$)alkylamino group selected from aminoacetic acid, α-aminopropionic acid, or α-aminobutyric acid and their optical isomers; (heterocyclo)amino group selected from 2- or 3-furyl, 2- or 3-thienyl, 2-, 3- or 4-pyridyl, 2- or 5-pyridazinyl, 2-pyrazinyl, or 2-(imidazolyl)amino and their substituted analogues (substitution selected from straight or branched ($C_1$–$C_6$)alkyl); ($C_6$–$C_{10}$)arylamino group selected from phenylamino or naphthylamino; substituted ($C_6$–$C_{10}$)arylamino group selected from 4-(acetamido)phenyl, 2-,3- or 4-halophenyl, 2-,3-, or 4-($C_1$–$C_4$)alkylphenyl, or 2-,3- or 4-carboxyphenylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl; α-hydroxy($C_1$–$C_3$)alkyl group selected from hydroxymethyl, α-hydroxyethyl,α-hydroxy-1-methylethyl or α-hydroxypropyl; α-mercapto($C_1$–$C_3$)alkyl group selected from mercaptomethyl, α-mercaptoethyl, α-mercapto-1-methylethyl or α-mercaptopropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

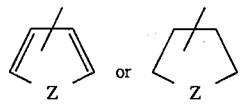

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

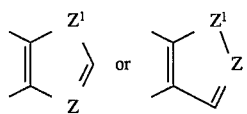

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

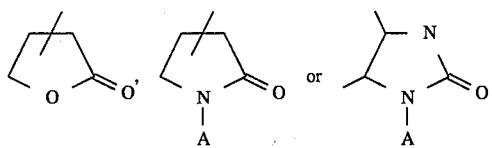

(A is selected from hydrogen; straight or branched ($C_1$–$C_4$) alkyl; $C_6$-aryl; substituted $C_6$-aryl (substitution selected from halo, ($C_1$–$C_4$)alkoxy, trihalo($C_1$–$C_3$)-alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxo-thiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

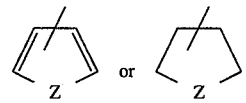

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

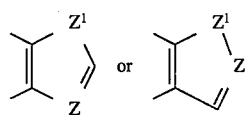

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

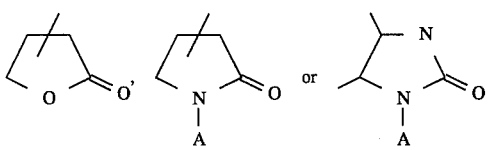

(A is selected from hydrogen; straight or branched ($C_1$–$C_4$) alkyl; $C_6$-aryl; substituted $C_6$-aryl (substitution selected from halo, (Cl–$C_4$) alkoxy, trihalo ($C_1$–$C_3$) alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; α-aminomethoxycarbonyl; halomethoxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

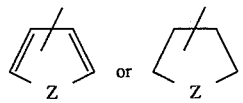

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethgyloxy; vinyloxy or substituted vinyloxy group (substitution selected from ($C_1$–$C_4$)alkyl, cyano, carboxy, or ($C_6$–$C_{10}$)aryl selected from phenyl, α-naphthyl or β-naphthyl); $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, 2-methylpropyl or 1,1-dimethylethyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)— alkyl [straight or branched], —NH, —NOB [B is selected from hydrogen or ($C_1$–$C_3$)alkyl], O or S; and when $R^3=R^4(CH_2)_nCO$— and n=1–4;

$R^4$ is selected from hydrogen; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted($C_6$–$C_{10}$)— aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group such as benzyl, 1-phenylethyl, 2-phenylethyl or phenylpropyl; acyloxy or haloacyloxy group, selected from acetyl, propionyl, chloroacetyl, trichloroacetyl, ($C_3$–$C_6$)cycloalkyl- carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, (heterocycle)carbonyl, the heterocycle selected from a five membered aromatic or saturated ring with one N, O, S or Se heteroatom optionally having a benzo or pyrido ring fused thereto:

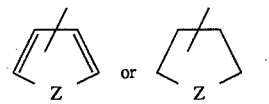

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

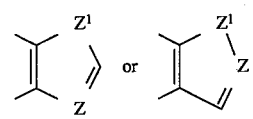

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

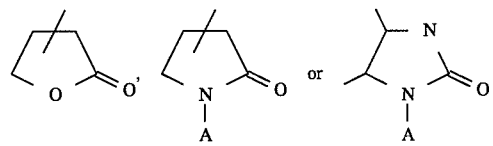

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1- piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy,n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di$(C_1-C_3)$alkylamino); $C_6$-arylsulfonyl group selected from phenylsulfonyl or substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

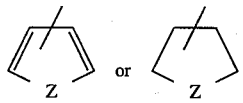

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

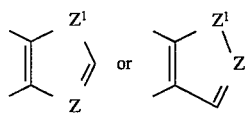

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

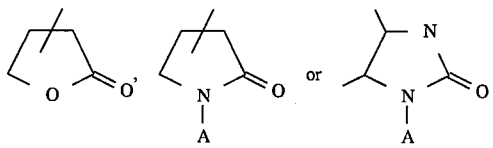

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-pipera- zinyl, 4-methyl-2,3-dioxo- 1-piperazinyl, 4-cyclopropyl-2-dioxo-1-piperazinyl, 2-dioxomorpholinyl or 2-dioxothiomorpholinyl; hydroxy group; mercapto group; α-hydroxy$(C_1-C_3)$alkyl group selected from hydroxy- methyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl, 3,4-difluorobenzoyl, $(C_1-C_4)$alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

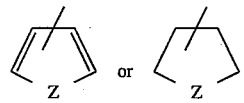

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl,benzofuranyl, tetrahydrothienyl, thienyl, benzothienyl or selenazolyl, or a five membered aromatic ring with two N, O, S or Se heteroatoms optionally having a benzo or pyrido ring fused thereto:

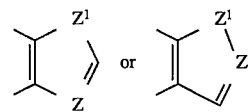

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

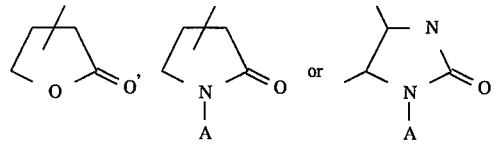

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxycarbonyl, allyloxycarbonyl or straight or branched butoxycarbonyl; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$ n=2–6, or —$(CH_2)_2W(CH2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$— $(CH_2)_2$— wherein W is selected from —N($C_1$–$C_3$)alkyl [straight or branched], —NH, —NOB [B is selected from hydrogen or ($C_1$–$C_3$)alkyl], O or S; and when $R^3$= $R^4(CH_2)_n$CO— and n= 2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$-$C_6$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct- 2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylpropyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1]hex-5-yl, 2-azabicyclo-[ 2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; carboxy($C_2$–$C_4$)alkylamino group selected from aminoacetic acid, α-aminopropionic acid, or α-aminobutyric acid and their optical isomers; (heterocyclo)amino group selected from 2- or 3-furyl, 2- or 3-thienyl, 2-, 3- or 4-pyridyl, 2- or 5-pyridazinyl, 2-pyrazinyl, or 2-(imidazolyl)amino and their substituted analogues (substitution selected from straight or branched ($C_1$–$C_6$)alkyl); ($C_6$–$C_{10}$)arylamino group selected from phenylamino or naphthylamino; substituted ($C_6$–$C_{10}$)arylamino group selected from 4-(acetamido)phenyl, 2-,3- or 4-halophenyl, 2-,3-, or 4-($C_1$–$C_4$)alkylphenyl, or 2-,3- or 4-carboxyphenylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino;

and when $R^3$=$R^{4'}(CH_2)_nSO_2$— and n=0,
$R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$-$C_8$)cycloalkylamino roup selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; (C₂–C₈)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo- 2.2.1]hept-2-yl, 7-azabicyclo[2.2.1] hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-(C₁–C₄)alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; (C₆–C₁₀)arylamino group selected from phenylamino or naphthylamino; (C₇–C₁₀)arylalkylamino group selected from benzyl, 2-phenylethyl, α-phenylethyl, (2-naphthyl)methyl, (1-naphthyl)methyl or phenylpropylamino; straight or branched (C₁–C₄)alkyl group selected from methyl, ethyl, n-propyl, 1-methylethyl, n-butyl, 1-methylpropyl, 2-methylpropyl or 1,1-dimethylethyl; (C₃–C₆)cycloalkyl group selected from cyclopropyl, cyclobutyl, cyclopentyl or cyclohexyl; substituted (C₃–C₆)cycloalkyl group (substitution selected from (C₁–C₃)alkyl, cyano, amino or (C₁–C₃)acyl); (C₆–C₁₀)aryl group selected from phenyl, α-naphthyl or β-naphthyl; substituted (C₆–C₁₀)aryl group (substitution selected from halo, (C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group such as benzyl, 1-phenylethyl, 2-phenylethyl or phenylpropyl; halo(C₁–C₃)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; a heterocycle group selected from a five membered aromatic or saturated ring with one N, O, S or Se heteroatom optionally having a benzo or pyrido ring fused thereto:

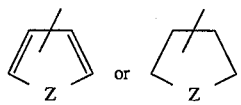

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

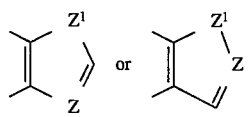

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

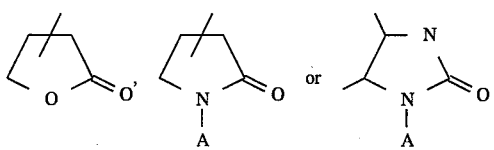

(A is selected from hydrogen; straight or branched (C₁–C₄)alkyl; C₆-aryl; substituted C₆-aryl (substitution selected from halo,(C₁–C₄)alkoxy, trihalo(C₁–C₃)alkyl, nitro, amino, cyano, (C₁–C₄)-alkoxycarbonyl, (C₁–C₃)alkylamino or carboxy); (C₇–C₉)-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C₁–C₃)alkylthio-pyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; $R^aR^b$amino(C₁–C₄)alkoxy group, wherein $R^aR^b$ is a straight or branched (C₁–C₄)alkyl selected from methyl, ethyl, n-propyl, 1-methylethyl, n-butyl, 1-methylpropyl, or 2-methylpropyl or $R^aR^b$ is (CH₂)ₙ n=2–6, or —(CH₂)₂W(CH₂)₂- wherein W is selected from —N(C₁–C₃)alkyl [straight or branched], —NH, —NOB [B is selected from hydrogen or (C₁–C₃)alkyl], O or S; or $R^aR^b$aminoxy group, wherein $R^aR^b$ is a straight or branched (C₁–C₄)alkyl selected from methyl, ethyl, n-propyl, 1-methylethyl, n-butyl, 1-methylpropyl, or 2-methylpropyl or $R^aR^b$ is (CH₂)ₙ, n=2–6, or —(CH₂)₂W— (CH₂)₂— wherein W is selected from —N(C₁–C₃)alkyl [straight or branched], —NH, —NOB [B is selected from hydrogen or (C₁–C₃)alkyl], O or S; and when $R^3=R^{4'}$(CH₂)ₙSO₂— and n=1–4, $R^{4'}$ is selected from hydrogen; straight or branched (C₁–C₄)alkyl group selected from methyl, ethyl, n-propyl, 1-methylethyl, n-butyl, 1-methylpropyl, 2-methylpropyl or 1,1-dimethylethyl; (C₁–C₄)carboxyalkyl group; (C₃–C₆)cycloalkyl group selected from cyclopropyl, cyclobutyl, cyclopentyl or cyclohexyl; substituted (C₃–C₆)cycloalkyl group (substitution selected from (C₁–C₃)alkyl, cyano, amino or (C₁–C₃)acyl); (C₆–C₁₀)aryl group selected from phenyl, α-naphthyl or β-naphthyl; substituted (C₆–C₁₀)aryl group (substitution selected from halo, (C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl; (C₁–C₄)alkoxy group such as allyloxy, methoxy, ethoxy, n-propoxy or tert-butoxy; C₆-aryloxy group selected from phenoxy or substituted phenoxy (substitution selected from halo, (C₁–C₃)alkyl, nitro, cyano, thiol, amino, carboxy, di(C₁–C₃)alkylamino); (C₇–C₁₀)aralkyloxy group such as benzyloxy, 1-phenylethyloxy or 2-phenylethyloxy; $R^aR^b$amino(C₁–C₄)alkoxy group, wherein $R^aR^b$ is a straight or branched (C₁–C₄)alkyl selected from methyl, ethyl, n-propyl, 1-methylethyl, n-butyl, 1-methylpropyl, or 2-methylpropyl or $R^aR^b$ is (CH₂)ₙ n=2–6, or —(CH₂)₂W(CH₂)₂— wherein W is selected from —N(C₁–C₃)-alkyl [straight or branched], —NH, —NOB [B is selected from hydrogen or (C₁–C₃)alkyl], O or S; or $R^aR^b$aminoxy group, wherein $R^aR^b$ is a straight or branched (C₁–C₄)alkyl selected from methyl, ethyl, n-propyl, 1-methylethyl, n-butyl, 1-methylpropyl, or 2-methylpropyl or $R^aR^b$ is $(CH_2)_n$ n=2–6, or —$(CH_2)_2W(CH_2)_2$— wherein W is selected from —$N(C_1$–$C_3)$-alkyl [straight or branched], —NH, —NOB [B is selected from hydrogen or $(C_1$–$C_3)$alkyl], O or S; $(C_1$–$C_3)$alkylthio group selected from methylthio, ethylthio or n-propylthio; $C_6$-arylthio group selected from phenylthio or substituted phenylthio (substitution selected from halo, $(C_1$–$C_3)$alkyl, nitro, cyano, thiol, amino, carboxy, di$(C_1$–$C_3)$alkylamino); $(C_7$–$C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

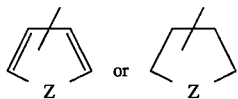

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

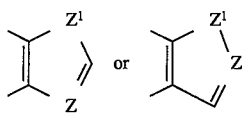

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

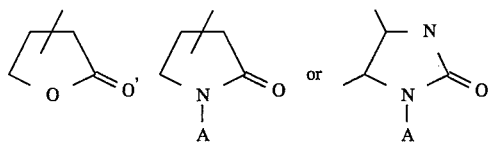

(A is selected from hydrogen; straight or branched $(C_1$–$C_4)$alkyl; $C_6$-aryl; substituted $C_6$-aryl (substitution selected from halo,$(C_1$–$C_4)$alkoxy, trihalo$(C_1$–$C_3)$alkyl, nitro, amino, cyano, $(C_1$–$C_4)$-alkoxycarbonyl, $(C_1$–$C_3)$alkylamino or carboxy); $(C_7$–$C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1$–$C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; hydroxy group; mercapto group; amino; hydroxyamino; straight or branched mono$(C_1$–$C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3$–$C_8)$cycloalkylamino group selected from cyclopropyl, trans-1,2-dimethylcyclopropyl, cis-1,2-dimethylcyclopropyl, trans- 2,3-dimethylcyclopropyl, cis-2,3-dimethylcyclopropyl, cyclobutyl, trans-2,3-dimethylcyclobutyl, cis- 2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1$–$C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1$–$C_6)$alkoxyamino group selected from methoxy, ethoxy, propoxy, butoxy, pentoxy or hexoxyamino; $(C_3$–$C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[2.2.1]oct-2-yloxyamino and where appropriate their diastereomers and enantiomers; $(C_7$–$C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2$–$C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo-[ 2.2.1]hept-2-yl, 7-azabicyclo [2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1$–$C_4)$alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; $(C_6$–$C_{10})$arylamino group selected from phenylamino or naphthylamino; $(C_7$–$C_{10})$arylalkylamino group selected from benzyl, 2-phenylethyl, α-phenylethyl, (2-naphthyl)methyl, (1-naphthyl)methyl or phenylpropylamino; halo$(C_1$–$C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; acyl or haloacyl group selected from acetyl, propionyl, chloroacetyl, trifluoroacetyl, $(C_3$–$C_6)$cycloalkylcarbonyl, $(C_6$–$C_{10})$aroyl selected from benzoyl or naphthoyl, halo substituted $(C_6$–$C_{10})$aroyl such as pentafluorobenzoyl, 4-chlorobenzoyl, 3-bromobenzoyl or 3,4-difluorobenzoyl, $(C_1$–$C_4)$alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

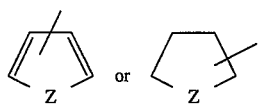

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

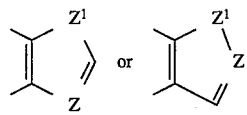

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

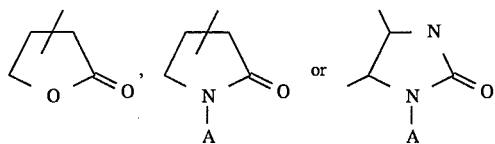

(A is selected from hydrogen; straight or branched $(C_1-C_4)$alkyl; $C_6$-aryl; substituted $C_6$-aryl (substitution selected from halo, $(C_1-C_4)$ alkoxy, trihalo $(C_1-C_3)$ alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxycarbonyl group selected from methoxycarbonyl, ethoxycarbonyl, straight or branched propoxycarbonyl, allyloxycarbonyl or straight or branched butoxycarbonyl; $R^5$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

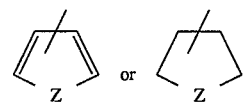

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

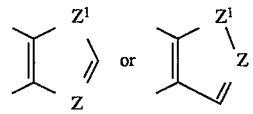

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

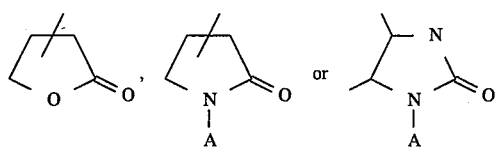

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$ alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)_n COOR^7$ where n=0–4 and $R^7$ is selected from hydrogen; straight or branched $(C_1-C_3)$alkyl group selected from methyl, ethyl, n-propyl or 1-methylethyl; or $(C_6-C_{10})$aryl group selected from phenyl, α-naphthyl, β-naphthyl; $R^6$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

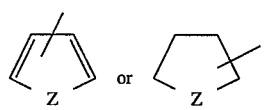

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

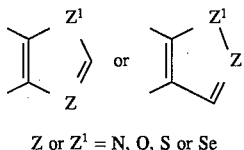

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

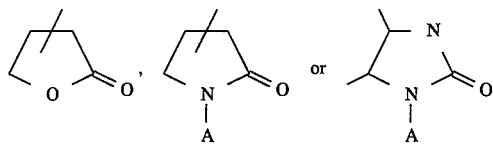

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-pipera- zinyl, 4-methyl-2,3-dioxo-1-piperazinyl, 4-cyclopropyl- 2-dioxo-1-piperazinyl, 2-dioxomorpholinyl, 2-dioxothiomorpholinyl; or —$(CH_2)_n$COOR⁷' where n=0–4 and R⁷' is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that R⁵ and R⁶ cannot both be hydrogen; or R⁵ and R⁶ taken together are —$(CH_2)_2$W$(CH_2)_2$—, wherein W is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula I and II in which X is selected from halogen or trifluoromethanesulfonyloxy; the halogen is selected from bromine, chlorine, fluorine or iodine; R and R¹ are the same or different and are selected from hydrogen; nitro; amino; halogen (selected from chlorine, bromine, fluorine or iodine); cyano; hydroxy or —NR²R³;
and when R or R¹=—NR²R³ and R²=hydrogen, R³=methyl, ethyl, n-propyl, 1-methylethyl, n-butyl, 1-methylpropyl, 2-methylpropyl or 1,1-dimethylethyl; and when R²=methyl or ethyl, R³=methyl, ethyl, n-propyl, 1-methylethyl, n-butyl, 1-methylpropyl or 2-methylpropyl;
and when R or R¹=—NR²R³ and R²=hydrogen, R³ is selected from R⁴$(CH_2)_n$CO— or R⁴'$(CH_2)_n$SO$_2$—; and when R³=R⁴$(CH_2)_n$CO— and n=0, R⁴ is selected from hydrogen; amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo [2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept- 2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo-[ 2.2.1]hept-2-yl, 7-azabicyclo [2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; carboxy$(C_2-C_4)$alkylamino group selected from aminoacetic acid, α-aminopropionic acid, or α-aminobutyric acid and their optical isomers; (heterocyclo)amino group selected from 2- or 3-furyl, 2- or 3-thienyl, 2-, 3- or 4-pyridyl, 2- or 5-pyridazinyl, 2-pyrazinyl, or 2-(imidazolyl)amino and their substituted analogues (substitution selected from straight or branched $(C_1-C_6)$alkyl); $(C_6-C_{10})$arylamino group selected from phenylamino or naphthylamino; substituted $(C_6-C_{10})$arylamino group selected from 4-(acetamido)phenyl, 2-,3- or 4-halophenyl, 2-,3-, or 4-$(C_1-C_4)$alkylphenyl, or 2-,3- or 4-carboxyphenylamino; $(C_7-C_{10})$arylalkylamino group selected from benzyl, 2-phenylethyl, α-phenylethyl, (2-naphthyl)methyl, (1-naphthyl)methyl or phenylpropylamino; straight or branched $(C_1-C_3)$alkyl group selected from methyl, ethyl, n-propyl or 1-methylethyl; $(C_3-C_6)$cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); α-hydroxy($C_1$–$C_3$)alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

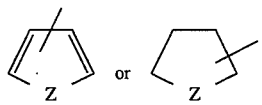

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

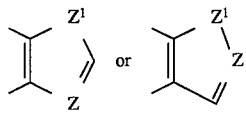

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

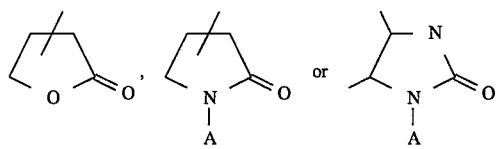

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methyltoluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

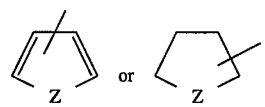

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

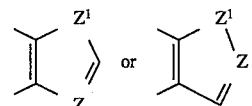

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

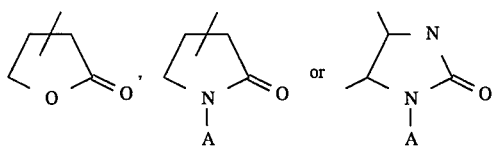

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; α-aminomethoxycarbonyl; halomethoxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

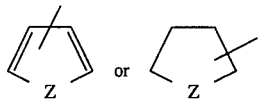

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; vinyloxy or substituted vinyloxy group (substitution selected from ($C_1$–$C_4$)alkyl, cyano, carboxy, or ($C_6$–$C_{10}$)aryl selected from phenyl, α-naphthyl or β-naphthyl); $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$ n=2–6, or —$(CH_2)_2^W$ $(CH_2)_2$- wherein W is selected from —N($C_1$–$C_3$)alkyl [straight or branched], —NH, —NOB [B is selected from hydrogen or ($C_1$–$C_3$) alkyl ], O or S; and when $R^3=R^4$ $(CH_2)_nCO$— and n=1–4, $R^4$ is selected from hydrogen; ($C_1$–$C_3$)alkyl group selected from methyl, ethyl, n-propyl or 1-methylethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)-alkyl, nitro, amino, cyano, ($C_1$–$C_4$)alkoxycarbonyl, ($C_1$–$C_3$)alkylamino or carboxy); acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

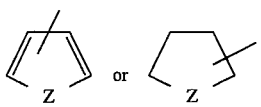

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

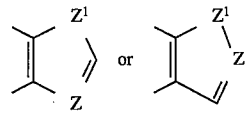

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

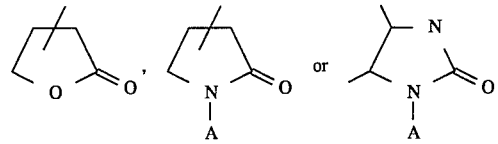

(A is selected from hydrogen; straight or branched ($C_1$–$C_4$) alkyl; $C_6$-aryl; substituted $C_6$-aryl (substitution selected from halo, ($C_1$–$C_4$) alkoxy, trihalo ($C_1$–$C_3$) alkyl, nitro, amino, cyano, ($C_1$–$C_4$) -alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy, n-butoxy or tert-butoxy; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$ n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$ n=2–6, or —$(CH_2)_2W$—$(CH_2)_2$- wherein W is selected from —N($C_1$–$C_3$)alkyl [straight or branched], —NH, —NOB [B is selected from hydrogen or ($C_1$–$C_3$)alkyl], O or S; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di-($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

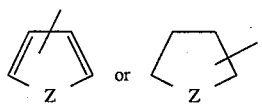

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O,S or Se heteroatoms optionally having a benzo or pyrido ring fused thereto:

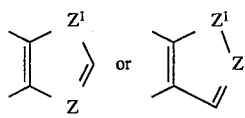

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

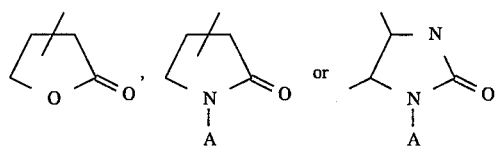

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy$(C_1-C_3)$alkyl group selected from hydroxymethyl, α-hydroxyethyl, α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl,or 4-(1-methylethyl)-benzoyl, or (heterocycle)carbonyl, the heterocycle selected from a five membered aromatic or saturated ring with one N, O, S or Se heteroatom optionally having a benzo or pyrido ring fused thereto:

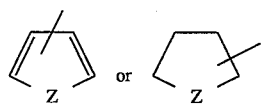

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

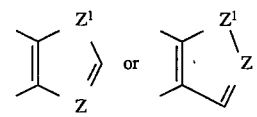

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

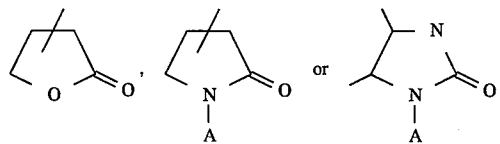

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxo-thiomorpholinyl;

and when $R^3=R^4(CH_2)_nCO-$ and n=2-4, $R^4$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl- 1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yl-oxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethyl-pyrrolidinyl, trans-3,4-dimethylpyrrolidinyl, 2-azabicyclo[ 2.1.1]hex-2-yl, 5-azabicyclo[2.1.1]hex- 5-yl, 2-azabicyclo[2.2.1]hept-2-yl, 7-azabicyclo-[ 2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; carboxy($C_2$–$C_4$)alkylamino group selected from aminoacetic acid, α-aminopropionic acid, or α-aminobutyric acid and their optical isomers; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino;

and when $R^3 = R^{4'}(CH_2)_nSO_2$— and n=0, $R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept- 2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl,.piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept- 2-yl, 7-azabicyclo[2.2.1]hept-7-yl, or 2-azabicyclo-[ 2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

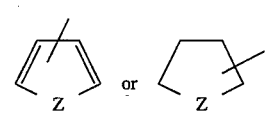

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

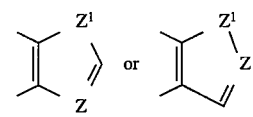

-continued

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

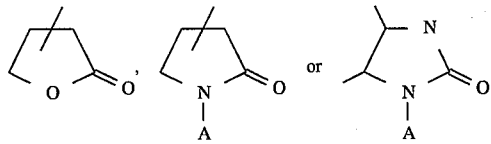

(A is selected from hydrogen; straight or branched $(C_1$–$C_4)$alkyl; $C_6$-aryl; substituted $C_6$-aryl (substitution selected from halo,$(C_1$–$C_4)$alkoxy, trihalo$(C_1$–$C_3)$alkyl, nitro, amino, cyano, $(C_1$–$C_4)$-alkoxycarbonyl, $(C_1$–$C_3)$alkylamino or carboxy); $(C_7$–$C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl;
and when $R^3$=$R^{4'}(CH_2)_nSO_2$— and n=1–4, $R^{4'}$ is selected from hydrogen; amino; hydroxyamino; straight or branched mono$(C_1$–$C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3$–$C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1$–$C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1$–$C_6)$alkoxyamino group selected from methoxy, ethoxy, propoxy, butoxy, pentoxy or hexoxyamino; $(C_3$–$C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers;
$(C_7$–$C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2$–$C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo-[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl; 4-hydroxypiperazinyl, 4-$(C_1$–$C_4)$-alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; $(C_6$–$C_{10})$arylamino group selected from phenylamino or naphthylamino; $(C_7$–$C_{10})$arylalkylamino group selected from benzyl, 2-phenylethyl, α-phenylethoxy, (2-naphthyl)methyl, (1-naphthyl)methyl or phenylpropylamino; straight or branched $(C_1$–$C_3)$alkyl group selected from methyl, ethyl, n-propyl or 1-methylethyl; $(C_6$–$C_{10})$aryl group selected from phenyl, α-naphthyl or β-naphthyl; substituted $(C_6$–$C_{10})$aryl group (substitution selected from halo, $(C_1$–$C_4)$alkoxy, trihalo$(C_1$–$C_3)$alkyl, nitro, amino, cyano, $(C_1$–$C_4)$alkoxycarbonyl, $(C_1$–$C_3)$alkylamino or carboxy); $(C_1$–$C_4)$alkoxy group such as allyloxy, methoxy, ethoxy, n-propoxy, n-butoxy, iso-butoxy or tert-butoxy; $C_6$-aryloxy group selected from phenoxy or substituted phenoxy (substitution selected from halo, $(C_1$–$C_4)$alkyl, nitro cyano, thiol, amino, carboxy, di$(C_1$–$C_3)$alkylamino; $(C_7$–$C_{10})$aralkyloxy group such as benzyloxy, 1-phenylethyloxy or 2-phenylethyloxy; $(C_1$–$C_4)$carboxyalkyl group; $R^5$ is selected from hydrogen; straight or branched $(C_1$–$C_3)$alkyl group selected from methyl, ethyl, n-propyl or 1-methylethyl; $(C_6$–$C_{10})$aryl group selected from phenyl, α-naphthyl or β-naphthyl; $(C_7$–$C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

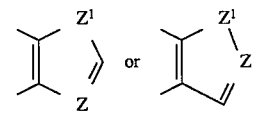

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

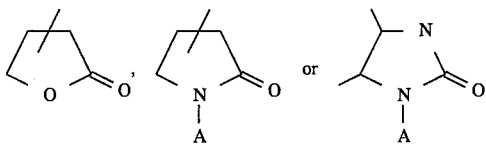

(A is selected from hydrogen; straight or branched (C₁–C₄)alkyl; C₆-aryl; substituted C₆-aryl (substitution selected from halo,(C₁–C₄)alkoxy, trihalo(C₁–C₃)alkyl, nitro, amino, cyano, (C₁–C₄)-alkoxycarbonyl, (C₁–C₃)alkylamino or carboxy); (C₇–C₉)-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl or pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —(CH₂)ₙCOOR⁷ where n=0–4 and R⁷ is selected from hydrogen; straight or branched (C₁–C₃)alkyl group selected from methyl, ethyl, n-propyl or 1-methylethyl; or (C₆–C₁₀)aryl group selected from phenyl, α-naphthyl or β-naphthyl; R⁶ is selected from hydrogen; straight or branched (C₁–C₃)alkyl group selected from methyl, ethyl, n-propyl or 1-methylethyl; (C₆–C₁₀)aryl group selected from phenyl, α-naphthyl or β-naphthyl; (C₇–C₉)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

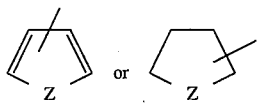

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

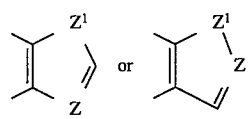

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

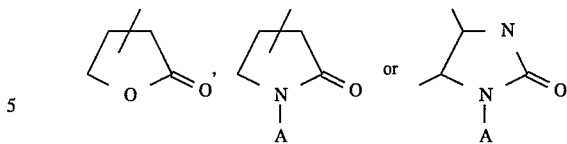

(A is selected from hydrogen; straight or branched (C₁–C₄)alkyl; C₆-aryl; substituted C₆-aryl (substitution selected from halo,(C₁–C₄)alkoxy, trihalo(C₁–C₃)-alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothio-ₙCOOR⁷ where n=0–4 and R⁷ is morpholinyl; or (CH₂) selected from hydrogen; straight or branched (C₁–C₃)-alkyl selected from methyl, ethyl, n-propyl or 1-methylethyl; or (C₆–C₁₀)aryl selected from phenyl, α-naphthyl or β-naphthyl; with the proviso that R⁵ and R⁶ cannot both be hydrogen;
or R⁵ and R⁶ taken together are —(CH₂)₂W(CH₂)₂—, wherein W is selected from (CH₂)ₙ and n=0–1, —NH, —N(C₁–C₃)alkyl [straight or branched], —N(C₁–C₄)alkoxy, oxygen, sulfur or substituted congeners selected from (L or D)proline, ethyl(L or D)prolinate, morpholine, pyrrolidine or piperidine; and the pharmacologically acceptable organic and inorganic salts-or metal complexes.

Particularly preferred compounds are compounds according to the above formula I and II in which X is selected from halogen or trifluoromethanesulfonyloxy; the halogen is selected from bromine, chlorine, fluorine or iodine;
R and R¹ are the same or different and are selected from hydrogen; nitro; amino; halogen (selected from chlorine, bromine, fluorine or iodine); cyano; hydroxy; or —NR²R³;
and when R or R¹=—NR²R³ and R²=hydrogen, R³=methyl, ethyl, n-propyl, 1-methylethyl, n-butyl, 1-methylpropyl, 2-methylpropyl or 1,1-dimethylethyl;
and when R²=methyl or ethyl, R³=methyl, ethyl, n-propyl, 1-methylethyl, n-butyl, 1-methylpropyl or 2-methylpropyl;
and when R or R¹=—NR²R³ and R²=hydrogen, R³ is selected from R⁴(CH₂)ₙCO— or R⁴'(CH₂)ₙSO₂—;
and when R³=R⁴(CH₂)ₙCO— and n=0, R⁴ is selected from hydrogen; amino; hydroxyamino; straight or branched mono(C₁–C₆)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C₃–C₈)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di-($C_1$–$C_6$)-alkylamino group selected from dimethylamino, diethylamino, methyl(ethyl)amino, ethyl(1-methylethyl)-amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethyl-cyclobutoxy, cis-2,3-dimethylcyclobutoxy, cyclopentoxy, cyclohexoxy, cycloheptyloxy, cyclooctoxy, bicyclo-[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethyl-pyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]-hept- 7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)—alkoxypiperazinyl, thiamorpholinyl, tetrahydro-1,2-oxazinyl, isoxazolidinyl, pyrazolidinyl, 2-methylpyrazolidinyl, 2,5-diazabicyclo[ 2.2.2]hept-2-yl, or 2,5-diaza-5-methylbicyclo-[ 2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; (heterocyclo)amino group selected from 2- or 3-furyl, 2- or 3-thienyl, 2-, 3- or 4-pyridyl, 2-or 5-pyridazinyl, 2-pyrazinyl, or 2-(imidazolyl)amino and their substituted analogues (substitution selected from straight or branched ($C_1$–$C_6$)alkyl); ($C_6$–$C_{10}$)aryl-amino group selected from phenylamino or naphthylamino; substituted ($C_6$–$C_{10}$)arylamino group selected from 4-(acetamido)phenyl, 2-,3- or 4-halophenyl, 2-,3-, or 4-($C_1$–$C_4$)alkylphenyl, or 2-,3- or 4-carboxyphenylamino; ($C_7$–$C_{10}$)arylalkylamino group selected from benzyl, 2-phenylethyl, α-phenylethyl, (2-naphthyl)-methyl, (1-naphthyl)methyl or phenylpropylamino; straight or branched ($C_1$–$C_3$)alkyl group selected from methyl, ethyl, n-propyl or 1-methylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$) alkoxycarbonyl, ($C_1$–$C_3$) alkylamino or carboxy); α-hydroxy ($C_1$–$C_3$ ) alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered ring or saturated ring with one N, O, S or Se heteroatom optionally having a benzo or pyrido ring fused thereto:

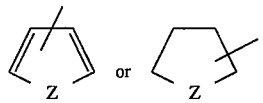

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

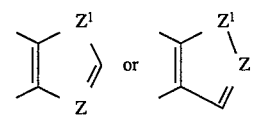

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

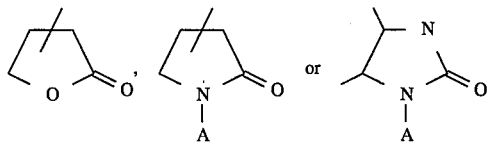

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)-alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl )

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methylbenzoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

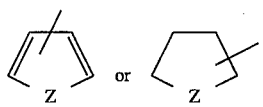

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

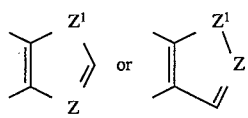

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

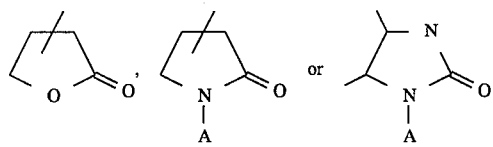

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-alkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxycarbonyl group selected from methoxycarbonyl, ethoxycarbonyl, straight or branched propoxylcarbonyl, straight or branched butoxycarbonyl or allyloxycarbonyl; α-aminomethoxycarbonyl; halomethoxycarbonyl; vinyl or substituted vinyl group [substitution selected from $(C_1-C_3)$alkyl group, halogen, $(C_6-C_{10})$aryl group selected from phenyl, α-naphthyl, β-naphthyl, substituted $(C_6-C_{10})$aryl group (substitution selected from halo, $(C_1-C_4)$alkoxy, $(C_1-C_4)$alkoxycarbonyl, $(C_1-C_3)$alkylamino or carboxy), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

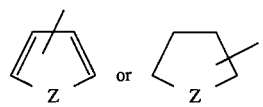

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$-alkyl); $(C_7-C_{10})$aralkyloxy group such as benzyloxy, 1-phenylethyloxy or 2-phenylethyloxy; and when $R^3=R^4(CH_2)_nCO-$ and $n=1-4$, $R^4$ is selected from hydrogen; $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

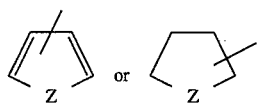

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

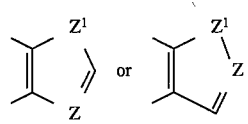

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

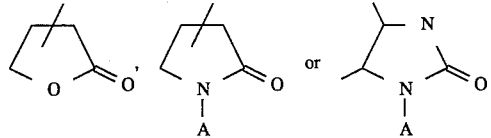

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$-alkyl, nitro, amino, cyano, $(C_1-C_4)$alkoxycarbonyl, $(C_1-C_3)$alkylamino or carboxy); $(C_7-C_9)$alkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di-$(C_1-C_3)$alkylamino); $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di-$(C_1-C_3)$alkylamino); $C_6$-arylsulfonyl group selected from phenylsulfonyl or substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); a heterocycle group selected from a five membered aromatic or saturated ring one N, O, S or Se heteroatom optionally having a benzo or pyrido ring fused thereto:

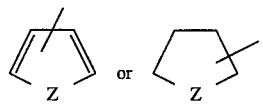

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

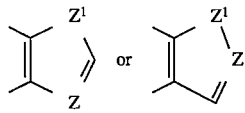

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

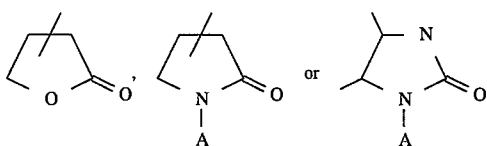

(A is selected from hydrogen; straight or branched $(C_1-C_4)$alkyl; $C_6$-aryl; substituted $C_6$-aryl (substitution selected from halo, $(C_1-C_4)$ alkoxy, trihalo $(C_1-C_3)$-alkyl, nitro, amino, cyano, $(C_1-C_4)$ alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; hydroxy group; α-hydroxy$(C_1-C_3)$alkyl group selected from hydroxymethyl, α-hydroxyethyl, α-hydroxy-1-methylethyl or α-hydroxypropyl; halo$(C_1-C_3)$alkyl group such as bromomethyl, fluoromethyl, difluoromethyl, trifluoroethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$-aroyl selected from benzoyl or naphthoyl, halo substituted $(C_6-C_{10})$aroyl such as pentafluorobenzoyl, 4-chlorobenzoyl, 3-bromophenylcarbonyl or 3,4-difluorobenzoyl, $(C_1-C_4)$alkylbenzoyl such as from 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

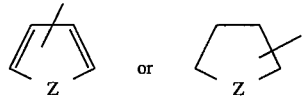

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

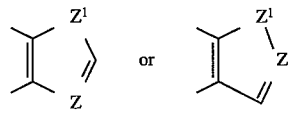

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

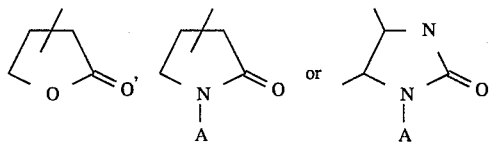

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl- 2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; and when $R^3=R^{4'}(CH_2)_nCO-$ and $n=2-4$, $R^4$ is selected from amino; hydroxyamino; straight or branched mono($C_1-C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl- 1-ethylpropylamino and where appropriate their diastereomers and enantiomers; ($C_3-C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1-C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1-C_6$)alkoxyamino group selected from methoxy, ethoxy, propoxy, butoxy, pentoxy or hexoxyamino; ($C_3-C_8$)cycloalkoxyamino group selected from cyclopropoxy, trans- 1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo-[2.2.1]hept-2-yloxy, or bicyclo[2.2.1]oct-2-yloxyamino and where appropriate their diastereomers and enantiomers; ($C_7-C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2-C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[ 2.1.1] hex-5-yl, 2-azabicyclo[2.2.1]hept-2-yl, 7-azabicyclo[2.2.1] hept-7-yl, or 2-azabicyclo[ 2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1-C_4$)alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; ($C_6-C_{10}$)arylamino group selected from phenylamino or naphthylamino; ($C_7-C_{10}$)arylalkylamino group selected from benzyl, 2-phenylethyl, α-phenylethyl, (2-naphthyl)methyl, (1-naphthyl)methyl or phenylpropylamino; ($C_1-C_4$)alkoxycarbonylamino group selected from tert-butoxycarbonylamino, allyloxycarbonylamino, methoxycarbonylamino, ethoxycarbonylamino or propoxycarbonylamino; and when $R^3 R^{4'} =(CH_2)_nSO_2-$ and $n=0$, $R^{4'}$ is selected from amino; hydroxyamino; straight or branched mono($C_1-C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3-C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2, 3-dimethylcyclobutyl, cis-2,3-dimethylcyclobutyl, cyclopentyl, cyclohexyl, cycloheptyl, cyclooctyl, bicyclo [2.2.1]hept-2-yl, or bicyclo[2.2.2]oct-2-ylamino and where appropriate their diastereomers and enantiomers; straight or branched chain di-($C_1-C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1-C_6$)alkoxyamino group selected from methoxy, ethoxy, propoxy, butoxy, pentoxy or hexoxyamino; ($C_3-C_8$)cycloalkoxyamino group selected from cyclopropoxy, trans-1,2-dimethylcyclopropoxy, cis-1, 2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[2.2.1]oct-2-yloxyamino and where appropriate their diastereomers and enantiomers; ($C_7-C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2-C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo-[2.2.1]hept-2-yl, 7-azabicyclo[ 2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1-C_4$)alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; ($C_6-C_{10}$)arylamino group selected from phenylamino or naphthylamino; ($C_7-C_{10}$)arylalkylamino group selected from benzyl, 2-phenylethyl, α-phenylethyl, (2-naphthyl)methyl, (1-naphthyl)methyl or phenylpropylamino; straight or branched ($C_1-C_3$)alkyl group selected from methyl, ethyl, n-propyl or 1-methylethyl; ($C_6-C_{10}$)aryl group selected from phenyl, α-naphthyl or β-naphthyl; substituted ($C_6-C_{10}$)aryl group (substitution selected from halo, ($C_1-C4$)alkoxy, trihalo($C_1-C_3$)alkyl, nitro, amino, cyano, ($C_1-C_4$)alkoxycarbonyl, ($C_1-C_3$)alkylamino or carboxy); a heterocycle group selected from a five membered aromatic or saturated ring with one N, O, S or Se heteroatom optionally having a benzo or pyrido ring fused thereto:

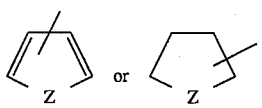

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl; and when $R^3 = R^{4'}(CH_2)_nSO_2$— and n=1–4, $R^{4'}$ is selected from hydrogen; amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo-[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_3$)alkyl group selected from methyl, ethyl, n-propyl or 1-methylethyl; $R^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; or —$(CH_2)_n$COOR$^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl or β-naphthyl; $R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; or $(CH_2)_n$COOR$^{7'}$ where n=0–4 and $R^{7'}$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^5$ and $R^6$ cannot both be hydrogen; or $R^5$ and $R^6$ taken together are —$(CH_2)_2W(CH_2)_2$—, wherein W is selected from $(CH_2)_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Most particularly preferred compounds are compounds according to the above formula I and II in which X is selected from halogen or trifluoromethanesulfonyloxy; the halogen is selected from bromine, chlorine, fluorine or iodine;

R and $R^1$ are the same or different and are selected from hydrogen; nitro; amino; halogen (selected from chlorine, bromine, fluorine or iodine); cyano; hydroxy; or —NR$^2$R$^3$;

and when R or $R^1$=—NR$^2$R$^3$ and $R^2$= hydrogen, $R^3$= methyl, ethyl, n-propyl, 1-methylethyl, n-butyl, 1-methylpropyl, 2-methylpropyl or 1,1-dimethylethyl; and when $R^2$= methyl or ethyl, $R^3$= methyl, ethyl, n-propyl, 1-methylethyl, n-butyl, 1-methylpropyl or 2-methylpropyl; and when R or $R^1$=—NR$^2$R$^3$ and $R^2$= hydrogen, $R^3$ selected from $R^4(CH_2)_n$CO— or $R^{4'}(CH_2)_n$SO$_2$—; and when $R^3$= $R^4(CH_2)_n$CO— and n=0, $R^4$ is selected from hydrogen; amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1]hex-5-yl, 2-azabicyclo-[ 2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_2$)alkyl group selected from methyl or ethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, nitro, amino); α-hydroxy($C_1$–$C_3$)alkyl group selected from hydroxymethyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

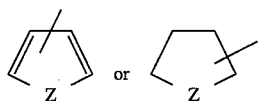

Z = N, O, S or Se such as indolyl, 2-pyrrolidinyl, 3-pyrrolidinyl, 2-pyrrolinyl, tetrahydrofuranyl, furanyl, benzofuranyl, tetrahydrothienyl or thienyl, or a five membered aromatic ring with two N, O, S or Se heteroatoms optionally having a benzo or pyrido ring fused thereto:

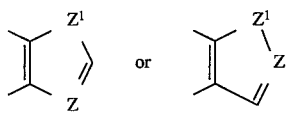

Z or $Z^1$ = N, O, S or Se such as imidazolyl, pyrazolyl, benzimidazolyl, indazolyl, thiazolyl or benzothiazolyl; ($C_1$–$C_4$)alkoxycarbonyl group selected from methoxycarbonyl, ethoxycarbonyl, straight or branched propoxycarbonyl, straight or branched butoxycarbonyl or allyloxycarbonyl; α-aminomethoxycarbonyl; halomethoxycarbonyl; vinyl or substituted vinyl group [substitution selected from ($C_1$–$C_3$)alkyl group, ($C_6$–$C_{10}$)aryl group selected from phenyl, α-naphthyl, β-naphthyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl); ($C_7$–$C_{10}$)aralkyloxy group such as benzyloxy, 1-phenylethyloxy or 2-phenylethyloxy; and when $R^3$= $R^4(CH_2)_nCO$— and n=1–4, $R^4$ is selected from hydrogen; ($C_1$–$C_2$)alkyl group selected from methyl or ethyl; ($C_6$–$C_{10}$)aryl group selected from phenyl, α-naphthyl or β-naphthyl; substituted($C_6$–$C_{10}$)aryl group (substitution selected from halo, ($C_1$–$C_4$)alkoxy, trihalo($C_1$–$C_3$)alkyl); acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N heteroatom optionally having a benzo or pyrido ring fused thereto:

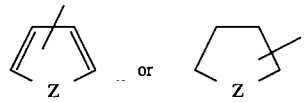

Z = N, O, S or Se such as tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

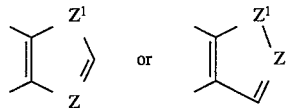

Z or $Z^1$ = N, O, S or Se such as pyrazolyl, benzimidazolyl, benzoxazolyl, indazolyl, thiazolyl-or benzothiazolyl, or a six membered aromatic ring with one or two N heteroatoms such as pyridyl or pyridazinyl; ($C_1$–$C_4$)alkoxy group such as allyloxy, methoxy, ethoxy, n-propoxy, n-butoxy or tert-butoxy; α-hydroxy($C_1$–$C_3$)alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; and when $R^3$=$R^4(CH_2)_nCO$— and n=2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[ 2.1.1]hex-2-yl, 5-azabicyclo[2.1.1]hex-5-yl, 2-azabicyclo[2.2.1]hept-2-yl, 7-azabicyclo[2.2.1] hept- 7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when $R^3$=$R^{4'}(CH_2)_nSO_2$— and n=0, $R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl- 1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex- 2-yl, 5-azabicyclo[2.1.1]hex-5-yl, 2-azabicyclo-[ 2.2.1]hept-2-yl, 7-azabicyclo[ 2.2.1] hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_2$)alkyl group selected from methyl or ethyl; ($C_6$–$C_{10}$)aryl group selected from phenyl, α-naphthyl or β-naphthyl; and when $R^3$= $R^{4'}(CH_2)_nSO_2$— and n=1–4, $R^{4'}$ is selected from hydrogen; straight or branched ($C_1$–$C_2$)alkyl group selected from methyl or ethyl; $R^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl; or —$(CH_2)_nCOOR^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, β-naphthyl; $R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl; or —$(CH_2)_nCOOR^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, β-naphthyl; with the proviso that $R^5$ and $R^6$ cannot both be hydrogen; or $R^5$ and $R^6$ taken together are —$(CH_2)_2W(CH_2)_2$—, wherein W is selected from $(CH_2)_n$ and n=0–1, —NH, —N($C_1$–$C_3$)alkyl [straight or branched], —N($C_1$–$C_4$)alkoxyl, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compounds according to the above formula I and II in which X is selected from halogen or trifluoromethanesulfonyloxy; the halogen is selected from bromine, chlorine, or fluorine; R and $R^1$ are the same or different and are selected from hydrogen; amino; halogen (selected from chlorine, bromine, fluorine or iodine); or —NR²R³; and when R or R¹=—NR²R³ and R²= methyl or ethyl; R³= methyl or ethyl, and when R or R¹=—NR²R³ and R²= hydrogen, R³ is selected from R4(CH₂)ₙCO— or R⁴'(CH₂)ₙSO₂—; and when R³= R⁴(CH₂)ₙCO— and n=0, R⁴ is selected from hydrogen; straight or branched (C₁–C₂)alkyl group selected from methyl or ethyl; a heterocycle group selected from a five membered aromatic or saturated ring with one N, O, or S heteroatom optionally having a benzo or pyrido ring fused thereto:

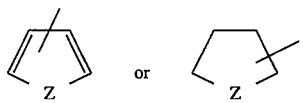

Z = N, O, or S such as furanyl or thienyl, or a five membered aromatic ring with two N, O or S heteroatoms optionally having a benzo or pyrido ring fused thereto:

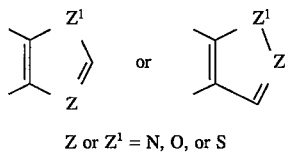

Z or Z¹ = N, O, or S such as pyrazolyl, benzimidazolyl or thiazolyl; (C₁–C₄)alkoxy group such as allyloxy, methoxy, ethoxy, n-propoxy, n-butoxy or tert-butoxy; C₆-aryloxy group selected from phenoxy or substituted phenoxy (substitution selected from halo, (C₁–C₄)alkyl); (C₇–C₁₀)aralkyloxy group such as benzyloxy, 1-phenylethyloxy or 2-phenylethyloxy; α-aminomethoxycarbonyl; or halomethoxycarbonyl; and when R³= R⁴(CH₂)ₙCO— and n=1–4, R⁴ is selected from hydrogen; (C₁–C₂)alkyl group selected from methyl or ethyl; (C₆–C₁₀)aryl group selected from phenyl, α-naphthyl or β-naphthyl; and when R³=R⁴'(CH₂)ₙSO₂— and n= 0, R⁴' is selected from straight or branched (C₁–C₂)alkyl group selected from methyl or ethyl; (C₆–C₁₀)aryl group selected from phenyl, α-naphthyl or β-naphthyl; R⁵ is selected from hydrogen; straight or branched (C₁–C₃)alkyl group selected from methyl, ethyl, n-propyl or 1-methylethyl; R⁶ is selected from hydrogen; straight or branched (C₁–C₃)alkyl group selected from methyl, ethyl, n-propyl or 1-methylethyl; with the proviso that R⁵ and R⁶ cannot both be hydrogen; or R⁵ and R⁶ taken together are —(CH₂)₂W(CH₂)₂—, wherein W is selected from (CH₂)ₙ and n=0–1, —NH, —N(C₁–C₃)alkyl [straight or branched], —N(C₁–C₄)alkoxy, oxygen, sulfur or substituted congeners selected from (L or D)proline, ethyl(L or D)prolinate, morpholine, pyrrolidine or piperidine;and the pharmacologically acceptable organic and inorganic salts or metal complexes.

Also included in the present invention are compounds useful as intermediates for producing the above compounds of formula I and II. Such intermediate compounds include those having the formula III and IV:

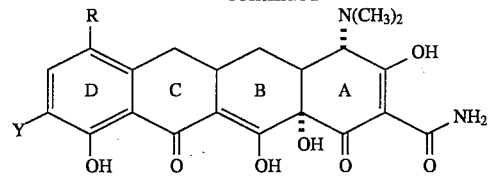

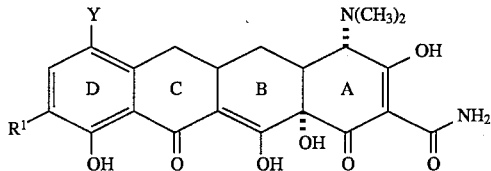

wherein: Y is selected from —N₂⁺Cl⁻ or —N₃; R or R¹ is selected from nitro; amino; halogen (selected from chlorine, bromine, fluorine or iodine); cyano; hydroxy; or —NR²R³; and when R or R¹=—NR²R³ and R²= hydrogen, R³= methyl, ethyl, n-propyl, 1-methylethyl, n-butyl, 1-methylpropyl, 2-methylpropyl or 1,1-dimethylethyl; and when R²= methyl or ethyl, R³= methyl, ethyl, n-propyl, 1-methylethyl, n-butyl, 1-methylpropyl or 2-methylpropyl; and when R²= n-propyl, R³= n-propyl, 1-methylethyl, n-butyl, 1-methylpropyl or 2-methylpropyl; and when R²= 1-methylethyl, R³= n-butyl, 1-methylpropyl or 2-methylpropyl; and when R2= n-butyl, R³= n-butyl, 1-methylpropyl or 2-methylpropyl; and when R²=1-methylpropyl, R³= 2-methylpropyl; and when R or R¹=—NR²R³ and R²= hydrogen, R³ is selected from R⁴(CH₂)ₙCO— or R⁴'(CH₂)ₙSO₂—; and when R³= R⁴(CH₂)ₙCO— and n=0, R⁴ is selected from hydrogen; amino; hydroxyamino; straight or branched mono(C₁–C₆)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C₃–C₈)cycloalkylamino group selected from cyclopropyl, trans-1,2-dimethyl-cyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-(C₁–C₆)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C₁–C₆)alkoxyamino group selected from methoxy, ethoxy, propoxy, butoxy, pentoxy or hexoxyamino; (C₃–C₈)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; (C₇–C₁₀)aralkoxyamino group selected from benzyloxy, 2-phenylethoxy, α-phenylethoxy, (2-naphthyl)methoxy, (1-naphthyl)methoxy, or phenylpropoxyamino; (C₂–C₈)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex- 2-yl, 5-azabicyclo[2.1.1] hex-5-yl, 2-azabicyclo-[ 2.2.1]hept-2-yl, 7-azabicyclo [2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)-alkoxypiperazinyl, thiamorpholinyl, tetrahydro-1,2-oxazinyl, isoxazolidinyl, pyrazolidinyl, 2-methyl-pyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-( 1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo-($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl; α-hydroxy($C_1$–$C_3$)alkyl group selected from hydroxymethyl, α-hydroxyethyl, α-hydroxy-1-methylethyl or α-hydroxypropyl; α-mercapto($C_1$–$C_3$)alkyl group selected from mercaptomethyl, α-mercaptoethyl, α-mercapto-1-methylethyl or α-mercaptopropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

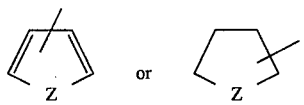

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

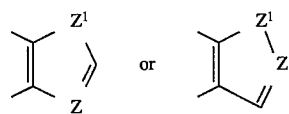

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

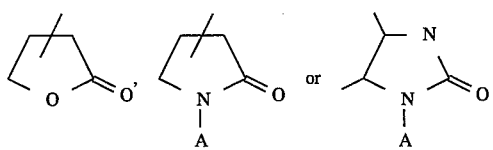

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclo-propyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

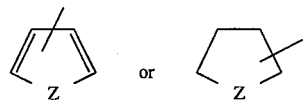

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

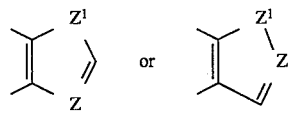

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

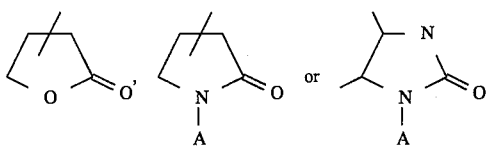

(A is selected from hydrogen; straight or branched (C$_1$–C$_4$)alkyl; C$_6$-aryl; substituted C$_6$-aryl (substitution selected from halo,(C$_1$–C$_4$)alkoxy, trihalo(C$_1$–C$_3$)alkyl, nitro, amino, cyano, (C$_1$–C$_4$)-alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C$_1$–C$_3$)alkylthiopyridazinyl, or a six membered saturated ring with one or two N, O, S or Se heteroatoms and an adjacent appended O heteroatom such as 2,3-dioxo-1-piperazinyl, 4-ethyl- 2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; (C$_1$–C$_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from (C$_1$–C$_3$)alkyl group, halogen, (C$_6$–C$_{10}$)aryl group selected from phenyl, α-naphthyl, β-naphthyl, substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy), halo-(C$_1$–C$_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

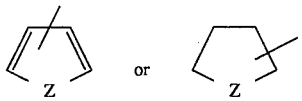

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; (C$_1$–C$_4$)alkoxy group such as allyloxy, methoxy, ethoxy, n-propoxy, n-butoxy or tert-butoxy; C$_6$-aryloxy group selected from phenoxy or substituted phenoxy (substitution selected from halo, (C$_1$–C$_4$)alkyl, nitro, cyano, thiol, amino, carboxy, di(C$_1$–C$_3$)alkylamino); (C$_7$–C$_{10}$)aralkyloxy group such as benzyloxy, 1-phenylethyloxy or 2-phenylethyloxy; vinyloxy or substituted vinyloxy group (substitution selected from (C$_1$–C$_4$)alkyl, cyano, carboxy, or (C$_6$–C$_{10}$)aryl selected from phenyl, α-naphthyl or β-naphthyl); R$^a$R$^b$amino(C$_1$–C$_4$)alkoxy group, wherein R$^a$R$^b$ is a straight or branched (C$_1$–C$_4$)alkyl selected from methyl, ethyl, n-propyl, 1-methylethyl, n-butyl, 1-methylpropyl, 2-methylpropyl or 1,1-dimethylethyl or R$^a$R$^b$ is (CH$_2$)$_n$, n=2–6, or —(CH$_2$)$_2$W(CH$_2$)$_2$— wherein W is selected from —N(C$_1$–C$_3$)alkyl [straight or branched], —NH, —NOB [B is selected from hydrogen or (C$_1$–C$_3$)alkyl], O or S; or R$^a$R$^b$aminoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W(CH$_2$)$_2$— wherein W is selected from —N(C$_1$–C$_3$)alkyl [straight or branched], —NH, —NOB [B is selected from hydrogen or (C$_1$–C$_3$)alkyl], O or S; and when R$^3$= R$_4$(CH$_2$)$_n$CO— and n=1–4, R$^4$ is selected from hydrogen; straight or branched (C$_1$–C$_4$)alkyl group selected from methyl, ethyl, n-propyl, 1-methylethyl, n-butyl, 1-methylpropyl, 2-methylpropyl or 1,1-dimethylethyl; (C$_3$–C$_6$)cycloalkyl group selected from cyclopropyl, cyclobutyl, cyclopentyl or cyclohexyl; substituted (C$_3$–C$_6$)cycloalkyl group (substitution selected from (C$_1$–C$_3$)alkyl, cyano, amino or (C$_1$–C$_3$)acyl); (C$_6$–C$_{10}$)aryl group selected from phenyl, α-naphthyl or β-naphthyl; substituted(C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group such as benzyl, 1-phenylethyl, 2-phenylethyl or phenylpropyl; acyloxy or haloacyloxy group, selected from acetyl, propionyl, chloroacetyl, trichloroacetyl, (C$_3$–C$_6$)cycloalkylcarbonyl, (C$_6$–C$_{10}$)aroyl selected from benzoyl or naphthoyl, halo substituted (C$_6$–C$_{10}$)aroyl such as pentafluorobenzoyl, 4-chlorobenzoyl, 3-bromobenzoyl or 3,4-difluorobenzoyl, (C$_1$–C$_4$)alkylbenzoyl such as 4-toluoyl, 2-toluoyl or 4-(1-methylethyl)benzoyl, (heterocycle)carbonyl, the heterocycle selected from a five membered aromatic or saturated ring with one N, O, S or Se heteroatom optionally having a benzo or pyrido ring fused thereto:

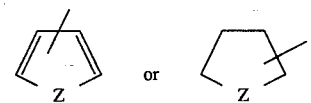

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

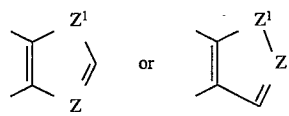

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

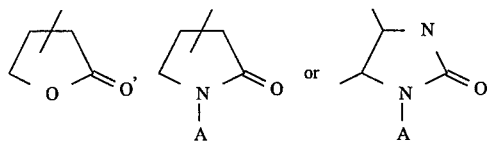

(A is selected from hydrogen; straight or branched (C$_1$–C$_4$)alkyl; C$_6$-aryl; substituted C$_6$-aryl (substitution selected from halo,(C$_1$–C$_4$)alkoxy, trihalo-(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy,n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di-($C_1$–$C_3$)alkylamino); ($C_7$–$C_{10}$)aralkyloxy group such as benzyloxy, 1-phenylethyloxy or 2-phenylethyloxy; ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di-($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_8$)aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

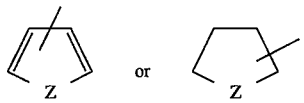

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

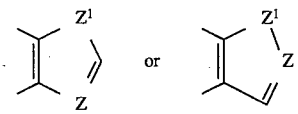

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

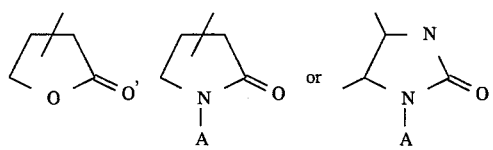

(A is selected from hydrogen; straight or branched ($C_1$–$C_4$)alkyl; $C_6$-aryl; substituted $C_6$-aryl (substitution selected from halo, ($C_1$–$C_4$) alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; hydroxy group; mercapto group; α-hydroxy($C_1$–$C_3$)alkyl group selected from hydroxymethyl, α-hydroxyethyl or α-hydroxy-1-methylethyl or α-hydroxypropyl; halo-($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl, 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

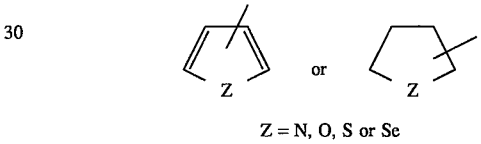

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

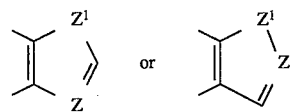

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

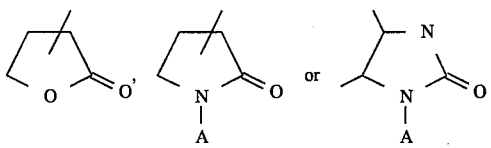

(A is selected from hydrogen; straight or branched ($C_1$–$C_4$) alkyl; $C_6$-aryl; substituted $C_6$-aryl (substitution selected from halo, ($C_1$–$C_4$) alkoxy, trihalo($C_1$–$C_3$)alkyl, nitro, amino, cyano, ($C_1$–$C_4$) alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxycarbonyl, allyloxycarbonyl or straight or branched butoxycarbonyl; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$— wherein W is selected from —N($C_1$–$C_3$)alkyl [straight or branched], —NH, —NOB [B is selected from hydrogen or ($C_1$–$C_3$)alkyl], O or S; and when $R^3= R^4(CH_2)_nCO$— and n=2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, or 2-azabicyclo[2.2.2]oct- 2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-( 1,2,3-triazolyl), 4-(1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when $R^3= R^{4'}(CH_2)_nSO_2$— and n= 0, $R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans- 2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans- 2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[ 2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex- 5-yl, 2-azabicyclo[2.2.1]hept-2-yl, 7-azabicyclo-[ 2.2.1hept-7-yl, or 2-azabicyclo[ 2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiomorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[2.2.1]hept-2-yl and where appropriate their diastereomers and enantiomers; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group such as benzyl, 1-phenylethyl, 2-phenylethyl or phenylpropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; a heterocycle group selected from a five membered aromatic or saturated ring with one N, O, S or Se heteroatom optionally having a benzo or pyrido ring fused thereto:

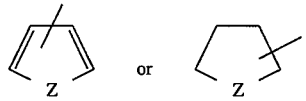

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

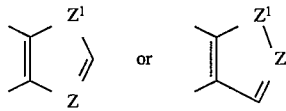

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

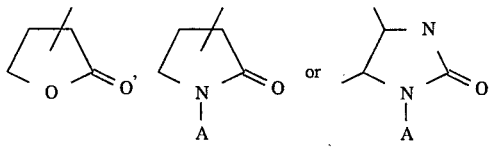

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl- 2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $R^aR^b$amino-($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$— $(CH_2)_2$— wherein W is selected from —N($C_1$–$C_3$)alkyl [straight or branched], —NH, —NOB [B is selected from hydrogen or ($C_1$–$C_3$)alkyl], O or S; and when $R^3$=$R^{4'}(CH_2)_nSO_2$— and n= 1–4, $R^{4'}$ is selected from hydrogen; amino; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_1$–$C_4$)carboxyalkyl group; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl; ($C_1$–$C_4$)alkoxy group such as allyloxy, methoxy, ethoxy, n-propoxy or tert-butoxy; $C_6$-aryloxy group selected from phenoxy or substituted phenoxy (substitution selected from halo, ($C_1$–$C_3$)alkyl, nitro, cyano, thiol, amino, carboxy, di-($C_1$–$C_3$)alkylamino); ($C_7$–$C_{10}$)aralkyloxy group such as benzyloxy, 1-phenylethyloxy or 2-phenylethyloxy; $R^aR^b$amino ($C_1$-$C_4$) alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)— alkyl [straight or branched], —NH, —NOB [B is selected from hydrogen or ($C_1$–$C_3$)alkyl], O or S; ($C_1$–$C_3$)alkylthio group selected from methylthio, ethylthio or n-propylthio; $C_6$-arylthio group selected from phenylthio or substituted phenylthio (substitution selected from halo, ($C_1$–$C_3$)alkyl, nitro, cyano, thiol, amino, carboxy, di-($C_1$–$C_3$)alkylamino); ($C_7$–$C_8$)aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

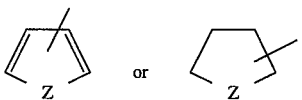

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

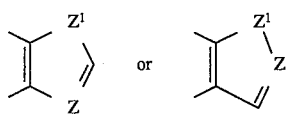

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[ 4,5-b]pyridyl or pyridylimidazolyl, or a five membered saturated ring with one or two N, O, S or Se heteroatoms and an adjacent appended O heteroatom:

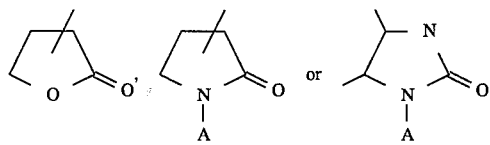

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$ ) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo- 1-piperazinyl, 4 -cyclopropyl-2 -dioxo-1-piperazinyl, 2-dioxomorpholinyl or 2-dioxothiomorpholinyl; hydroxy group; mercapto group; halo ($C_1$–$C_3$ ) alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

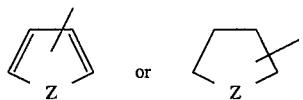

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

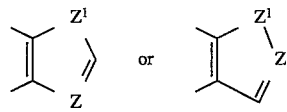

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[ 4,5-b]pyridyl or pyridylimidazolyl, or a five membered saturated ring with one or two N, O, S or Se heteroatoms and an adjacent appended O heteroatom:

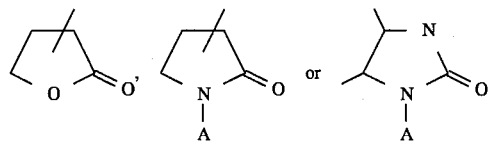

(A is selected from hydrogen; straight or branched ($C_1$–$C_4$ ) alkyl; $C_6$-aryl; substituted $C_6$-aryl (substitution selected from halo, ($C_1$–$C_4$ ) alkoxy, trihalo ($C_1$–$C_3$ )alkyl, nitro, amino, cyano, ($C_1$–$C_4$ ) alkoxycarbonyl, ($C_1$–$C_3$) alkylamino or carboxy); ($C_7$–$C_9$) aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl- 2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxycarbonyl, allyloxycarbonyl or straight or branched butoxycarbonyl; and the pharmacologically acceptable organic and inorganic salts or metal complexes.

Preferred compounds are compounds according to the above formula III and IV in which Y is selected from —$N_2^+$ or —$N_3$;

R and $R^1$ are the same or different and are selected from hydrogen; nitro; amino; halogen (selected from chlorine, bromine, fluorine or iodine); cyano; hydroxy or —$NR^2R^3$; and when R or $R^1$=—$NR_2R^3$ and $R^2$= hydrogen, $R^3$= methyl, ethyl, n-propyl, 1-methylethyl, n-butyl, 1-methylpropyl, 2-methylpropyl or 1,1-dimethylethyl; and when $R^2$=methyl or ethyl, $R^3$= methyl, ethyl, n-propyl, 1-methylethyl, n-butyl, 1-methylpropyl or 2-methylpropyl; and when R or $R^1$ = —$NR_2R^3$ and $R^2$= hydrogen, $R^3$ is selected from $R^4(CH_2)_nCO$— or $R^{4'}(CH_2)_nSO_2$—; and when $R^3$= $R^4(CH_2)_nCO$— and n=0, $R^4$ is selected from hydrogen; amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, thyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-di-methylcyclo-propoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo-[2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)-alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza- 5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_3$)alkyl group selected from methyl, ethyl, n-propyl or 1-methylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); α-hydroxy($C_1$–$C_3$)alkyl group selected from hydroxymethyl, α-hydroxyethyl, α-hydroxy-1-methylethyl or α-hydroxypropyl; halo-($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

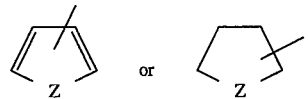

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

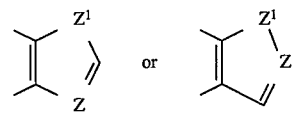

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

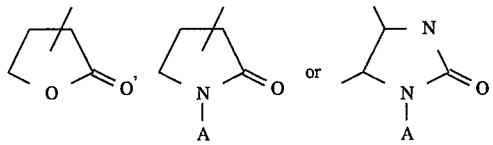

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-di-methylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methyltoluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

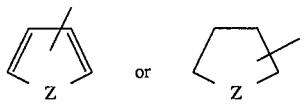

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

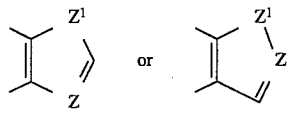

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

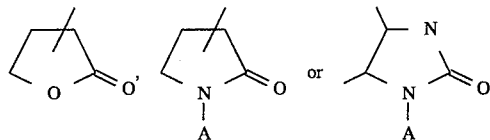

(A is selected from hydrogen; straight or branched $(C_1-C_4)$alkyl; $C_6$-aryl; substituted $C_6$-aryl (substitution selected from halo,$(C_1-C_4)$alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsymtriazinyl, pyrimidinyl or $(C_1-C_3)$ alkylthiopyridazinyl, or a six membered saturated ring with one or two N, heteroatoms and an adjacent appended O heteroatom such as 2,3-dioxo-1-piperazinyl, 4-ethyl- 2,3-dioxo-1-piperazinyl, 4-methyl-2,3-dioxo-1-piperazinyl, 4-cyclopropyl-2 -dioxo-1-piperazinyl, 2-dioxomorpholinyl or 2-dioxothiomorpholinyl; $(C_1-C_4)$ alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_3)$alkyl group, halogen, $(C_6-C_{10})$aryl group selected from phenyl, α-naphthyl, β-naphthyl, substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

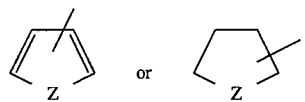

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; vinyloxy or substituted vinyloxy group (substitution selected from $(C_1-C_4)$alkyl, cyano, carboxy, or $(C_6-C_{10})$aryl selected from phenyl, α-naphthyl or β-naphthyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N$(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$— $(CH_2)_2$— wherein W is selected from —N$(C_1-C_3)$alkyl [straight or branched], —NH, —NOB [B is selected from hydrogen or $(C_1-C_3)$alkyl], O or S; and when $R^3$= $R^4(CH_2)_n$CO— and n=1–4 $R^4$ is selected from hydrogen; $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

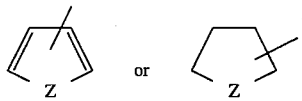

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

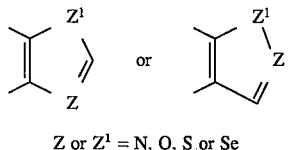

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

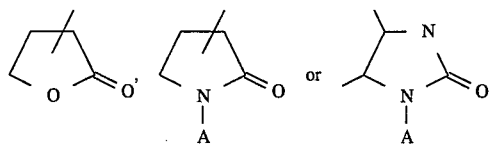

(A is selected from hydrogen; straight or branched ($C_1$–$C_4$) alkyl; $C_6$-aryl; substituted $C_6$-aryl (substitution selected from halo, ($C_1$–$C_4$) alkoxy, trihalo-($C_1$–$C_3$) alkyl, nitro, amino, cyano, (Cl-$C_4$) alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo- 1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy, n-butoxy or tert-butoxy; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$— wherein W is selected from —N($C_1$–$C_3$)alkyl [straight or branched], —NH, —NOB [B is selected from hydrogen or ($C_1$–$C_3$)alkyl], O or S; $C_6$-aryloxy group selected from phenoxy or substituted phenoxy (substitution selected from halo, ($C_1$–$C_4$)alkyl, nitro, cyano, thiol, amino, carboxy, di-($C_1$–$C_3$)alkylamino); ($C_1$–$C_3$)alkylthio. group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di-($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

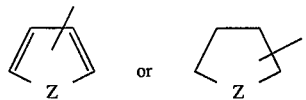

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O,S or Se heteroatoms optionally having a benzo or pyrido ring fused thereto:

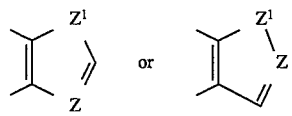

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

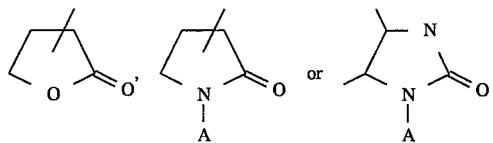

(A is selected from hydrogen; straight or branched ($C_1$–$C_4$)alkyl; $C_6$-aryl; substituted $C_6$-aryl (substitution selected from halo, ($C_1$–$C_4$) alkoxy, trihalo-($C_1$–$C_3$)alkyl, nitro, amino, cyano, ($C_1$–$C_4$) alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsymtriazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo- 1-piperazinyl, 2-dioxomorpholinyl or 2-dioxothiomorpholinyl; hydroxy group; α-hydroxy($C_1$–$C_3$)alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

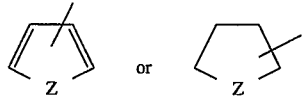

-continued

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

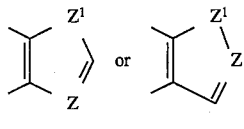

Z or Z¹ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

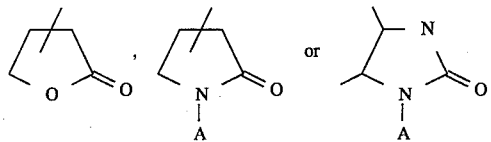

(A is selected from hydrogen; straight or branched ($C_1$–$C_4$) alkyl; $C_6$-aryl; substituted $C_6$-aryl (substitution selected from halo, ($C_1$–$C_4$)alkoxy, trihalo-($C_1$–$C_3$) alkyl, nitro, amino, cyano, ($C_1$–$C_4$) alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; and when $R^3 = R^4(CH_2)_n CO$— and n= 2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl- 1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl-( 1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo-[2.1.1]hex-5-yl, 2-azabicyclo[ 2.2.1]hept-2-yl, 7-azabicyclo[2.2.1]hept-7-yl, or 2-azabicyclo[2.2.2]-oct- 2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[ 2.2.1]hept-2-yl and where appropriate their diastereomers and enantiomers; azaheterocyclic group selected from 1-imidazolyl, 1-pyrrolyl, 1-( 1,2,3-triazolyl), 4-(1,2,4-triazolyl), 1-tetrazolyl, or 2-tetrazolyl; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when $R^3 = R^{4'}(CH_2)_n SO_2$— and n= 0, $R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl- 1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[ 2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[ 2.1.1]hex-2-yl, 5-azabicyclo[ 2.1.1] hex-5-yl, 2-azabicyclo[2.2.1]hept-2-yl, 7-azabicyclo[2.2.1] hept- 7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept- 2-yl, or 2,5-diaza-5-methylbicyclo[ 2.2.1]hept-2-yl and where appropriate their diastereomers and enantiomers; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl-)methyl or phenylpropylamino; straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); a heterocycle group selected from a five membered aromatic or saturated ring with one N, O, S or Se heteroatom optionally having a benzo or pyrido ring fused thereto:

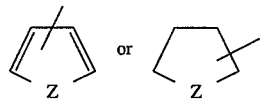

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

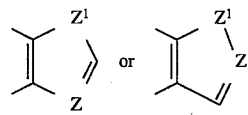

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

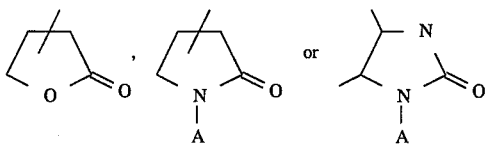

(A is selected from hydrogen; straight or branched $(C_1-C_4)$alkyl; $C_6$-aryl; substituted $C_6$-aryl (substitution selected from halo,$(C_1-C_4)$alkoxy, trihalo-$(C_1-C_3)$alkyl, nitro, amino, cyano, $(C_1-C_4)$ alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or a six membered saturated ring with one or two N, O, S or Se heteroatoms and an adjacent appended O heteroatom such as 2,3-dioxo-1-piperazinyl, 4-ethyl- 2,3-dioxo-1-piperazinyl, 4-methyl-2,3-dioxo- 1-piperazinyl, 4-cyclopropyl-2-dioxo-1-piperazinyl, 2-dioxomorpholinyl or 2-dioxothiomorpholinyl; and when $R^3 = R^{4'}(CH_2)_n SO_2$— and n=1–4, $R^{4'}$ is selected from hydrogen; amino; straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_1-C_4)$alkoxy group such as allyloxy, methoxy, ethoxy, n-propoxy, n-butoxy, iso-butoxy or tert-butoxy; $C_6$-aryloxy group selected from phenoxy or substituted phenoxy (substitution selected from halo, $(C_1-C_4)$alkyl, nitro cyano, thiol, amino, carboxy, di-$(C_1-C_3)$alkylamino; $(C_7-C_{10})$aralkyloxy group such as benzyloxy, 1-phenylethyloxy or 2-phenylethyloxy; $(C_1-C_4)$carboxyalkyl group; and the pharmacologically acceptable organic and inorganic salts or metal complexes.

Particularly preferred compounds are compounds according to the above formula III and IV in which Y is selected from —$N_2^+Cl^-$ or —$N_3$; R and $R^1$ are the same or different and are selected from hydrogen; nitro; amino; halogen (selected from chlorine, bromine, fluorine or iodine); cyano; hydroxy; or —$NR^2R^3$; and when R or $R^1$= —$NR^2R^3$ and $R^2$= hydrogen, $R^3$= methyl, ethyl, n-propyl, 1-methylethyl, n-butyl, 1-methylpropyl, 2-methylpropyl or 1,1-dimethylethyl; and when $R^2$= methyl or ethyl, $R^3$= methyl, ethyl, n-propyl, 1-methylethyl, n-butyl, 1-methylpropyl or 2-methylpropyl; and when R or $R^1$= —$NR^2R^3$ and $R^2$= hydrogen, $R^3$ is selected from $R^4(CH_2)_n CO$— or $R^{4'}(CH_2)_n SO_2$—; and when $R^3$= $R^4(CH_2)_n CO$— and n=0, $R^4$ is selected from hydrogen; amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,1-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2, 3-dimethylcyclobutyl, cis-2,3-dimethylcyclobutyl, cyclopentyl, cyclohexyl, cycloheptyl, cyclooctyl, bicyclo

[2.2.1]hept-2-yl, or bicyclo[2.2.2]oct-2-ylamino and where appropriate their diastereomers and enantiomers; straight or branched chain di-(C$_1$–C$_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C$_1$–C$_6$)alkoxyamino group selected from methoxy, ethoxy, propoxy, butoxy, pentoxy or hexoxyamino; (C$_3$–C$_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcycloproooxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; (C$_7$–C$_{10}$)aralkoxyamino group selected from benzyloxy, 2-phenylethoxy, α-phenylethoxy, (2-naphthyl)methoxy, (1-naphthyl)methoxy, or phenylpropoxyamino; (C$_2$–C$_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo-[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-(C$_1$–C$_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; (C$_6$–C$_{10}$)arylamino group selected from phenylamino or naphthylamino; (C$_7$–C$_{10}$)arylalkylamino group selected from benzyl, 2-phenylethyl, α-phenylethyl, (2-naphthyl)methyl, (1-naphthyl)methyl or phenylpropylamino; straight or branched (C$_1$–C$_3$)alkyl group selected from methyl, ethyl, n-propyl or 1-methylethyl; (C$_3$–C$_6$)cycloalkyl group selected from cyclopropyl, cyclobutyl, cyclopentyl or cyclohexyl; substituted (C$_3$–C$_6$)cycloalkyl group (substitution selected from (C$_1$–C$_3$)alkyl, cyano, amino or (C$_1$–C$_3$)acyl); (C$_6$–C$_{10}$)aryl group selected from phenyl, α-naphthyl or β-naphthyl; substituted (C$_6$–C$_{10}$)aryl group (substitution selected from halo, (C$_1$–C$_4$)alkoxy trihalo(C$_1$–C$_3$)alkyl, nitro, amino, cyano, (C$_1$–C$_4$)-alkoxycarbonyl, (C$_1$–C$_3$)alkylamino or carboxy); α-hydroxy(C$_1$–C$_3$)alkyl group selected from hydroxymethyl, α-hydroxyethyl, α-hydroxy-1-methylethyl or α-hydroxypropyl; halo(C$_1$–C$_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

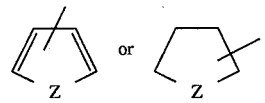

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

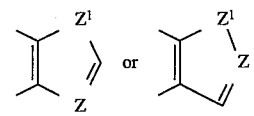

Z or Z$^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

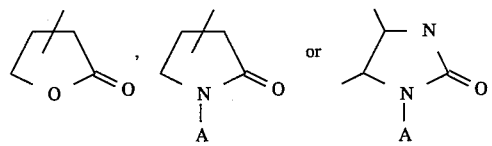

(A is selected from hydrogen; straight or branched (C$_1$–C4)alkyl; C$_6$-aryl; substituted C$_6$-aryl (substitution selected from halo, (C$_1$–C$_4$)alkoxy, trihalo-(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, (C$_3$–C$_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)-carbonyl or (3-ethylcyclobutyl)carbonyl, (C$_6$–C$_{10}$)aroyl selected from benzoyl or naphthoyl, halo substituted (C$_6$–C$_{10}$)aroyl such as pentafluorobenzoyl, 4-chlorobenzoyl, 3-bromobenzoyl or 3,4-difluorobenzoyl, (C$_1$–C$_4$)alkylbenzoyl such as 4-toluoyl, 2-methylbenzoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

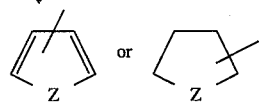

-continued

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

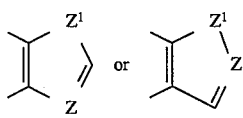

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

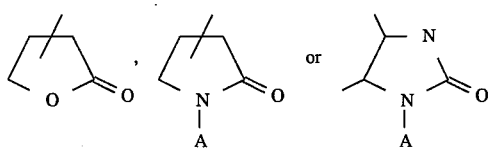

(A is selected from hydrogen; straight or branched $(C_1-C_4)$alkyl; $C_6$-aryl; substituted $C_6$-aryl (substitution selected from halo,$(C_1-C_4)$alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or-2-dioxothiomorpholinyl; $(C_1-C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_3)$alkyl group, halogen, $(C_6-C_{10})$aryl group selected from phenyl, α-naphthyl, β-naphthyl, substituted $(C_6-C_{10})$aryl group (substitution selected from halo, $(C_1-C_4)$alkoxy, $(C_1-C_4)$alkoxycarbonyl, $(C_1-C_3)$alkylamino or carboxy), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

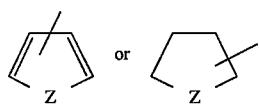

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$-alkyl); $(C_7-C_{10})$aralkyloxy group such as benzyloxy, 1-phenylethyloxy or 2-phenylethyloxy; and when $R^3=R^4(CH_2)_nCO-$ and n=1-4, $R^4$ is selected from hydrogen; $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)-carbonyl, the heterocycle selected from a five membered aromatic or saturated ring with one N, O, S or Se heteroatom optionally having a benzo or pyrido ring fused thereto:

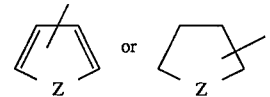

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

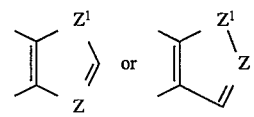

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

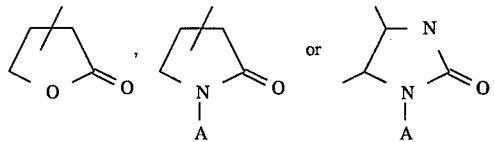

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di-$(C_1-C_3)$alkylamino); $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di-$(C_1-C_3)$alkylamino); $C_6$-arylsulfonyl group selected from phenylsulfonyl or substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); a heterocycle group selected from a five membered aromatic or saturated ring one N, O, S or Se heteroatom optionally having a benzo or pyrido ring fused thereto:

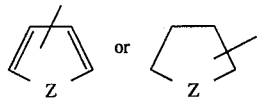

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

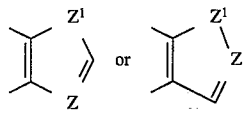

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

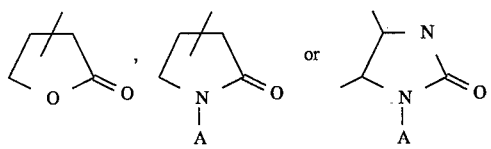

(A is selected from hydrogen; straight or branched $(C_1-C_4)$alkyl; $C_6$-aryl; substituted $C_6$-aryl (substitution selected from halo, $(C_1-C_4)$ alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy$(C_1-C_3)$alkyl group selected from hydroxymethyl, α-hydroxyethyl, α-hydroxy-1-methylethyl or α-hydroxypropyl; halo-$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromo-phenylcarbonyl or 3,4-difluorobenzoyl, $(C_1-C_4)$alkylbenzoyl such as from 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

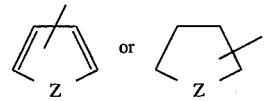

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

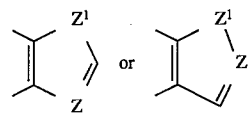

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

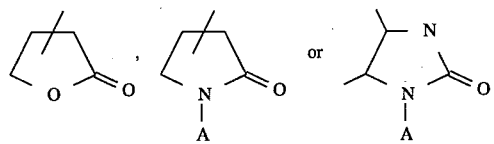

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; and when $R^3=R^4(CH_2)_nCO—$ and n=2–4, $R^4$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)-methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo-[2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl)methyl or phenylpropylamino; $(C_1-C_4)$alkoxycarbonylamino group selected from tert-butoxycarbonylamino, allyloxycarbonylamino, methoxycarbonylamino, ethoxycarbonylamino or propoxycarbonylamino; and when $R^3=R^{4'}(CH_2)_nSO_2$— and n=0, $R^{4'}$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)-methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo-[2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; azaheterocyclic group selected from 1-imidazolyl, 1-pyrrolyl, 1-(1,2,3-triazolyl), 4-(1,2,4-triazolyl), 1-tetrazolyl, or 2-tetrazolyl; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl)methyl or phenylpropylamino; straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); a heterocycle group selected from a five membered aromatic or saturated ring with one N, O, S or Se heteroatom optionally having a benzo or pyrido ring fused thereto:

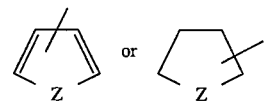

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl; and when $R^3=R^{4'}(CH_2)_nSO_2$— and n=1-4, $R^{4'}$ is selected from hydrogen; amino; straight or branched $(C_1-C_3)$alkyl group selected from methyl, ethyl, n-propyl or 1-methylethyl; and the pharmacologically acceptable organic and inorganic salts or metal complexes.

Most particularly preferred compounds are compounds according to the above formula III and IV in which Y is selected from —$N_2^+Cl^-$ or —$N_3$; R and $R^1$ are the same or different and are selected from hydrogen; nitro; amino; halogen (selected from chlorine, bromine, fluorine or iodine); cyano; hydroxy; or —$NR^2R^3$; and when R or $R^1$=—$NR^2R^3$ and $R^2$=hydrogen, $R^3$=methyl, ethyl, n-propyl, 1-methylethyl, n-butyl, 1-methylpropyl, 2-methylpropyl or 1,1-dimethylethyl; and when $R^2$=methyl or ethyl, $R^3$=methyl, ethyl, n-propyl, 1-methylethyl, n-butyl, 1-methylpropyl or 2-methylpropyl; and when R or $R^1$=—$NR^2R^3$ and $R^2$=hydrogen, $R^3$ selected from $R^4(CH_2)_nCO$— or $R^{4'}(CH_2)_nSO_2$—; and when $R^3$=$R^4(CH_2)_nCO$— and n=0, $R^4$ is selected from hydrogen; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyltrans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo-[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1, 2-oxazinyl, isoxazolidinyl, pyrazolidinyl, 2-methyl-pyrazolidinyl, 2,5-diazabicyclo[2.2.2]hept-2-yl, or 2,5-diaza-5-methylbicyclo[2.2.1]hept-2-yl and where appropriate their diastereomers and enantiomers; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_2$)alkyl group selected from methyl or ethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, nitro, amino); α-hydroxy($C_1$–$C_3$)alkyl group selected from hydroxymethyl; halo($C_1$–$C_3$)alkyl group such as bromomethyl, fluoromethyl, difluoro methyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

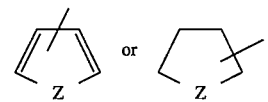

Z = N, O, S or Se such as indolyl, 2-pyrrolidinyl, 3-pyrrolidinyl, 2-pyrrolinyl, tetrahydrofuranyl, furanyl, benzofuranyl, tetrahydrothienyl or thienyl, or a five membered aromatic ring with two N, O, S or Se heteroatoms optionally having a benzo or pyrido ring fused thereto:

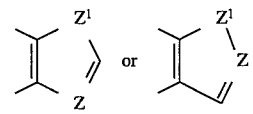

Z or $Z^1$ = N, O, S or Se such as imidazolyl, pyrazolyl, benzimidazolyl, indazolyl, thiazolyl or benzothiazolyl; ($C_1$–$C_4$)alkoxycarbonyl group selected from methoxycarbonyl, ethoxycarbonyl, straight or branched propoxycarbonyl, straight or branched butoxycarbonyl or allyloxycarbonyl; vinyl or substituted vinyl group [substitution selected from ($C_1$–$C_3$)alkyl group, ($C_6$–$C_{10}$)aryl group selected from phenyl, α-naphthyl, β-naphthyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl); ($C_7$–$C_{10}$)aralkyloxy group such as benzyloxy, 1-phenylethyloxy or 2-phenylethyloxy; and when $R^3$=$R^4(CH_2)_nCO$— and n=1–4, $R^4$ is selected from hydrogen; ($C_1$–$C_2$)alkyl group selected from methyl or ethyl; ($C_6$–$C_{10}$)aryl group selected from phenyl, α-naphthyl or β-naphthyl; substituted($C_6$–$C_{10}$)aryl group (substitution selected from halo, ($C_1$–$C_4$)alkoxy, trihalo($C_1$–$C_3$)alkyl); acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

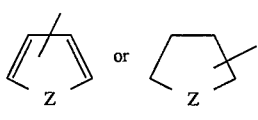

Z = N, O, S or Se such as tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

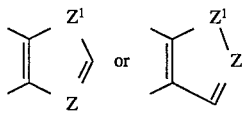

Z or $Z^1$ = N, O, S or Se such as pyrazolyl, benzimidazolyl, benzoxazolyl, indazolyl, thiazolyl or benzothiazolyl, or a six membered aromatic ring with one or two N heteroatoms such as pyridyl or pyridazinyl; ($C_1$–$C_4$) alkoxy group such as allyloxy, methoxy, ethoxy, n-propoxy, n-butoxy or tert-butoxy; α-hydroxy ($C_1$–$C_3$) alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; and when $R^3$=$R^4$($CH_2$)$_n$CO— and n=2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)-methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, or 2-azabicyclo-[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)-alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino;

and when $R^3$=$R^{4'}$($CH_2$)$_n$$SO_2$— and n=0, $R^{4'}$ is selected from amino; straight or branched ($C_1$–$C_2$)alkyl group selected from methyl or ethyl;

($C_6$–$C_{10}$)aryl group selected from phenyl, α-naphthyl or β-naphthyl; and when $R^3$=$R^{4'}$ ($CH_2$)$_n$$SO_2$— and n=1–4, $R^{4'}$ is selected from hydrogen; straight or branched ($C_1$–$C_2$)alkyl group selected from methyl or ethyl; and the pharmacologically acceptable organic and inorganic salts or metal complexes.

Compounds of special interest are compounds according to the above formula III and IV in which Y is —$N_2^+Cl^-$ or —$N_3$;

R or $R^1$ are selected from nitro; amino; halogen (selected from chlorine, bromine, fluorine or iodine); cyano; hydroxy; or —$NR^2R^3$; and when R or $R^1$=—$NR^2R^3$ and $R^2$=methyl or ethyl;

$R^3$=methyl or ethyl, and when R or $R^1$=—$NR^2R^3$ and $R^2$=hydrogen, $R^3$ is selected from $R^4$($CH_2$)$_n$CO— or $R^{4'}$ ($CH_2$)$_n$$SO_2$—; and when $R^3$=$R^4$($CH_2$)$_n$CO— and n=0, $R^4$ is selected from hydrogen; straight or branched ($C_1$–$C_2$)alkyl group selected from methyl or ethyl; a heterocycle group selected from a five membered aromatic or saturated ring with one N, O, or S heteroatom optionally having a benzo or pyrido ring fused thereto:

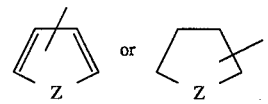

Z = N, O or S such as furanyl or thienyl, or a five membered aromatic ring with two N, O or S heteroatoms optionally having a benzo or pyrido ring fused thereto:

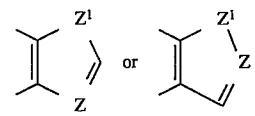

Z or $Z^1$ = N, O, or S such as pyrazolyl, benzimidazolyl or thiazolyl; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl); $(C_7-C_{10})$aralkyloxy group such as benzyloxy, 1-phenylethyloxy or 2-phenylethyloxy; and when $R^3=R^4(CH_2)_nCO-$ and n=1–4, $R^4$ is selected from hydrogen; $(C_1-C_2)$alkyl group selected from methyl or ethyl; $(C_6-C_{10})$aryl group selected from phenyl, α-naphthyl or β-naphthyl; and when $R^3=R^{4'}(CH_2)_nSO_2-$ and n=0, $R^{4'}$ is selected from straight or branched $(C_1-C_2)$alkyl group selected from methyl or ethyl; $(C_6-C_{10})$aryl group selected from phenyl, α-naphthyl or β-naphthyl; and the pharmacologically acceptable organic and inorganic salts or metal complexes.

Additional intermediate compounds include those having the formula V and VI:

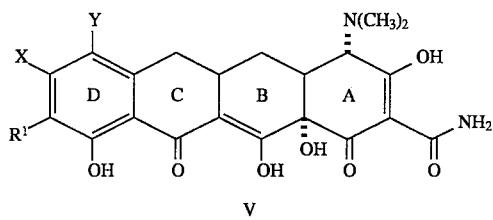

V

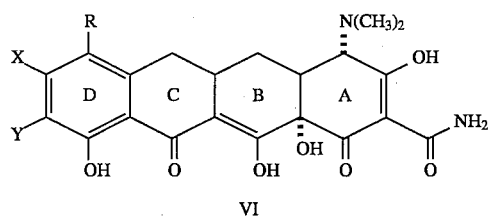

VI wherein:

Y is selected from $-N_2^+Cl^-$ or $N_3$;

X is selected from halogen or trifluoromethanesulfonyloxy; the halogen is selected from bromine, chlorine, fluorine or iodine;

R or $R^1$ is selected from nitro; amino; halogen (selected from chlorine, bromine, fluorine or iodine); cyano; hydroxy; or $-NR^2R^3$; and when R or $R^1=-NR^2R^3$ and $R^2$=hydrogen, $R^3$=methyl, ethyl, n-propyl, 1-methylethyl, n-butyl, 1-methylpropyl, 2-methylpropyl or 1,1-dimethylethyl; and when $R^2$=methyl or ethyl, $R^3$=methyl, ethyl, n-propyl, 1-methylethyl, n-butyl, 1-methylpropyl or 2-methylpropyl; and when $R^2$=n-propyl, $R^3$=n-propyl, 1-methylethyl, n-butyl, 1-methylpropyl or 2-methylpropyl; and when $R^2$=1-methylethyl, $R^3$=n-butyl, 1-methylpropyl or 2-methylpropyl; and when $R^2$=n-butyl, $R^3$=n-butyl, 1-methylpropyl or 2-methylpropyl; and when $R^2$=1-methylpropyl, $R^3$=2-methylpropyl; and when R or $R^1=-NR^2R^3$ and $R^2$=hydrogen, $R^3$ is selected from $R^4(CH_2)_nCO-$ or $R^{4'}(CH_2)_nSO_2-$; and when $R^3=R^4(CH_2)_nCO-$ and n=0, $R^4$ is selected from hydrogen; amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2-C_8)$-azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo-[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl)methyl or phenylpropylamino; straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_3-C_6)$cycloalkyl group selected from cyclopropyl, cyclobutyl, cyclo- pentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$aralkyl group selected from benzyl, 1-phenylethyl, 2-phenylethyl or phenylpropyl; α-hydroxy-($C_1$-$C_3$)alkyl group selected from hydroxymethyl, α-hydroxyethyl,α-hydroxy-1-methylethyl or α-hydroxypropyl; α-mercapto($C_1$-$C_3$)alkyl group selected from mercaptomethyl, α-mercaptoethyl, α-mercapto-1-methylethyl or α-mercaptopropyl; halo($C_1$-$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

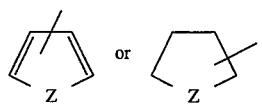

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

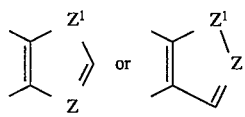

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O hetero-atom:

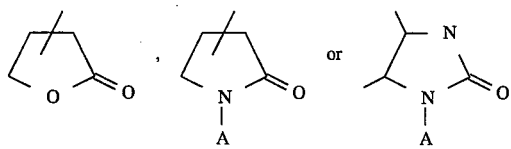

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)-alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$-$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$-$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$-$C_{10}$)-aroyl selected from benzoyl or naphthoyl, halo substituted ($C_6$-$C_{10}$)aroyl such as pentafluorobenzoyl, 4-chlorobenzoyl, 3-bromobenzoyl or 3,4-difluorobenzoyl, ($C_1$-$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

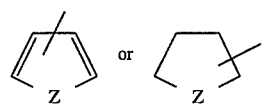

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

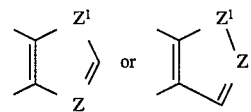

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

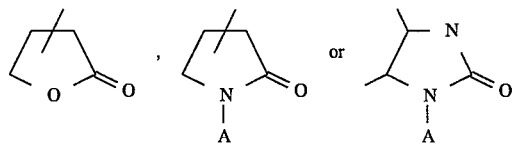

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)alkyl, nitro, amino, cyano, ($C_1$-$C_4$)-alkoxycarbonyl, ($C_1$-$C_3$)alkylamino or carboxy); ($C_7$-$C_9$)-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$-$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$-$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$-$C_3$)alkyl group, halogen, ($C_6$-$C_{10}$)aryl group selected from phenyl, α-naphthyl, β-naphthyl, substituted ($C_6$-$C_{10}$)aryl group (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy), halo($C_1$-$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

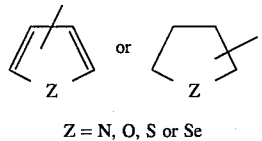

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di-$(C_1-C_3)$alkylamino); $(C_7-C_{10})$aralkyloxy group such as benzyloxy, 1-phenylethyloxy or 2-phenylethyloxy; vinyloxy or substituted vinyloxy group (substitution selected from $(C_1-C_4)$alkyl, cyano, carboxy, or $(C_6-C_{10})$aryl selected from phenyl, α-naphthyl or β-naphthyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, 2-methylpropyl or 1,1-dimethylethyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; and when $R^3=R^4(CH_2)_nCO$— and n=1–4, $R^4$ is selected from hydrogen; straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted$(C_6-C_{10})$-aryl group (substitution selected from halo, $(C_1-C_4)$-alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group such as benzyl, 1-phenylethyl, 2-phenylethyl or phenylpropyl; acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl or 4-(1-methylethyl)benzoyl, (heterocycle)carbonyl, the heterocycle selected from a five membered aromatic or saturated ring with one N, O, S or Se heteroatom optionally having a benzo or pyrido ring fused thereto:

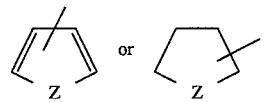

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

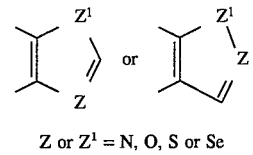

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

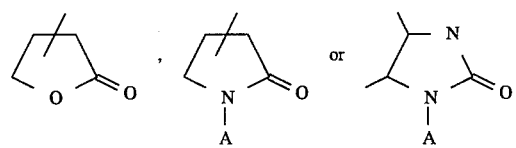

(A is selected from hydrogen; straight or branched $(C_1-C_4)$alkyl; $C_6$-aryl; substituted $C_6$-aryl (substitution selected from halo,$(C_1-C_4)$alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di-$(C_1-C_3)$alkylamino); $(C_7-C_{10})$aralkyloxy group such as benzyloxy, 1-phenylethyloxy or 2-phenylethyloxy; $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di-$(C_1-C_3)$alkylamino); $C_6$-arylsulfonyl group selected from phenylsulfonyl or substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

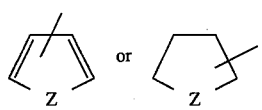

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O,S or Se heteroatoms optionally having a benzo or pyrido ring fused thereto:

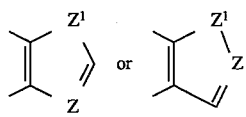

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

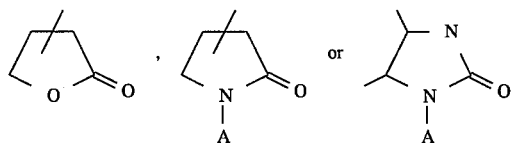

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; mercapto group; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl, 3,4-difluorobenzoyl, $(C_1-C_4)$alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

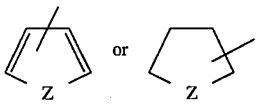

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl,benzofuranyl, tetrahydrothienyl, thienyl, benzothienyl or selenazolyl, or a five membered aromatic ring with two N, O, S or Se heteroatoms optionally having a benzo or pyrido ring fused thereto:

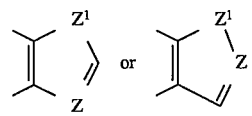

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatomsand an adjacent appended O heteroatom:

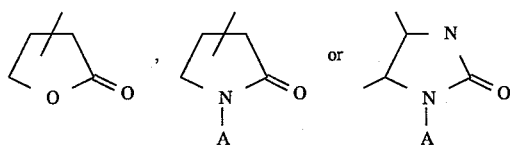

(A is selected from hydrogen; straight or branched $(C_1-C_4)$alkyl; $C_6$-aryl; substituted $C_6$-aryl (substitution selected from halo,$(C_1-C_4)$alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropy1-2-dioxo-1-piperazinyl, 2-dioxomorpholinyl or 2-dioxothiomorpholinyl; $(C_1-C_4)$alkoxycarbonyl group selected from methoxycarbonyl, ethoxycarbonyl, straight or branched propoxycarbonyl, allyloxycarbonyl or straight or branched butoxycarbonyl; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$—wherein W is selected from —$N(C_1-C_3)$alkyl [straight or branched], —NH, —NOB [B is selected from hydrogen or $(C_1-C_3)$alkyl], O or S; and when $R^3=R^4(CH_2)_nCO$— and n=2–4, $R^4$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-Yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo-[2.1.1]hex-5-yl, 2-azabicyclo[2.2.1]hept-2-yl, 7-azabicyclo[2.2.1]hept-7-yl, or 2-azabicyclo[2.2.2]-oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1, 2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl)methyl or phenylpropylamino; $(C_1-C_4)$alkoxycarbonylamino group selected from tertbutoxycarbonylamino, allyloxycarbonylamino, methoxycarbonylamino, ethoxycarbonylamino or propoxycarbonylamino;

and when $R^3=R^{4'}(CH_2)_nSO_2$— and n=0, $R^{4'}$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2, 3-dimethylcyclobutyl, cis-2,3-dimethylcyclobutyl, cyclopentyl, cyclohexyl, cycloheptyl, cyclooctyl, bicyclo [2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1, 2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo [2.2.1]hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group such as benzyl, 1-phenylethyl, 2-phenylethyl or phenylpropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; a heterocycle group selected from a five membered aromatic or saturated ring with one N, O, S or Se heteroatom optionally having a benzo or pyrido ring fused thereto:

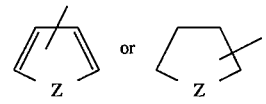

Z = N, O, S or Se such as pyrrolyl, N-methyl indolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

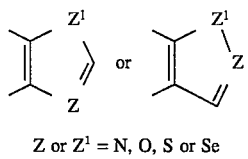

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

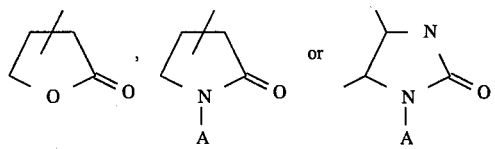

(A is selected from hydrogen; straight or branched $(C_1-C_4)$alkyl; $C_6$-aryl; substituted $C_6$-aryl (substitution selected from halo, $(C_1-C_4)$alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$—wherein W is selected from —$N(C_1-C_3)$alkyl [straight or branched], —NH, —NOB [B is selected from hydrogen or $(C_1-C_3)$alkyl], O or S; and when $R^3=R^{4'}$ $(CH_2)_nSO_2$— and n=1–4, $R^{4'}$ is selected from hydrogen; amino; straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_1-C_4)$carboxyalkyl group; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or group (substitution selected from halo, $(C_1-C_4)$alkoxy $(C_1-C_3)$acyl); $(C_6-C_{10})$aryl group selected from phenyl, α-naphthyl or β-naphthyl; substituted $(C_6-C_{10})$aryl trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl; $(C_1-C_4)$alkoxy group such as allyloxy, methoxy, ethoxy, n-propoxy or tert-butoxy; $C_6$-aryloxy group selected from phenoxy or substituted phenoxy (substitution selected from halo, $(C_1-C_3)$alkyl, nitro, cyano, thiol, amino, carboxy, di-$(C_1-C_3)$alkylamino); $(C_7-C_{10})$aralkyloxy group such as benzyloxy, 1-phenylethyloxy or 2-phenylethyloxy; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S;$(C_1-C_3)$alkylthio group selected from methylthio, ethylthio or n-propylthio; $C_6$-arylthio group selected from phenylthio or substituted phenylthio (substitution selected from halo, $(C_1-C_3)$alkyl, nitro, cyano, thiol, amino, carboxy, di-$(C_1-C_3)$alkylamino); $(C_7-C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

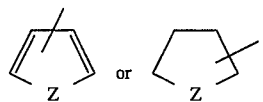

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

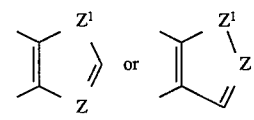

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

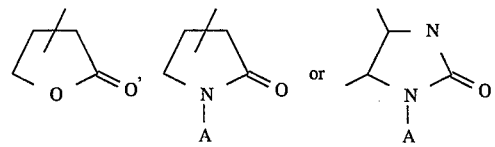

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C₁–C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; mercapto group; halo(C₁–C₃)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; acyl or haloacyl group selected from acetyl, propionyl, chloroacetyl, trifluoroacetyl, (C₃–C₆)cycloalkylcarbonyl, (C₆–C₁₀)aroyl selected from benzoyl or naphthoyl, halo substituted (C₆–C₁₀)aroyl such as pentafluorobenzoyl, 4-chlorobenzoyl, 3-bromobenzoyl or 3,4-difluorobenzoyl, (C₁–C₄)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

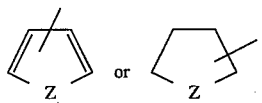

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

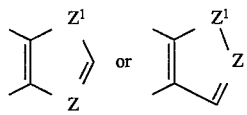

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

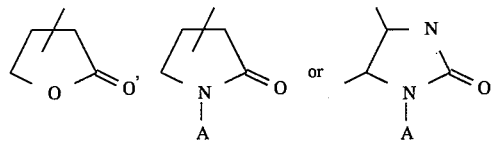

(A is selected from hydrogen; straight or branched (C₁–C₄)alkyl; C₆-aryl; substituted C₆-aryl (substitution selected from halo,(C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C₁–C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3- dioxo-1-piperazinyl, 4-cyclopropyl-2-dioxo-1-piperazinyl, 2-dioxomorpholinyl or 2-dioxothiomorpholinyl; (C₁–C₄)alkoxycarbonyl group selected from methoxycarbonyl, ethoxycarbonyl, straight or branched propoxycarbonyl, allyloxycarbonyl or straight or branched butoxycarbonyl; and the pharmacologically acceptable organic and inorganic salts or metal complexes.

Preferred compounds are compounds according to the above formula V and VI in which X is selected from halogen or trifluoromethanesulfonyloxy; the halogen is selected from bromine, chlorine, fluorine or iodine;

Y is selected from —N₂⁺Cl⁻ or N₃;

R or R¹ are selected from nitro; amino; halogen (selected from chlorine, bromine, fluorine or iodine); cyano; hydroxy or —NR²R³; and when R or R¹=—NR²R³ and R²=hydrogen, R³=methyl, ethyl, n-propyl, 1-methylethyl, n-butyl, 1-methylpropyl, 2-methylpropyl or 1,1-dimethylethyl; and when R²=methyl or ethyl, R³=methyl, ethyl, n-propyl, 1-methylethyl, n-butyl, 1-methylpropyl or 2-methylpropyl; and when R or R¹=—NR²R³ and R²=hydrogen, R³ is selected from R⁴(CH₂)ₙCO— or R⁴'(CH₂)ₙSO₂—; and when R³=R⁴(CH₂)ₙCO— and n=0, R⁴ is selected from hydrogen; amino; hydroxyamino; straight or branched mono(C₁–C₆)alkylamino group selected from methyl, ethyl, n-propyl, 1-methylethyl, n-butyl, 1-methylpropyl, 2-methylpropyl, 1,1-dimethylethyl, n-pentyl, 2-methyl-butyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C₃–C₈)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-(C₁–C₆)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; (C₁–C₆)alkoxyamino group selected from methoxy, ethoxy, propoxy, butoxy, pentoxy or hexoxyamino; (C₃–C₈)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.2]oct-2-yloxyamino and where appropriate their diastereomers and enantiomers; (C₇–C₁₀)aralkoxyamino group selected from benzyloxy, 2-phenylethoxy, α-phenylethoxy, (2-naphthyl- )methoxy, (1-naphthyl)methoxy, or phenylpropoxyamino; $(C_2-C_8)$azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo-[2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-$(C_1-C_4)$alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; $(C_6-C_{10})$arylamino group selected from phenylamino or naphthylamino; $(C_7-C_{10})$arylalkylamino group selected from benzyl, 2-phenylethyl, α-phenylethyl, (2-naphthyl)methyl, (1-naphthyl)methyl or phenylpropylamino; straight or branched $(C_1-C_3)$alkyl group selected from methyl, ethyl, n-propyl or 1-methylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); α-hydroxy$(C_1-C_3)$alkyl group selected from hydroxymethyl, α-hydroxyethyl, α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

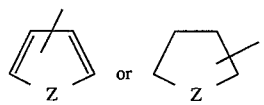

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyridoring fused thereto:

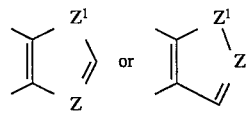

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

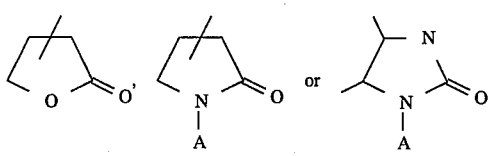

(A is selected from hydrogen; straight or branched $(C_1-C_4)$ alkyl; $C_6$-aryl; substituted $C_6$-aryl (substitution selected from halo, $(C_1-C_4)$ alkoxy, trihalo-$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, $(C_3-C_6)$cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-methyltoluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

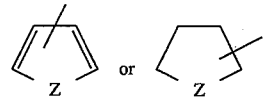

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

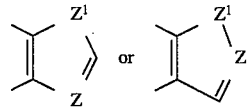

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

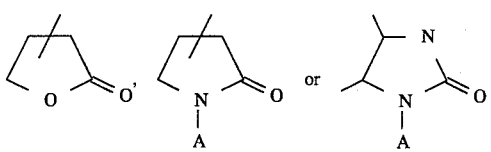

(A is selected from hydrogen; straight or branched (C$_1$–C$_4$)alkyl; C$_6$-aryl; substituted C$_6$-aryl (substitution selected from halo,(C$_1$–C$_4$)alkoxy, trihalo-(C$_1$–C$_3$)alkyl, nitro, amino, cyano, (C$_1$–C$_4$)-alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C$_1$–C$_3$) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; (C$_1$–C$_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from (C$_1$–C$_3$)alkyl group, halogen, (C$_6$–C$_{10}$)aryl group selected from phenyl, α-naphthyl, β-naphthyl, substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy), halo(C$_1$–C$_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

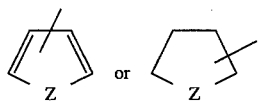

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; (C$_1$–C$_4$)alkoxy group such as allyloxy, methoxy, ethoxy, n-propoxy, n-butoxy or tert-butoxy; C$_6$-aryloxy group selected from phenoxy or substituted phenoxy (substitution selected from halo, (C$_1$–C$_4$)alkyl, nitro, cyano, thiol, amino, carboxy, di-(C$_1$–C$_3$)alkylamino); (C$_7$–C$_{10}$)aralkyloxy group such as benzyloxy, 1-phenylethyloxy or 2-phenylethyloxy; vinyloxy or substituted vinyloxy group (substitution selected from (C$_1$–C$_4$)alkyl, cyano, carboxy, or (C$_6$–C$_{10}$)aryl selected from phenyl, α-naphthyl or β-naphthyl); R$^a$R$^b$amino-(C$_1$–C$_4$)alkoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W(CH$_2$)$_2$— wherein W is selected from —N(C$_1$–C$_3$)—alkyl [straight or branched], —NH, —NOB [B is selected from hydrogen, or (C$_1$–C$_3$)alkyl], O or S; or R$^a$R$^b$aminoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W—(CH$_2$)$_2$—wherein W is selected from —N(C$_1$–C$_3$)alkyl [straight or branched], —NH, —NOB [B is selected from hydrogen or (C$_1$–C$_3$)alkyl], O or S; and when R$^3$=R$^4$(CH$_2$)$_n$CO— and n=1–4, R$^4$ is selected from hydrogen; (C$_1$–C$_3$)alkyl group selected from methyl, ethyl, n-propyl or 1-methylethyl; (C$_6$–C$_{10}$)aryl group selected from phenyl, α-naphthyl or β-naphthyl; substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); acyloxy or haloacyloxy group, selected from acetyl, propionyl, chloroacetyl, trichloroacetyl, (C$_3$–C$_6$)cycloalkylcarbonyl, (C$_6$–C$_{10}$)aroyl selected from benzoyl or naphthoyl, halo substituted (C$_6$–C$_{10}$)aroyl such as pentafluorobenzoyl, 4-chlorobenzoyl, 3-bromobenzoyl or 3,4-difluorobenzoyl, (C$_1$–C$_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

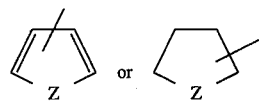

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

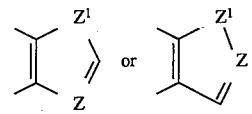

Z or Z$^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

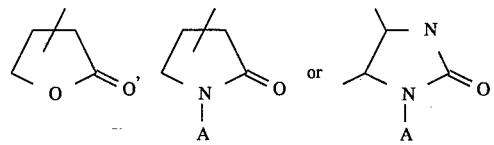

(A is selected from hydrogen; straight or branched (C$_1$–C$_4$)alkyl; C$_6$-aryl; substituted C$_6$-aryl (substitution selected from halo, (C$_1$–C$_4$)alkoxy, trihalo(C$_1$–C$_3$) alkyl, nitro, amino, cyano, (C$_1$–C$_4$) alkoxycarbonyl, (C$_1$–C$_3$) alkylamino or carboxy); (C$_7$–C$_9$) aralkyl group selected from benzyl, 1-phenylethyl, 2-phenylethyl or phenylpropyl )

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; (C$_1$–C$_4$)alkoxy group such as allyloxy, methoxy, ethoxy, n-propoxy, n-butoxy or tert-butoxy; $R^aR^b$amino($C_1$-$C_4$)alkoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2-6, or —$(CH_2)_2W(CH_2)_2$—wherein W is selected from —$N(C_1$-$C_3)$alkyl [straight or branched], —NH, —NOB [B is selected from hydrogen or ($C_1$-$C_3$)alkyl], O or S; or $R^aR^b$aminoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2-6, or —$(CH_2)_2W$—$(CH_2)_2$—wherein W is selected from —$N(C_1$-$C_3)$alkyl [straight or branched], —NH, —NOB [B is selected from hydrogen or ($C_1$-$C_3$)alkyl], O or S; $C_6$-aryloxy group selected from phenoxy or substituted phenoxy (substitution selected from halo, ($C_1$-$C_4$)alkyl, nitro, cyano, thiol, amino, carboxy, di-($C_1$-$C_3$)alkylamino); ($C_1$-$C_3$)alkylthio group selected from methylthio, ethylthio, propylthio or allylthio; $C_6$-arylthio group selected from phenylthio or substituted phenylthio (substitution selected from halo, ($C_1$-$C_4$)alkyl, nitro, cyano, thiol, amino, carboxy, di- ($C_1$-$C_3$) alkylamino); $C_6$-arylsulfonyl group selected from phenylsulfonyl or substituted phenylsulfonyl (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); a heterocycle group selected from a five membered aromatic or saturated ring with one N, O, S or Se heteroatom optionally having a benzo or pyrido ring fused thereto:

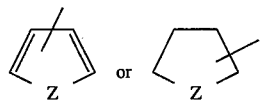

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

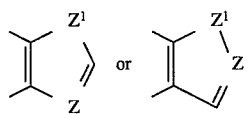

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

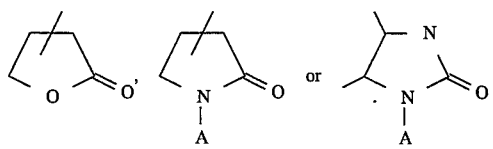

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)alkyl, nitro, amino, cyano, ($C_1$-$C_4$)-alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy($C_1$-$C_3$)alkyl group selected from hydroxymethyl, α-hydroxyethyl, α-hydroxy-1-methylethyl or α-hydroxypropyl; halo($C_1$-$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; acyl or haloacyl group selected from acetyl, propionyl, chloroacetyl, trifluoroacetyl, ($C_3$-$C_6$)cycloalkylcarbonyl, ($C_6$-$C_{10}$)aroyl selected from benzoyl or naphthoyl, halo substituted ($C_6$-$C_{10}$)aroyl such as pentafluorobenzoyl, 4-chlorobenzoyl, 3-bromobenzoyl or 3,4-difluorobenzoyl, ($C_1$-$C_4$)alkylbenzoyl such as 4-toluoyl, 2-toluoyl,or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

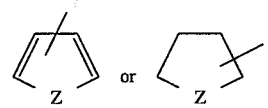

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

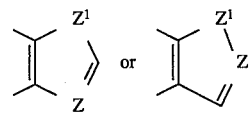

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

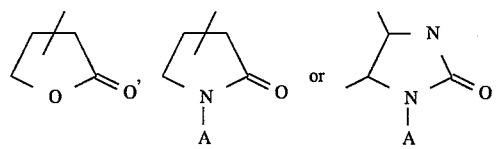

(A is selected from hydrogen; straight or branched ($C_1$-$C_4$)alkyl; $C_6$-aryl; substituted $C_6$-aryl (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; and when $R^3=R^4(CH_2)_nCO—$ and n=2–4, $R^4$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]-oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-Yl, or 2,5-diaza-5-methylbicyclo[2.2.1]hept-2-Yl and where appropriate their diastereomers and enantiomers; ($C_6$–$C_{10}$)arylamino group selected from phenylamino or naphthylamino; ($C_7$–$C_{10}$)arylalkylamino group selected from benzyl, 2-phenylethyl, α-phenylethyl, (2-naphthyl)methyl, (1-naphthyl)methyl or phenylpropylamino; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when $R^3=R^{4'}(CH_2)_nSO_2—$ and n=0, $R^{4'}$ is selected from amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; straight or branched ($C_1$–$C_3$)alkyl group selected from methyl, ethyl, n-propyl or 1-methylethyl; ($C_6$–$C_{10}$)aryl group selected from phenyl, α-naphthyl or p-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

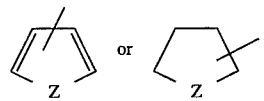

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

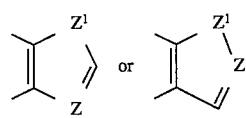

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

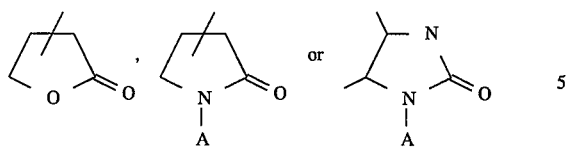

(A is selected from hydrogen; straight or branched ($C_1$–$C_4$) alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$) alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxo-thiomorpholinyl; and when $R^3=R^{4'}(CH_2)_nSO_2-$ and n=1–4, $R^{4'}$ is selected from hydrogen; amino; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_1$–$C_4$)alkoxy group such as allyloxy, methoxy, ethoxy, n-propoxy, n-butoxy, iso-butoxy or tert-butoxy; $C_6$-aryloxy group selected from phenoxy or substituted phenoxy (substitution selected from halo, ($C_1$–$C_4$)alkyl, nitro cyano, thiol, amino, carboxy, di-($C_1$–$C_3$)alkylamino; ($C_7$–$C_{10}$)aralkyloxy group such as benzyloxy, 1-phenylethyloxy or 2-phenylethyloxy; ($C_1$–$C_4$)carboxyalkyl group; and the pharmacologically acceptable organic and inorganic salts or metal complexes.

Particularly preferred compounds are compounds according to the above formula V and VI in which X is selected from halogen or trifluoromethanesulfonyloxy; the halogen is selected from bromine, chlorine, fluorine or iodine;

Y is selected from $-N_2^+Cl^-$ or $N_3$;

R or $R^1$ are selected from nitro; amino; halogen (selected from chlorine, bromine, fluorine or iodine); cyano; hydroxy; or $-NR^2R^3$;

and when R or $R^1=-NR^2R^3$ and $R^2$=hydrogen, $R^3$=methyl, ethyl, n-propyl, 1-methylethyl, n-butyl, 1-methylpropyl, 2-methylpropyl or 1,1-dimethylethyl; and when $R^2$=methyl or ethyl, $R^3$=methyl, ethyl, n-propyl, 1-methylethyl, n-butyl, 1-methylpropyl or 2-methylpropyl;

and when R or $R^1=-NR^2R^3$ and $R^2$=hydrogen, $R^3$ is selected from $R^4(CH_2)_nCO-$ or $R^{4'}(CH_2)_nSO_2-$; and when $R^3=R^4(CH_2)_nCO-$ and n=0, $R^4$ is selected from hydrogen; amino; hydroxyamino; straight or branched mono($C_1$–$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$–$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$–$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$–$C_6$)alkoxyamino group selected from methoxy, ethoxy, propoxy, butoxy, pentoxy or hexoxyamino; ($C_3$–$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$–$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$–$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, or 2-azabicyclo-[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$–$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[2.2.1]hept-2-yl and where appropriate their diastereomers and enantiomers; ($C_7$–$C_{10}$)arylalkylamino group selected from benzyl, 2-phenylethyl, α-phenylethyl, (2-naphthyl)methyl, (1-naphthyl)methyl or phenylpropylamino; straight or branched ($C_1$–$C_3$)alkyl group selected from methyl, ethyl, n-propyl or 1-methylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); α-hydroxy($C_1$–$C_3$)alkyl group selected from hydroxymethyl, α-hydroxyethyl, α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

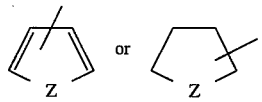

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

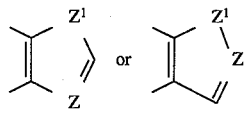

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

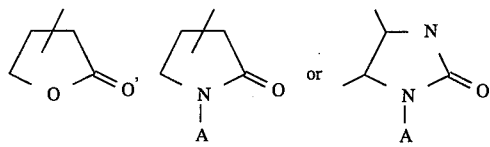

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, $(C_3-C_6)$cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-methylbenzoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

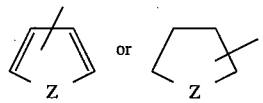

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

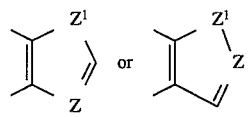

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

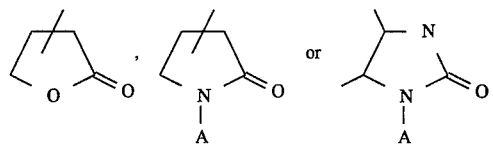

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_3)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_3)$alkyl group, halogen, $(C_6-C_{10})$aryl group selected from phenyl, α-naphthyl, β-naphthyl, substituted $(C_6-C_{10})$aryl group (substitution selected from halo, $(C_1-C_4)$alkoxy, $(C_1-C_4)$alkoxycarbonyl, $(C_1-C_3)$alkylamino or carboxy), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

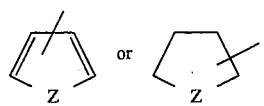

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl]; ($C_1$-$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$-$C_4$)alkyl); ($C_7$-$C_{10}$)aralkyloxy group such as benzyloxy, 1-phenylethyloxy or 2-phenylethyloxy;

and when $R^3=R^4(CH_2)_nCO$— and n=1–4, $R^4$ is selected from hydrogen; ($C_1$-$C_3$)alkyl group selected from methyl, ethyl, n-propyl or 1-methylethyl; ($C_6$-$C_{10}$)aryl group selected from phenyl, α-naphthyl or β-naphthyl; substituted ($C_6$-$C_{10}$)aryl group (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); acyloxy or haloacyloxy group, selected from acetyl, propionyl, chloroacetyl, trichloroacetyl, ($C_3$-$C_6$)cycloalkylcarbonyl, ($C_6$-$C_{10}$)aroyl selected from benzoyl or naphthoyl, halo substituted ($C_6$-$C_{10}$)aroyl such as pentafluorobenzoyl, 4-chlorobenzoyl, 3-bromobenzoyl or 3,4-difluorobenzoyl, ($C_1$-$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionaly having a benzo or pyrido ring fused thereto:

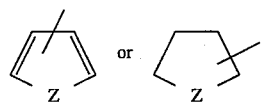

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

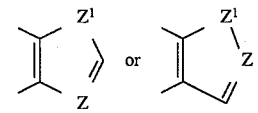

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

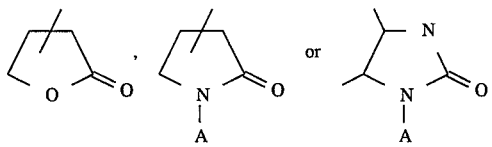

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$-$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$-$C_4$)alkyl, nitro, cyano, thiol, amino, carboxy, di-($C_1$-$C_3$)alkylamino); ($C_1$-$C_3$)alkylthio group selected from methylthio, ethylthio, propylthio or allylthio; $C_6$-arylthio group selected from phenylthio or substituted phenylthio (substitution selected from halo, ($C_1$-$C_4$)alkyl, nitro, cyano, thiol, amino, carboxy, di-($C_1$-$C_3$)alkylamino); $C_6$-arylsulfonyl group selected from phenylsulfonyl or substituted phenylsulfonyl (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); a heterocycle group selected from a five membered aromatic or saturated ring one N, O, S or Se heteroatom optionally having a benzo or pyrido ring fused thereto:

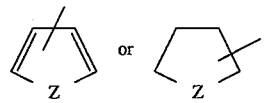

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl, or a five membered aromatic ring with two N, O,S or Se heteroatoms optionally having a benzo or pyrido ring fused thereto:

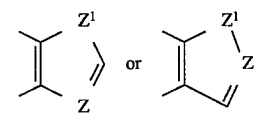

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

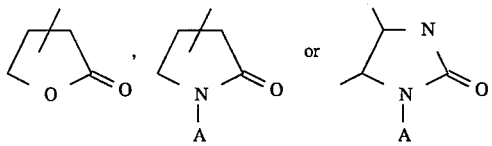

(A is selected from hydrogen; straight or branched ($C_1$-$C_4$) alkyl; $C_6$-aryl; substituted $C_6$-aryl (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; hydroxy group; α-hydroxy($C_1$-$C_3$)alkyl group selected from hydroxymethyl, α-hydroxyethyl, α-hydroxy-1-methylethyl or α-hydroxypropyl; halo($C_1$-$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, ($C_3$-$C_6$)cycloalkylcarbonyl, ($C_6$-$C_{10}$)aroyl selected from benzoyl or naphthoyl, halo substituted ($C_6$-$C_{10}$)aroyl such as pentafluorobenzoyl, 4-chlorobenzoyl, 3-bromophenylcarbonyl or 3,4-difluorobenzoyl, ($C_1$-$C_4$)alkylbenzoyl such as from 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

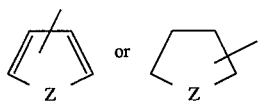

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, or benzothienyl, or a five membered aromatic ring with two N, O, S or Se heteroatoms optionally having a benzo or pyrido ring fused thereto:

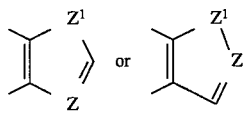

Z or $Z^1$ = N, O, S or Se such as imidazolyl, pyrazolyl, benzimidazolyl, oxazolyl, benzoxazolyl, indazolyl, thiazolyl or benzothiazolyl, or a five membered saturated ring with one or two N, O, S or Se heteroatoms and an adjacent appended O heteroatom:

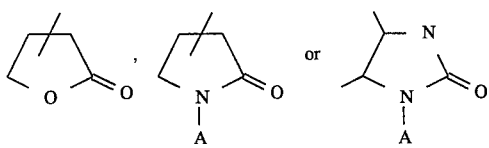

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl or pyrazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; and when $R^3$=$R^4$($CH_2$)$_n$CO— and n=2–4, $R^4$ is selected from amino; hydroxyamino; straight or branched mono($C_1$-$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$-$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$-$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1,-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$-$C_6$)alkoxyamino group selected from methoxy, ethoxy, propoxy, butoxy, pentoxy or hexoxyamino; ($C_3$-$C_8$)cycloalkoxyamino group selected from cyclopropoxy, trans-1,2-dimethylcyclopropoxy, cis-1,2-dimethyl-cyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$-$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$-$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]-hex-2-yl, 5-azabicyclo[2.1.1]hex-5-yl, 2-azabicyclo[2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$-$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methyl bicyclo[2.2.1]hept-2-yl and where appropriate their diastereomers and enantiomers; ($C_7$-$C_{10}$)arylalkylamino group selected from benzyl, 2-phenylethyl, α-phenylethyl, (2-naphthyl)methyl, (1-naphthyl)methyl or phenylpropylamino; ($C_1$-$C_4$)alkoxycarbonylamino group selected from tert-butoxycarbonylamino, allyloxycarbonylamino, methoxycarbonylamino, ethoxycarbonylamino or propoxycarbonylamino;

and when $R^3$=$R^{4'}$($CH_2$)$_n$$SO_2$— and n=0, $R^{4'}$ is selected from amino; hydroxyamino; straight or branched mono($C_1$-$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_3$-$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$-$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; ($C_1$-$C_6$)alkoxyamino group selected from methoxy, ethoxy, propoxy, butoxy, pentoxy or hexoxy-amino; ($C_3$-$C_8$)cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers; ($C_7$-$C_{10}$)aralkoxyamino group selected from benzyloxy, 2-phenylethoxy, α-phenylethoxy, (2-naphthyl)methoxy, (1-naphthyl)methoxy, or phenylpropoxyamino; straight or branched ($C_1$-$C_3$)alkyl group selected from methyl, ethyl, n-propyl or 1-methylethyl; ($C_6$-$C_{10}$)aryl group selected from phenyl, α-naphthyl or β-naphthyl; substituted ($C_6$-$C_{10}$)aryl group (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); a heterocycle group selected from a five membered aromatic or saturated ring with one N, O, S or Se heteroatom optionally having a benzo or pyrido ring fused thereto:

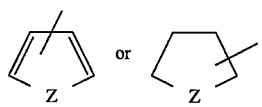

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl or benzothienyl; and when $R^3$=$R^{4'}$ ($CH_2$)$_n$$SO_2$— and n=1–4, $R^{4'}$ is selected from hydrogen; amino; straight or branched ($C_1$-$C_3$)alkyl group selected from methyl, ethyl, n-propyl or 1-methylethyl; and the pharmacologically acceptable organic and inorganic salts or metal complexes.

Most particularly preferred compounds are compounds according to the above formula V and VI in which X is selected from halogen or trifluoromethanesulfonyloxy; the halogen is selected from bromine, chlorine, fluorine or iodine;

Y is selected from —$N_2^+$$Cl^-$ or $N_3$;
R or $R^1$ are selected from nitro; amino; halogen (selected from chlorine, bromine, fluorine or iodine); cyano; hydroxy; or —$NR^2R^3$;
and when R or $R^1$=—$NR^2R^3$ and $R^2$=hydrogen,
$R^3$=methyl, ethyl, n-propyl, 1-methylethyl, n-butyl, 1-methylpropyl, 2-methylpropyl or 1,1-dimethylethyl;
and when $R^2$=methyl or ethyl,
$R^3$=methyl, ethyl, n-propyl, 1-methylethyl, n-butyl, 1-methylpropyl or 2-methylpropyl;
and when R or $R^1$=—$NR^2R^3$ and $R^2$=hydrogen,
$R^3$ selected from $R^4$($CH_2$)$_n$CO— or $R^{4'}$ ($CH_2$)$_n$$SO_2$—;
and when $R^3$=$R^4$($CH_2$)$_n$CO— and n=0,
$R^4$ is selected from hydrogen; amino; hydroxyamino; straight or branched mono($C_1$-$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers;
($C_3$-$C_8$)cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-($C_1$-$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers;
($C_1$-$C_6$)alkoxyamino group selected from methoxy, ethoxy, propoxy, butoxy, pentoxy or hexoxyamino; ($C_3$-$C_8$)cycycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1]hept-2-yloxy, or bicyclo[2.2.1]oct-2-yloxyamino and where appropriate their diastereomers and enantiomers;
($C_7$-$C_{10}$)aralkoxyamino group selected from benzyloxy, 2-phenylethoxy, α-phenylethoxy, (2-naphthyl)methoxy, (1-naphthyl)methoxy, or phenylpropoxyamino; ($C_2$-$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex- 2-yl, 5-azabicyclo[2.1.1]hex-5-yl, 2-azabicyclo[ 2.2.1]hept-2-yl, 7-azabicyclo[2.2.1]hept-7-yl, or 2-azabicyclo[2.2.2]oct-2-yl and where appropriate their diastereomers and enantiomers; azaheterocycloalkyl group selected from morpholinyl, piperazinyl, 4-methylpiperazinyl, 4-hydroxypiperazinyl, 4-($C_1$-$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo

[2.2.2]hept-2-yl, or 2,5-diaza-5-methylbicyclo[ 2.2.1] hept-2-yl and where appropriate their diastereomers and enantiomers; straight or branched $(C_1-C_2)$alkyl group selected from methyl or ethyl; $(C_6-C_{10})$aryl group selected from phenyl, a-naphthyl or β-naphthyl; substituted $(C_6-C_{10})$aryl group (substitution selected from halo, $(C_1-C_4)$alkoxy, nitro, amino); α-hydroxy$(C_1-C_3)$alkyl group selected from hydroxymethyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

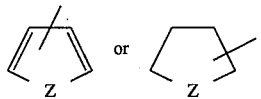

Z = N, O, S or Se such as indolyl, 2-pyrrolidinyl, 3-pyrrolidinyl, 2-pyrrolinyl, tetrahydrofuranyl, furanyl, benzofuranyl, tetrahydrothienyl or thienyl, or a five membered aromatic ring with two N, O, S or Se heteroatoms optionally having a benzo or pyrido ring fused thereto:

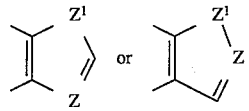

Z or $Z^1$ = N, O, S or Se such as imidazolyl, pyrazolyl, benzimidazolyl, indazolyl, thiazolyl or benzothiazolyl; $(C_1-C_4)$alkoxycarbonyl group selected from methoxycarbonyl, ethoxycarbonyl, straight or branched propoxycarbonyl, straight or branched butoxycarbonyl or allyloxycarbonyl; vinyl or substituted vinyl group [substitution selected from $(C_1-C_3)$alkyl group, $(C_6-C_{10})$aryl group selected from phenyl, α-naphthyl, β-naphthyl];
$(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl); $(C_7-C_{10})$aralkyloxy group such as benzyloxy, 1-phenylethyloxy or 2-phenylethyloxy;
and when $R^3=R^4(CH_2)_nCO-$ and n=1-4,
$R^4$ is selected from hydrogen; $(C_1-C_2)$alkyl group selected from methyl or ethyl; $(C_6-C_{10})$aryl group selected from phenyl, α-naphthyl or β-naphthyl; substituted$(C_6-C_{10})$aryl group (substitution selected from halo, $(C_1-C_4)$alkoxy, trihalo$(C_1-C_3)$alkyl); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

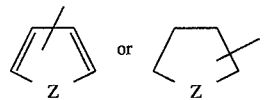

Z = N, O, S or Se such as tetrahydrofuranyl, furanyl, benzofuranyl, tetrahydrothienyl, thienyl or benzothienyl, or a five membered aromatic ring with two N, O, S or Se heteroatoms optionally having a benzo or pyrido ring fused thereto:

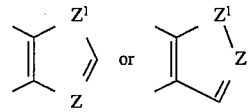

Z or $Z^1$ = N, O, S or Se such as pyrazolyl, benzimidazolyl, benzoxazolyl, indazolyl, thiazolyl or benzothiazolyl, or a six membered aromatic ring with one or two N heteroatoms such as pyridyl or pyridazinyl; $(C_1-C_4)$alkoxy group such as allyloxy, methoxy, ethoxy, n-propoxy, n-butoxy or tert-butoxy; α-hydroxy$(C_1-C_3)$alkyl group selected from hydroxymethyl, α-hydroxyethyl, α-hydroxy-1-methylethyl or α-hydroxypropyl; halo$(C_1-C_3)$alkyl group such as bromomethyl, fluoromethyl, difluoromethyl, trifluoro- methyl, chloromethyl, dichloromethyl, trichloromethyl, 2-fluoroethyl, 2,2-difluoroethyl, 2,2,2-trifluoroethyl, 2-bromoethyl or 2-iodoethyl;
and when $R^3=R^4(CH_2)_nCO-$ and n=2-4,
$R^4$ is selected from amino; hydroxyamino; straight or branched mono$(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_3-C_8)$cycloalkylamino group selected from cyclopropyl, trans-1,2-dimethylcyclopropyl, cis-1,2-dimethylcyclopropyl, trans-2,3-dimethylcyclopropyl, cis-2,3-dimethylcyclopropyl, cyclobutyl, trans-2,3-dimethylcyclobutyl, cis-2,3-dimethylcyclobutyl, cyclopentyl, cyclohexyl, cycloheptyl, cyclooctyl, bicyclo[2.2.1]hept-2-yl, or bicyclo[2.2.2]oct-2-ylamino and where appropriate their diastereomers and enantiomers; straight or branched chain di-$(C_1-C_6)$alkylamino group selected from dimethylamino, diethylamino, methyl(ethyl)amino, ethyl(1-methylethyl)amino or a combination of methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; $(C_1-C_6)$alkoxyamino group selected from methoxy, ethoxy, propoxy, butoxy, pentoxy or hexoxyamino; $(C_3-C_8)$cycloalkoxyamino group selected from cyclopropoxy, trans-1,2-dimethylcyclopropoxy, cis-1,2-dimethylcyclopropoxy, trans-2,3-dimethylcyclopropoxy, cis-2,3-dimethylcyclopropoxy, cyclobutoxy, trans-2,3-dimethylcyclobutoxy, cis-2,3-dimethylcyclobutoxy, cyclopentoxy, cyclohexoxy, cycloheptyloxy, cyclooctoxy, bicyclo[2.2.1] hept-2-yloxy, or bicyclo[2.2.1]oct-2-yloxyamino and where appropriate their diastereomers and enantiomers; $(C_7-C_{10})$aralkoxyamino group selected from benzyloxy, 2-phenylethoxy, α-phenylethoxy, (2-naphthyl)methoxy, (1-naphthyl)methoxy, or phenylpropoxyamino; ($C_2$-$C_8$)azacycloalkyl group selected from aziridinyl, azetidinyl, pyrrolidinyl, pyrrolinyl, piperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[ 2.1.1]hex-5-yl, 2-azabicyclo[2.2.1]hept-2-yl, 7-azabicyclo[ 2.2.1]hept-7-yl, or 2-azabicyclo [2.2.2]oct- 2-yl and where appropriate their diastereomers and enantiomers; azaheterocycloalkyl group selected from morpholinyl, piperazinyl, 4-methylpiperazinyl, 4-hydroxypiperazinyl, 4-($C_1$-$C_4$)alkoxypiperazinyl, thiamorpholinyl, tetrahydro-1,2-oxazinyl, isoxazolidinyl, pyrazolidinyl, 2-methylpyrazolidinyl, 2,5-diazabicyclo[2.2.2]hept-2-yl, or 2,5-diaza-5-methylbicyclo[ 2.2.1]hept-2-yl and where appropriate their diastereomers and enantiomers; ($C_1$-$C_4$)alkoxycarbonylamino group selected from tert-butoxycarbonylamino, allyloxycarbonylamino, methoxycarbonylamino, ethoxycarbonylamino or propoxycarbonylamino;

and when $R^3=R^{4'}(CH_2)_nSO_2$— and n=0, $R^{4'}$ is selected from amino; hydroxyamino; straight or branched mono($C_1$-$C_6$)alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; straight or branched chain di-($C_1$-$C_6$)alkylamino group selected from dimethylamino, diethylamino, methyl(ethyl)amino, ethyl(1-methylethyl)amino or a combination of methyl, ethyl, n-propyl, 1-methylethyl, n-butyl, 1-methyl- propyl, 2-methylpropyl, 1,1-dimethylethyl, n-pentyl-2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino and where appropriate their diastereomers and enantiomers; straight or branched ($C_1$-$C_2$)alkyl group selected from methyl or ethyl; ($C_6$-$C_{10}$)aryl group selected from phenyl, α-naphthyl or β-naphthyl;

and when $R^3=R^{4'}(CH_2)_nSO_2$— and n=1–4, $R^{4'}$ is selected from hydrogen; straight or branched ($C_1$-$C_2$)alkyl group selected from methyl or ethyl; and the pharmacologically acceptable organic and inorganic salts or metal complexes.

Compounds of special interest are compound according to the above formula in which X is selected from halogen or trifluoromethanesulfonyloxy; the halogen is selected from bromine, chlorine, fluorine or iodine;

Y is selected from —$N_2^+Cl^-$ or $N_3$;

R or $R^1$ are selected from nitro; amino; halogen (selected from chlorine, bromine, fluorine or iodine); cyano; hydroxy; or —$NR^2R^3$;

and when R or $R^1$=—$NR^2R^3$ and $R^2$=methyl or ethyl; $R^3$=methyl or ethyl, and when R or $R^1$=—$NR^2R^3$ and $R^2$=hydrogen, $R^3$ is selected from $R^4(CH_2)_nCO$— or $R^{4'}(CH_2)_nSO_2$—;

and when $R^3=R^4(CH_2)_nCO$— and n=0, $R^4$ is selected from hydrogen; straight or branched ($C_1$-$C_2$)alkyl group selected from methyl or ethyl; a heterocycle group selected from a five membered aromatic or saturated ring with one N, O, or S heteroatom optionally having a benzo or pyrido ring fused thereto:

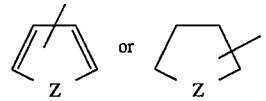

Z = N, O or S such as furanyl or thienyl, or a five membered aromatic ring with two N, O or S heteroatoms optionally having a benzo or pyrido ring fused thereto:

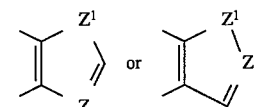

Z or $Z^1$ = N, O, or S such as pyrazolyl, benzimidazolyl or thiazolyl;

($C_1$-$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$-$C_4$)alkyl); ($C_7$-$C_{10}$)aralkyloxy group such as benzyloxy, 1-phenylethyloxy or 2-phenylethyloxy;

and when $R^3=R^4(CH_2)_nCO$— and n=1–4, $R^4$ is selected from hydrogen; ($C_1$-$C_2$)alkyl group selected from methyl or ethyl; ($C_6$-$C_{10}$)aryl group selected from phenyl, α-naphthyl or β-naphthyl;

and when $R^3=R^{4'}(CH_2)_nSO_2$— and n=0, $R^{4'}$ is selected from straight or branched ($C_1$-$C_2$)alkyl group selected from methyl or ethyl; ($C_6$-$C_{10}$)aryl group selected from phenyl, α-naphthyl or β-naphthyl; and the pharmacologically acceptable organic and inorganic salts or metal complexes.

DESCRIPTION OF THE PREFERRED EMBODIMENTS

The novel compounds of the present invention may be readily prepared in accordance with the following schemes.

The starting 7-azido-9-(substituted)-6-demethyl- 6-deoxytetracyclines or 9-azido-7-(substituted)- 6-demethyl-6-deoxytetracyclines described in formula 1 or the salts thereof are prepared by procedures known to those skilled in the art including those described in J. J. Hlavka, et al., J. Am. Chem. Soc., 84, 1426(1962).

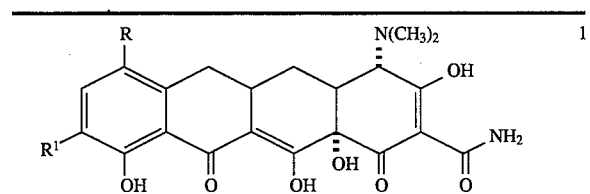

1a. $R^1 = N_3$ and R = $NR^2R^3$, $R^2 = R^3$
1b. $R^1 = N_3$ and R = $NR^2R^3$, $R^2 \neq R^3$
1c. R = $N_3$ and $R^1$ = $NR^2R^3$, $R^2 = R^3$
1d. R = $N_3$ and $R^1$ = $NR^2R^3$, $R^2 \neq R^3$
1e. $R^1 = N_3$ and R = X, X = halogen, hydrogen
1f. R = $N_3$ and $R^1$ = X, X = halogen, hydrogen The starting 7-azido-9-(substituted)-6-demethyl- 6-deoxytetracycline, 1, or 9-azido-7-(substituted)- 6-demethyl-6- deoxytetracycline, 1', described in formula 1 is prepared according to Scheme 1 or Scheme 2.

Scheme 1

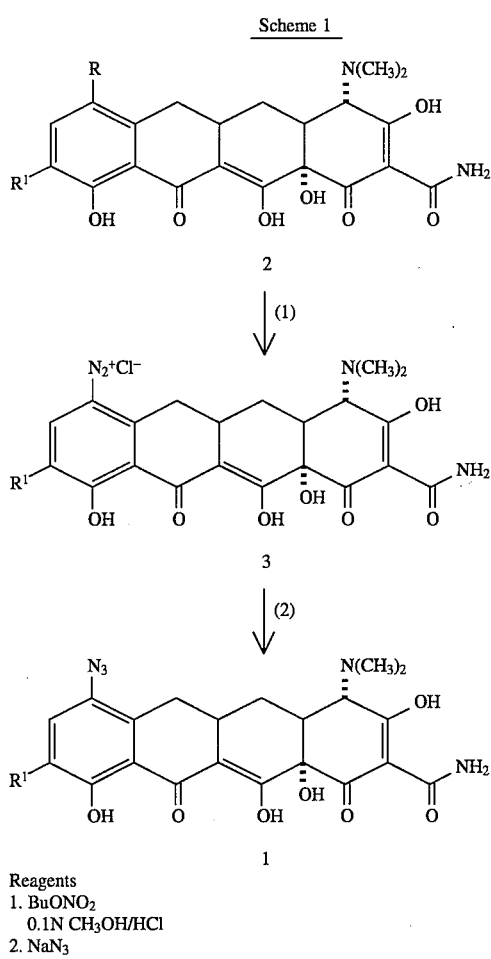

Reagents
1. BuONO$_2$
   0.1N CH$_3$OH/HCl
2. NaN$_3$
   0.1N CH$_3$OH/HCl

Scheme 2

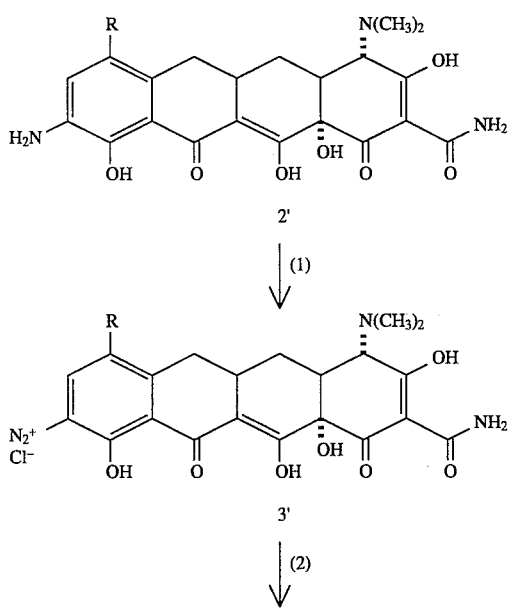

Scheme 2 -continued

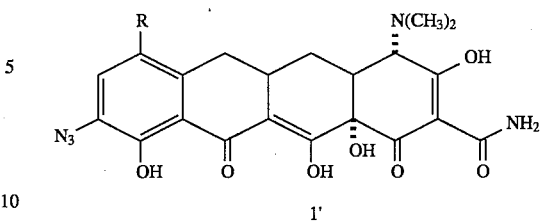

Reagents
1. BuONO$_2$
   0.1N CH$_3$OH/HCl
2. NaN$_3$
   0.1N CH$_3$OH/HCl

In accordance with Scheme 1 or 2, a 7-amino- 9-(substituted)-6-demethyl-6-deoxytetracycline 2, or 9-amino-7-(substituted)-6-demethyl-6-deoxytetracycline 2', or their mineral acid or halide salt, dissolved in 0.1N methanolic hydrogen chloride, is treated with an excess of n-butyl nitrite to give a 7-diazonium-9-(substituted)- 6-demethyl-6-deoxytetracycline, 3, or 9-diazonium-7-(substituted)-6-demethyl-6-deoxytetracycline, 3', or their mineral acid or halide salt The formed diazonium compound, 3 or 3', or their mineral acid or halide salt, dissolved in 0.1N methanolic hydrogen chloride, is treated with one equivalent of sodium azide to give the corresponding 7-azido-9-(substituted)-6-demethyl-6-deoxytetracycline, 1, or 9-azido-7-(substituted)-6-demethyl-6-deoxytetracycline, 1', or their mineral acid or halide salt

Scheme 3

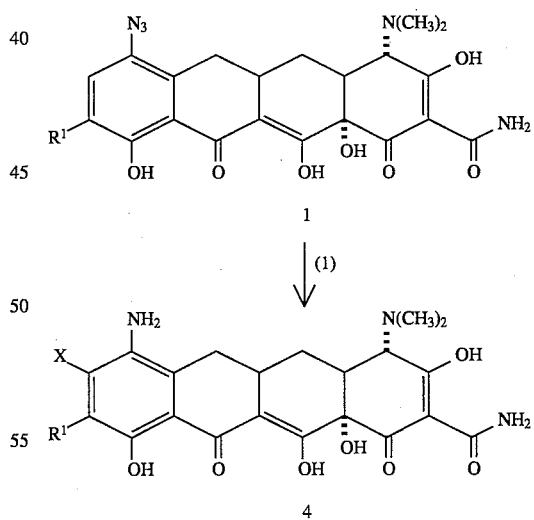

1. Strong acid
   (HCl, H$_2$SO$_4$, CF$_3$SO$_3$H, CH$_3$SO$_3$H,
   HI, HF and HBr)

Scheme 4

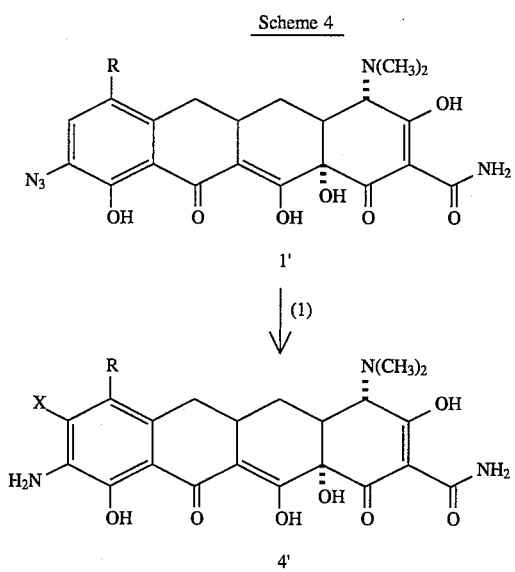

1. Strong acid
   (HCl, H₂SO₄, CF₃SO₃H, CH₃SO₃H, HI, HF and HBr)

In accordance with Scheme 3 or 4, a 7-azido-9-(substituted)-6-demethyl-6-deoxytetracycline, 1, or 9-azido-7-(substituted)-6-demethyl-6-deoxytetracycline, 1', or their mineral acid or halide salt, is treated with a strong acid, such as sulfuric acid, hydrochloric acid, methanesulfonic acid, trifluoromethanesulfonic acid, hydrobromic, hydroiodic, or hydrogen fluoride to produce a 7-amino-8-(substituted)-9-(substituted)-6-demethyl-6-deoxytetracycline, 4, or 9-amino-8-(substituted)-7-(substituted)-6-demethyl-6-deoxytetracycline, 4', or their mineral acid or halide salt.

The 7-amino-8-(substituted)-9-(substituted)-6-demethyl-6-deoxytetracycline, 4, or 9-amino-8-(substituted)-7-(substituted)-6-demethyl-6-deoxytetracycline, 4', or their mineral acid or halide salt, can be further converted as described in Schemes 5, 6, 7 and 8.

Scheme 5

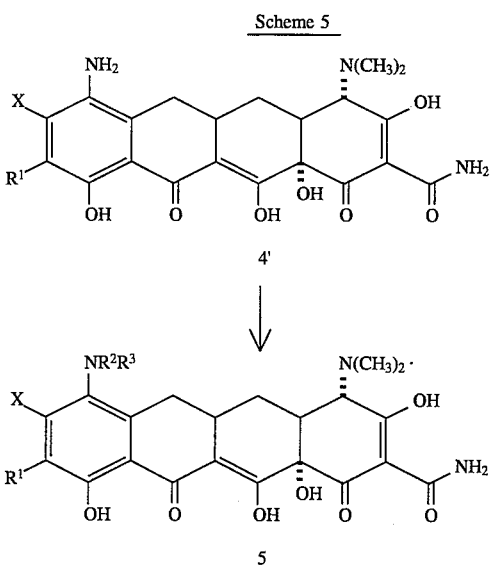

Scheme 6

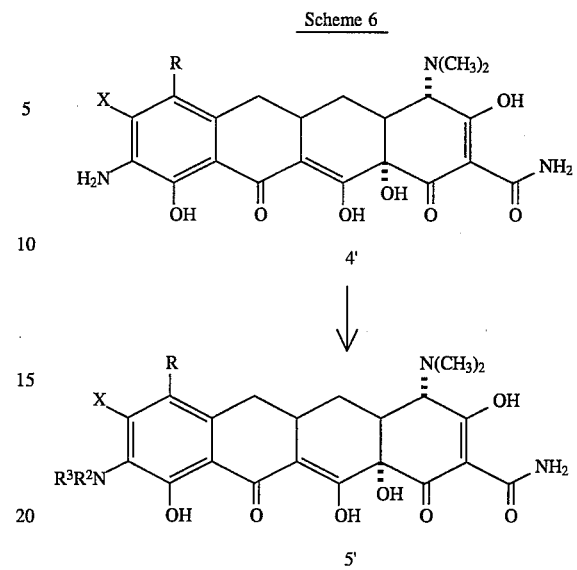

In accordance with Scheme 5 or 6, a 7-amino-8-(substituted)-9-(substituted)-6-demethyl-6-deoxytetracycline, 4, or a 9-amino-8-(substituted)-7-(substituted)-6-demethyl-6-deoxytetracycline, 4', or their mineral acid or halide salt, is treated with an acyl chloride, acyl anhydride, mixed acyl anhydride, sulfonyl chloride or sulfonyl anhydride in the presence of a suitable acid scavenger in a variety of solvents to form the corresponding 7-(acyl or sulfonyl amino)-8-(substituted)-9-(substituted)-6-demethyl-6-deoxytetracycline, 5, or 9-(acyl or sulfonyl amino)-8-(substituted)-7-(substituted)-6-demethyl-6-deoxytetracycline, 5', or their mineral acid or halide salt. The acid scavenger is selected from sodium bicarbonate, sodium acetate, pyridine, triethylamine, N,O-bis(trimethylsilyl)acetamide, N,O-bis(trimethylsilyl)trifluoroacetamide, potassium carbonate or a basic ion-exchange resin. The solvents are selected from water-tetrahydrofuran, N-methylpyrrolidone, 1,3-dimethyl-2-imidazolidinone, hexamethylphosphoramide, 1,3-dimethyl-3,4,5,6-tetrahydro-2(1H)pyrimidinone or 1,2-dimethoxyethane.

Scheme 7

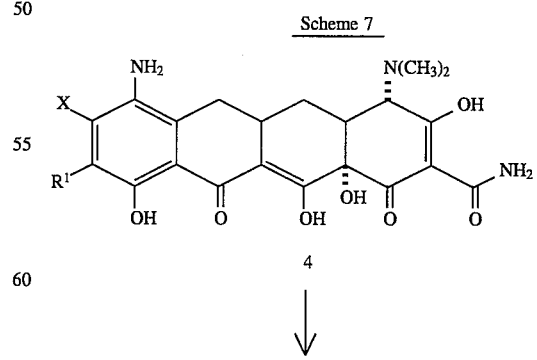

-continued
Scheme 7

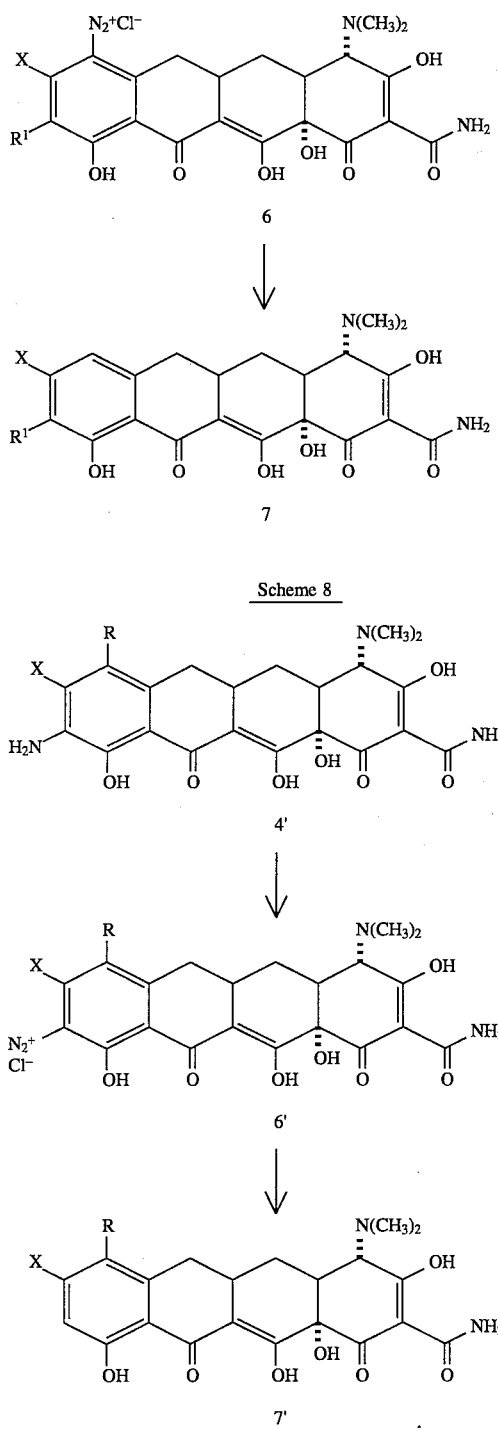

Scheme 8

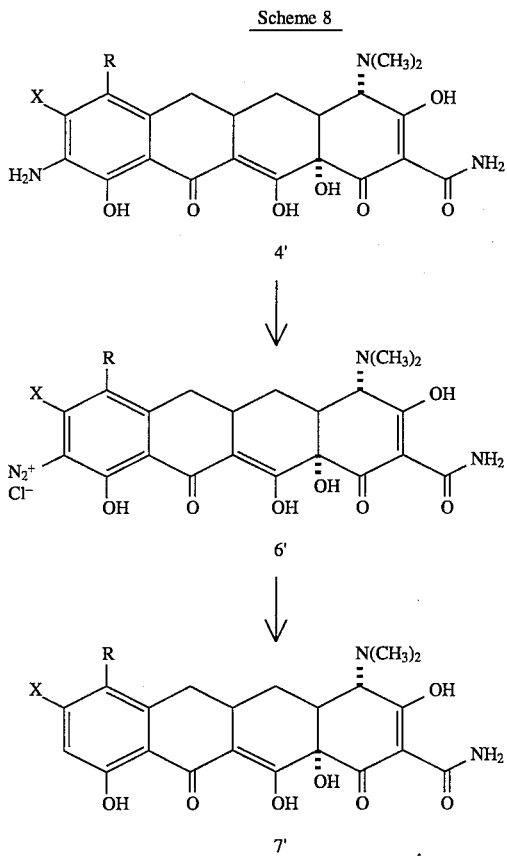

In accordance with Scheme 7 or 8, a 7-amino- 8-(substituted)-9-(substituted)-6-demethyl-6-deoxytetracycline, 4, or 9-amino-8-(substituted)-7-(substituted)- 6-demethyl-6-deoxytetracycline, 4', or their mineral acid or halide salt, is converted to the respective diazonium salt, 6 or 6', using procedures known to those skilled in the art including those described in J. J. Hlavka, et al., J. Am. Chem. Soc., 84, 1420(1962).

The diazonium salts, 6 or 6', are reduced to their respective 8-(substituted)-7-(substituted)-6-demethyl- 6-deoxytetracycline, 7, or 8-(substituted)-9-(substituted)- 6-demethyl-6-deoxytetracycline, 7', by heating in an alcohol.

Scheme 9

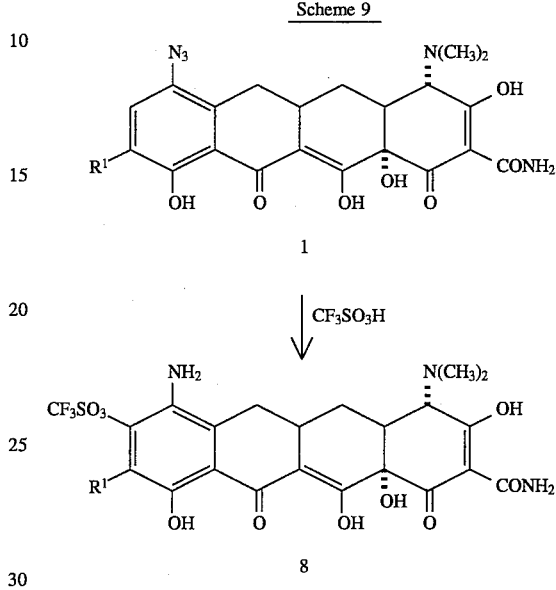

Scheme 10

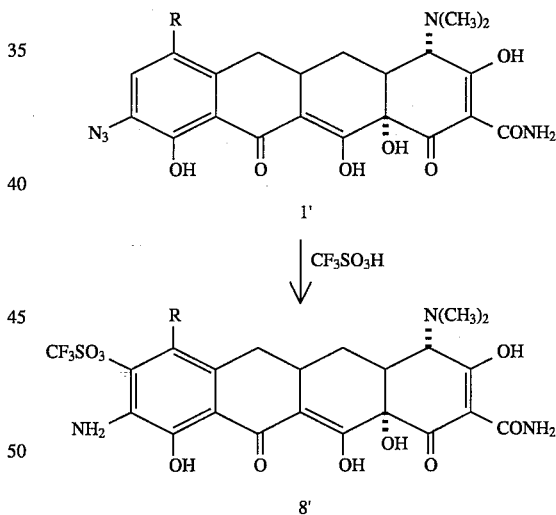

In accordance with Scheme 9 or 10, a 7-azido 9-(substituted)-6-demethyl-6-deoxytetracycline, 1, or a 9-azido-7-(substituted)-6-demethyl-6-deoxytetracycline, 1', is treated with trifluoromethanesulfonic acid to give the desired 7-amino-9-(substituted)-8-(trifluoromethanylsulfonyloxy)-6-demethyl-6-deoxytetracycline, 8, or 9-amino-7-(substituted)-8-(trifluoromethanylsulfonyloxy)-6-demethyl-6-deoxytetracycline, 8'.

Scheme 11

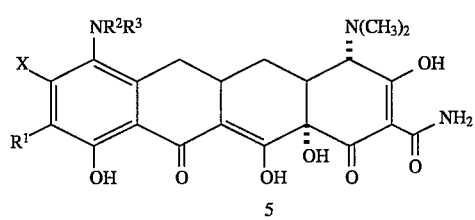

Scheme 12

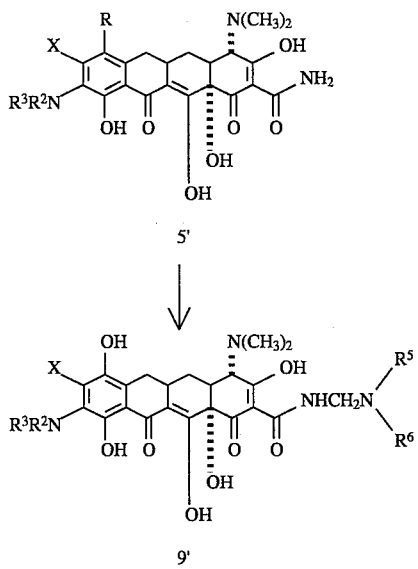

Scheme 13

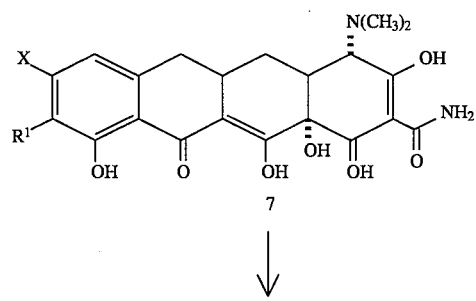

Scheme 13 -continued

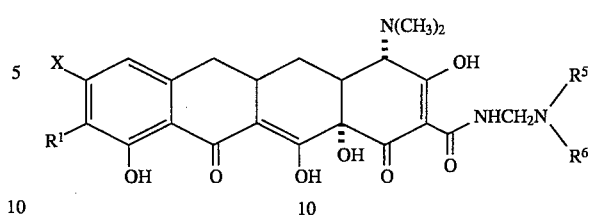

Scheme 14

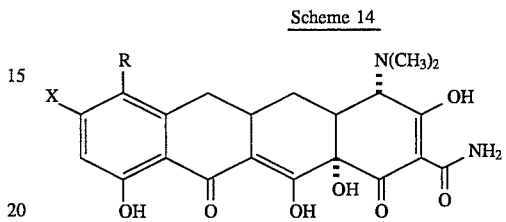

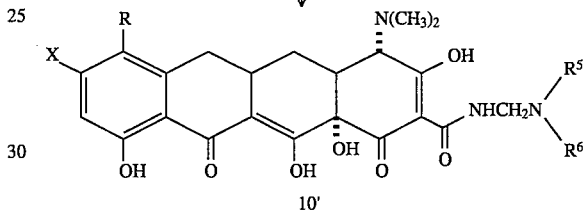

In accordance with Schemes 11–14, Compounds 5, 5', 7, or 7' are selectively N-alkylated in the presence of formaldehyde and either a primary amine such as methylamine, ethylamine, benzylamine, methyl glycinate, (L or D)lysine, (L or D)alanine or their substituted congeners; or a secondary amine such as morpholine, pyrrolidine, piperidine or their substituted congeners to give their corresponding Mannich base adduct, 9, 9', 10 or 10'.

The 7-(substituted)-8-(substituted)-9-(substituted)-6-demethyl-6-deoxytetracyclines may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). Preferably, the 7-(substituted)-8-(substituted)-9-(substituted)-6-demethyl- 6-deoxytetracyclines are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate, alkylsulfonate or arysulfonate. In all cases the salt formation occurs with the C(4)-dimethylamino group. The salts are preferred for oral and parenteral administration.

BIOLOGICAL ACTIVITY

Method for In Vitro Antibacterial Evaluation (Table I)

The minimum inhibitory concentration (MIC), the lowest concentration of the antibiotic which inhibits growth of the test organism, is determined by the agar dilution method using Muller-Hinton II agar (Baltimore Biological Laboratories). An inoculum density of $1-5\times10^5$ CFU/ml and an antibiotic concentration ($32-\leq0.015$ µg/ml) is used. The plates are incubated for 18 hours at 35° C. in a forced air incubator. The test organisms comprise strains sensitive to tetracycline and genetically defined strains that are resistant to tetracycline, due to inability to bind bacterial ribosomes (tetM).

E. coli in Vitro protein Translation System (Table II)

An in vitro, cell free, protein translation system using extracts from E. coli strain MRE 600 (tetracycline sensitive) and a derivative of MRE 600 containing the tetM determinant has been developed based on literature methods [J. M. Pratt, Coupled Transcription-translation in Prokaryotic Cell-free Systems, Transcription and Translation, a Practical Approach, (B. D. Hames and S. J. Higgins, eds) p. 179–209, IRL Press, Oxford-Washington, 1984].

Using the system described above, the tetracycline compounds of the present invention are tested for their ability to inhibit protein synthesis in vitro. Briefly, each 10 µl reaction contains S30 extract (a whole extract) made from either tetracycline sensitive cells or an isogenic tetracycline resistant (tetM) strain, low molecular weight components necessary for transcription and translation (i.e., ATP and GTP), a mix of 19 amino acids (no methionine), $^{35}S$ labeled methionine, DNA template (either pBR322 or pUC119), and either DMSO (control) or the novel tetracycline compound to be tested ("novel TC") dissolved in DMSO.

The reactions are incubated for 30 minutes at 37° C. Timing is initiated with the addition of the S30 extract, the last component to be added. After 30 minutes, 2.5 µl of the reaction is removed and mixed with 0.5 ml of 1N NaOH to destroy RNA and tRNA. Two to three ml of 25% trichloroacetic acid is added and the mixture incubated at room temperature for 15 minutes. The trichloroacetic acid precipitated material is collected on Whatman GF/C filters and washed with a solution of 10% trichloroacetic acid. The filters are dried and the retained radioactivity, representing incorporation of $^{35}S$-methionine into polypeptides, is counted using standard liquid scintillation methods.

The percent inhibition (P.I.) of protein synthesis is determined to be:

$$P.I. = 100 - \left( \frac{\text{Retained radioactivity of novel } TC \text{ containing sample}}{\text{Retained radioactivity of } DMSO \text{ control reaction}} \right) \times 100$$

In Vivo Antibacterial Evaluation (Table III)

The therapeutic effects of tetracyclines are determined against an acute lethal infection with *Staphylococcus aureus* strain Smith (tetracycline sensitive). Female, mice, strain CD-1 (Charles River Laboratories), 20±2 grams, are challenged by an intraperitoneal injection of sufficient bacteria (suspended in hog mucin) to kill non-treated controls within 24–48 hours. Antibacterial agents, contained in 0.5 ml of 0.2% aqueous agar, are administered subcutaneously or orally 30 minutes after infection. When an oral dosing schedule is used, animals are deprived of food for 5 hours before and 2 hours after infection. Five mice are treated at each dose level. The 7 day survival ratios from 3 separate tests are pooled for calculation of median effective dose ($ED_{50}$).

Testing Results

The claimed compounds exhibit antibacterial activity against a spectrum of tetracycline sensitive and resistant Gram-positive and Gram-negative bacteria, especially, strains of E. coli, S. aureus and E. faecalis, containing the tetM resistance determinants (Table I). Notable is 8-chloro-9-(formylamino)-4-(dimethylamino)- 6-demethyl-6-deoxytetracycline, compound A in Table I, which has good in vitro activity against tetracycline resistant strains containing the tetM resistance determinant (such as S. aureus UBMS 88-5 and S. aureus UBMS 90-1 and 90-2) and is equally as effective as minocycline against tetracycline susceptible strains.

Protein synthesis, determined using cell-free extracts from the tetracycline susceptible strain MRE600, is inhibited by tetracycline, minocycline and the 8-chloro-9-(formylamino)-4-(dimethylamino)-6-demethyl- 6-deoxytetracycline of this invention (Table II). Protein synthesis, determined using cell-free extracts from strain MRE600 (tetM), is resistant to tetracycline and minocycline, since less than 20% inhibition is achieved even at 1 mg/ml concentration of minocycline vs 90% inhibition at 0.3 mg/ml of the tetracycline sensitive ribosome extracts prepared from strain MRE600 (Table II). In contrast, 8-chloro-9-(formylamino)-4-(dimethylamino)-6-demethyl- 6-deoxytetracycline effectively inhibited protein synthesis in extracts prepared from either MRE600 or MRE600 (tetM) (Table II). The evidence presented indicates that 8-chloro-9-(formylamino)-4-(dimethylamino)- 6-demethyl-6-deoxytetracycline is an inhibitor of protein synthesis at the ribosome level. The ability of 8-chloro-9-(formylamino)-4-(dimethylamino)- 6-demethyl-6-deoxytetracycline to inhibit bacterial growth almost certainly reflects directed inhibition of bacterial protein synthesis. Therefore, it is expected to exhibit a bacteriostatic effect against susceptible bacteria, as is the case with other tetracyclines.

The antibacterial activity of 8-chloro- 9-(formylamino)-4-(dimethylamino)-6-demethyl-6-deoxytetracycline is also demonstrated by in vivo efficacy in animals infected with S. aureus Smith (Table III).

The improved efficacy of 8-chloro-9-(formylamino)-4-(dimethylamino)-6-demethyl-6-deoxytetracycline is demonstrated by the in vitro activity against isogenic strains into which the resistance determinants, such as tetM, were cloned (Table I); the inhibition of protein synthesis by tetM ribosomes (Table II); and the in vivo activity against experimental infections (Table III).

| LEGEND FOR COMPOUNDS | |
|---|---|
| LETTER | NAME |
| A | 8-Chloro-4-(dimethylamino)-9-(formylamino)-1,4,4a,5,5a,6,11,12a-octahydro-3,10,12,12a-tetrahydroxy-1,11-dioxo-2-naphthacenecarboxamide hydrochloride or sulfate |
| B | 8-Chloro-4,7-bis(dimethylamino)-1,4,4a,5-5a,6,11,12a-octahydro-3,10,12,12a-tetrahydroxy-1,11-dioxo-2-naphthacenecarboxamide sulfate |
| C | 7-Amino-8-chloro-4-(dimethylamino)-1,4-4a,5,5a,6,11,12a-octahydro-3,10,12,12a-tetrahydroxy-1,11-dioxo-2-naphthacenecarboxamide hydrochloride |
| D | 8-(Aminocarbonyl)-2-chloro-10-(dimethyl- |

LEGEND FOR COMPOUNDS

| LETTER | NAME |
|---|---|
| | amino)-5,6a,10,10a,11,11a,12-octahydro-5,7-dioxo-l-naphthacenediazonium chloride |
| E | 8-Chloro-4-(dimethylamino)-1,4,4a,5,5a,6-11,12a-octahydro-3,10,12,12a-tetrahydroxy-1,11-dioxo-2-naphthacenecarboxamide sulfate |
| F | 8-Chloro-4,7-bis(dimethylamino)-9-(formylamino)-1,4,4a,5,5a,6,11,12a-octahydro-3,10,12,12a-tetrahydroxy-1,11-dioxo-2-naphthacenecarboxamide sulfate |
| G | 9-Amino-8-chloro-4-(dimethylamino)-1,4,4a,5,5a,6,11,12a-octahydro-3,10,12,12a-tetrahydroxy-1,11-dioxo-2-naphthacenecarboxamide |
| H | 9-Amino-8-chloro-4,7-(dimethylamino)-1,4,4a,5,5a,6,11,12a-octahydro-3,10,12,12a-tetrahydroxy-1,11-dioxo-2-naphthacenecarboxamide sulfate |
| I | [7S-(7alpha, 10aalpha)]-[9-(Aminocarbonyl)-3-chloro-7-(dimethylamino)-5,5a,6-6a,7,10,10a,12-octahydro-1,8,10a,11-tetrahydroxy-10,12-dioxo-2-naphthacenyl]-carbamic acid methyl ester |
| J | [4S-(4alpha, 12aalpha)]-8-Chloro-4-(dimethylamino)-9-hydrazino-1,4,4a,5,5a,6-11,12a-octahydro-3,10,12,12a-tetrahydroxy-1,11-dioxo-2-naphthacenecarboxamide monohydrochloride |
| K | Tetracycline hydrochloride |
| L | Minocycline hydrochloride |
| M | [4S(4alpha, 12aalpha)]-9-Amino-8-chloro-7-(diethylamino)-4-dimethylamino)-1,4,4a,-5,5a,6,11,12a-octahydro-3,10,12,12a-tetrahydroxy-1,11-dioxo-2-naphthacenecarboxamide |

TABLE I

ANTIBACTERIAL ACTIVITY OF 8-(HALOGEN)-7-(SUBSTITUTED)-9-(SUBSTITUTED)-6-6-DEMETHYL-6-DEOXYTETRACYCLINES
MIC (µg/ml)

| Organism | Compound | | | | | |
|---|---|---|---|---|---|---|
| | A | B | C | D | E | F |
| E. coli UBMS 88-1 (tetB) | 32 | >32 | >32 | >32 | >32 | >32 |
| E. coli UBMS 88-2 (sensitive) | 0.12 | 8 | 2 | 32 | 16 | 1 |
| E. coli UBMS 89-1 (tetM) | NG | >32 | 32 | 32 | 16 | 0.5 |
| E. coli UBMS 89-2 (sensitive) | 0.25 | 16 | 4 | 32 | 16 | 1 |
| E. coli ATCC 25922 | 0.12 | 8 | 2 | 16 | 8 | 0.25 |
| S. aureus UBMS 88-4 (sensitive) | <0.015 | 0.03 | 0.5 | 0.5 | 0.25 | 0.12 |
| S. aureus UBMS 88-5 (tetM) | 0.12 | 0.5 | 32 | 4 | 2 | 0.25 |
| S. aureus UBMS 88-7 (tetK) | 16 | 0.5 | >32 | 8 | 4 | 4 |
| S. aureus UBMS 90-1 (tetM) | 0.25 | 0.05 | 32 | 4 | 2 | 0.5 |
| S. aureus UBMS 90-3 (sensitive) | <0.015 | 0.06 | 0.12 | 0.5 | 0.12 | 0.06 |
| S. aureus UBMS 90-2 (tetM) | 0.03 | 0.5 | 8 | 2 | 1 | 0.12 |
| S. aureus IVES 2943 (meth. resistant) | 32 | 1 | >32 | 16 | 4 | 8 |
| S. aureus SMITH (MP) (sensitive) | <0.015 | 0.06 | 0.25 | 0.5 | 0.12 | 0.06 |
| S. aureus IVES 1983 (MP) (meth. resistant) | 32 | 1 | >32 | 16 | 4 | 8 |
| S. aureus ATCC 29213 (sensitive) | <0.015 | ≦0.015 | 0.12 | 0.12 | 0.03 | 0.06 |
| Enteroc. spp. 12201 | 0.5 | 1 | 32 | 2 | 1 | 0.5 |
| S. faecal. ATCC 29212 | <0.015 | 1 | 8 | 2 | 2 | 0.06 |
| S. haemol. AVAH 88-3 | NT | 0.25 | 1 | 1 | 0.5 | 0.12 |

| Organism | Compound | | | | | |
|---|---|---|---|---|---|---|
| | G | H | I | J | K | L |
| E. coli UBMS 88-1 (tetB) | >32 | >32 | >32 | 32 | >32 | 16 |
| E. coli UBMS 88-2 (sensitive) | 4 | 8 | NT | 2 | 0.25 | 0.25 |
| E. coli UBMS 89-1 (tetM) | NG | NG | 8 | 16 | 16 | 8 |
| E. coli UBMS 89-2 | 4 | 16 | 16 | 4 | 1 | 1 |

TABLE I-continued

ANTIBACTERIAL ACTIVITY OF 8-(HALOGEN)-7-(SUBSTITUTED)-9-(SUBSTITUTED)-6-
6-DEMETHYL-6-DEOXYTETRACYCLINES
MIC (µg/ml)

| | | | | | | |
|---|---|---|---|---|---|---|
| (sensitive) | | | | | | |
| E. coli ATCC 25922 | 1 | 4 | 8 | 1 | 0.5 | 0.5 |
| S. aureus UBMS 88-4 (sensitive) | <0.015 | 0.12 | 0.06 | 0.06 | 0.12 | 0.03 |
| S. aureus UBMS 88-5 (tetM) | 1 | 1 | 0.5 | 0.5 | >32 | 4 |
| S. aureus UBMS 88-7 (tetK) | 2 | 0.25 | 2 | 1 | >32 | 0.12 |
| S. aureus UBMS 90-1 (tetM) | 1 | 2 | 0.5 | 0.5 | >32 | 4 |
| S. aureus UBMS 90-3 (sensitive) | <0.015 | 0.12 | 0.06 | 0.03 | 0.06 | 0.03 |
| S. aureus UBMS 90-2 (tetM) | 0.25 | 0.5 | 0.5 | 0.5 | 32 | 4 |
| S. aureus IVES 2943 (meth. resistant) | 8 | 1 | 4 | 2 | >32 | 4 |
| S. aureus SMITH (MP) (sensitive) | <0.015 | 0.06 | 0.06 | 0.03 | 0.06 | 0.03 |
| S. aureus IVES 1983 (MP) (meth. resistant) | 8 | 4 | 4 | 2 | >32 | 4 |
| S. aureus ATCC 29213 (sensitive) | <0.015 | <0.015 | <0.015 | ≦0.015 | ≦0.015 | ≦0.015 |
| Enteroc. spp. 12201 | 2 | 4 | 2 | 0.05 | 32 | 8 |
| S. faecal. ATCC 29212 | 0.25 | 0.5 | 0.5 | 0.5 | 16 | 1 |
| S. haemol. AVAH 88-3 | 0.12 | 0.12 | 0.5 | 0.25 | 1 | 0.12 |

NG = No growth
NT = Not tested

TABLE II

INHIBITION OF PROTEIN SYNTHESIS BY E. COLI
CELL-FREE RIBOSOMES WITH TETRACYCLINES

| | | % Inhibition | |
|---|---|---|---|
| Compound | Conc. | Wild Type S30 | TetM S30 |
| H | 1.0 mg/ml | 57 | 29 |
| | 0.3 mg/ml | 62 | 21 |
| | 0.1 mg/ml | 52 | 19 |
| L | 1.0 mg/ml | 90 | 19 |
| | 0.3 mg/ml | 91 | 0 |
| | 0.1 mg/ml | 66 | 0 |
| A | 1.0 ml/ml | 93 | NT |
| | 0.3 mg/ml | 98 | NT |

NT = Not Tested

TABLE III

PROTECTIVE ACTIVITY IN MICE INFECTED WITH
STAPHYLOCOCCUS AUREUS SMITH

| Compound | $ED_{50}$ (mg/kg) |
|---|---|
| H | 4–8 |
| B | >16 |
| M | >16 |
| A HCL | 4–8 |
| A $H_2SO_4$ | 4–8 |
| J | >16 |

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and fluid. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

EXAMPLE 1

[7S-(7Alpha, 10Alpha)]-9-(Aminocarbonyl)-4,7-Bis-(Dimethylamino)- 5,5a,6,6a,7,10,10a,12-Octahydro-1,8, 10a, 11-Tetrahydroxy-10,12-Dioxo-2-Naphthacenediazonium Chloride Sulfate (1:1)

To a 0° C. solution of 3.0 g of 9-amino-4,7-bis(dimethylamino)-1,4,4a,5,5a,6,11,12-octahydro-3,- 10,12,12a-tetrahydroxy-1,11-dioxo-2-naphthacenecarboxamide sulfate dissolved in 100 ml of 0.1N methanolic hydrogen chloride is added, dropwise, 6.6 ml of butyl nitrite. The reaction is stirred at 0° C. for 1 hour, poured into 400 ml of diethyl ether, collected and dried to give 2.64 g of the desired product.

MS(FAB): m/z 484 (M+H)

EXAMPLE 2

[4S-4Alpha, 12aAlpha)]-9-Azido-4,7-Bis(Dimethylamino)-1,4,4a,5,5a,6,11,12-Octahydro-3,10,12,12a-Tetrahydroxy-1,11,Dioxo-2-Naphthacenecarboxamide Hydrochloride (1:1)

To a room temperature solution of 2.64 g of product from Example 1 dissolved in 84 ml of 0.1N methanolic hydrogen chloride is added 0.353 g of sodium azide. The mixture is stirred at room temperature for 4 hours, poured into 500 ml of diethyl ether and collected to give 2.5 g of the desired product.

IR(KBr): 2080 $cm^{-1}$.

EXAMPLE 3

[4S-(4α,12aα)]-9-Amino-8-Chloro-4,7-Bis(Dimethylamino)-1,4,4a,5,5a,6, 11,12a-Octahydro-3,10,12,12a-Tetrahydroxy-1,11-Dioxo-2 Naphthacenecarboxamide Sulfate One gram of product from Example 2 is added to 10 ml of 0° C. concentrated sulfuric acid. The reaction is stirred at 0° C. for 1.5 hours, poured into 500 ml of diethyl ether, collected and dried to give 1.1 g of the desired product.

MS(FAB): m/z 507 (M+H).

EXAMPLE 4

[4S-(4α,12aα)]- 8-Chloro-4,7-Bis(Dimethyamino)-9-(Formylamino)-1,4,4a,5,5a,6,11,12a-Octahydro-3,10,12, 12a-Tetrahydroxy-1,11,Dioxo-2-Naphthacenecarboxamide Sulfate (1:1)

To a 0° C. solution of 0.092 g of product from Example 3 dissolved in 5.0 ml of 98% formic acid is added 0.0164 g of sodium acetate. The resulting mixture is stirred at 0° C. for 10 minutes, followed by the addition of 0.23 ml of acetic anhydride. The reaction is stirred at room temperature of 1 hour, poured into diethyl ether and collected to give 0.045 g of solid. The collected solid is triturated with 50 ml of ethyl acetate and filtered. The filtrate is concentrated in vacuo to give 0,019 g of the desired product.

MS(FAB): m/z 535 (M+H).

EXAMPLE 5

[4S-(4α,12aα)]-8-Chloro-4,7-Bis(Dimethylamino)-1,4, 4a,5,5a,6,11,12a-Octahydro-3,10,12,12a-Tetrahydroxy-1, 11-Dioxo-2-Naphthacenecarboxamide Sulfate (1:1)

To a 0° C. solution of 0.090 g of product from Example 3 dissolved in 35 ml of 0.1N methanolic hydrogen chloride is added 0.2 ml of butyl nitrite. The reaction is stirred at room temperature for 1 hour, poured into 70 ml of diethyl ether and collected give 0.070 g of the desired diazonium chloride intermediate.

A solution of 0.070 g of the above intermediate dissolved in 20 ml of methyl alcohol is heated at the reflux temperature for 45 minutes, poured into diethyl ether and collected to give 0.056 g of the desired product.

MS(FAB): m/z 491 ($M^+$).

EXAMPLE 6

[4S-(4α,12aα)- 7-Amino-8-Chloro-4-(Dimethylamino)-1,4,4a,5,5a,6,11,12 a-Octahydro-3,10,12,12a-Tetrahydroxy-1,11-Dioxo-2-Naphthacenecarboxamide Hydrochloride (1:1)

Three grams of 7-azido-6-demethyl-6-deoxytetracycline hydrochloride, prepared by the procedure described in J. Am. Chem. Soc., 84:1426–1430, is added to 120 ml of cold concentrated hydrochloric acid and stirred for 1 ¾ hours at ice bath temperature. The reaction mixture is concentrated in vacuo to give 2.9 g of the desired product.

MS(FAB): m/z 464 (M+H).

EXAMPLE 7

[6aS-(6aα,10aα)]-8-(Aminocarbonyl)-2-Chloro-10-(Dimethylamino)-5,6a,10, 10a,11,11a,12-Octahydro-5,7-Dioxo-1-Naphtha Cenediazonium Chloride Hydrochloride To a 0° C. solution of 0.50 g of product from Example 6 dissolved in 15 ml of 0.1N methanolic hydrogen chloride is added 1.0 ml of butyl nitrite. The reaction is stirred at 0° C. for 1 hour, poured into 500 ml of diethyl ether and collected to give 0.48 g of the desired product.

IR(KBr): 2200 $cm^{-1}$.

EXAMPLE 8

[4S-(4Alpha, 12aAlpha)]-7-Azido-8-Chloro-4-(Dimethylamino)-1,4,4a,5,5a,6,11,12a-Octahydro-3,10,12,12a Tetrahydroxy-1,11-Dioxo-2-Naphthacenecarboxamide Hydrochloride To a room temperature solution of 0.48 g of product from Example 7 dissolved in 20 ml of 0.1N methanolic hydrogen chloride is added 0.055 g of sodium azide. The reaction mixture is stirred at room temperature for 4 hours, poured into 100 ml of diethyl ether and collected to give 0.366 g of the desired product.

MS(FAB): m/z 490 (M+H)

EXAMPLE 9

[4S-(4α, 12aα)]- 8-Chloro-4-(Dimethylamino)-1,4,4a,5,5a,6,11,12a-Octahydro-3,10,12,12a-Tetrahydroxy-1,11-Dioxo-2-Naphthacenecarboxamide Hydrochloride (1:1)

To a 0° C. solution of 0.095 g of product from Example 6 dissolved in 5 ml of 0.1N methanolic hydrogen chloride is added 0.3 ml of butyl nitrite. The reaction mixture is stirred at 0° C. for 1 hour, poured into diethyl ether and collected to give 0.070 g of the desired intermediate.

A solution of 0.050 g of the above intermediate dissolved in 15 ml of methyl alcohol is heated at the reflux temperature for 1 hour and concentrated in vacuo to give 0.035 g of the desired product.

MS(FAB): m/z 449 (M+H).

EXAMPLE 10

[4S-(4α,12aα)]- 9-Amino-8-Chloro-4-(Dimethylamino)-1,4,4a,5,5a,6,11, 12a-Octahydro-3,10,12,12a-Tetrahydroxy-1,11-Dioxo-2-Naphthacenecarboxamide Hydrochloride (1:1)

To 10 ml of concentrated hydrochloric acid at 0° C. is added 0.20 g of 9-azido-6-demethyl-6-deoxytetracycline hydrochloride prepared by the procedure described in J. Am. Chem. Soc., 84: 1426–1430. The reaction is stirred at 0° C. for 1½ hours and concentrated in vacuo to give 0.195 g of the desired product.

MS(FAB): m/z 464 (M+H).

EXAMPLE 11

[4S-(4α,12aα)]- 8-Chloro-4-(Dimethylamino)-9-(Formylamino-1,4,4a,5,5a, 6,11,12a-Octahydro-3,10,12,12a-Tetrahydroxy-1,11-Dioxo- 2-Naphthacenecarboxamide Hydrochloride (1:1)

To a 0° C. solution of 0.103 g of product from Example 10, as the hydrochloride, dissolved in 6 ml of formic acid is added 0.23 ml of acetic anhydride. The resulting mixture is stirred 0° C. for 5 minutes followed by 1 hour at room temperature. The reaction is poured into 500 ml of diethyl ether and collected to give 0.090 g of the desired product.

MS(FAB): m/z 492 (M+H).

EXAMPLE 12

[4S-4α,12aα)]- 7-Amino-4-(Dimethylamino)-1,4,4a,5,5a,6,11,12a-Octahydro-3,10,12,12a-Tetrahydroxy-9-Iodo-1, 11-Dioxo- 2-Naphthacenecarboxamide sulfate (1:1)

To a 0° C. solution of 0.285 g of 7-amino-6-demethyl-6-deoxytetracycline dissolved in 5 ml of concentrated sulfuric acid is added 1.2 equivalents of N-iodosuccinimide. The reaction is stirred at 0° C. for 15 minutes then poured into 400 ml of diethyl ether. The resulting solid is collected and dried to give 0.23 g of the desired product.

$^1$H NMR(DMSO-d$_6$): 68.0 (C-8 H).

EXAMPLE 13

[6aS-(6aAlpha,10aAlpha)]-8-(Aminocarbonyl)-10-(Dimethylamino)-5,6a,7,10,10a,11,11a,12-Octahydro-4,6,6a,9-Tetrahydroxy-3-Iodo-5,7-Dioxo-1-Naphthacenediazonium Chloride Sulfate (1:1;1)

To a 0° C. solution of 0.15 g of product from Example 12 dissolved in sufficient 0.1N methanolic hydrogen chloride to affect solution is added, dropwise, 0.143 ml of n-butyl nitrite. The reaction is stirred at 0° C. for 30–45 minutes then poured into cold, stirring diethyl ether. The resulting solid is collected, washed with diethyl ether and dried to give 0.12 g of the desired product.

$^1$H NMR(DMSO-d$_6$): 68.52 (C-8 H).

EXAMPLE 14

[4S-(4Alpha,12aAlpha)]-7-Azido-4-(Dimethylamino)-1,4,4a,5,5a,6,11,12a-Octahydro-3,10,12,12a-Tetrahydroxy-9-Iodo-1,11-Dioxo-2-Naphthacenecarboxamide Sulfate (1:1)

The title compound is prepared by the procedure of Example 8, using 2.2 g of product from Example 13, 60 ml of 0.1N methanolic hydrogen chloride and 0.203 g of sodium azide to give (after purification) 0.65 g of the desired product.

IR(KBr): 2100 cm$^{-1}$.

MS(FAB): m/z 582 (M+H).

EXAMPLE 15

[4S-4Alpha,12aAlpha)]-7-Amino-8-Chloro-4-(Dimethylamino)-1,4,4a,5,5a,6,11,12a-Octahydro,3,10,12 12a-Tetrahydroxy-9-Iodo-1,11-Dioxo-2-Naphthacenecarboxamide Sulfate (1:1)

A mixture of 0.2 g of product from Example 14 and 1 ml of concentrated hydrochloric acid is stirred at room temperature for 2 hours. The reaction mixture is triturated with iso-propanol and ether, collected and dried to give 0.18 g of the desired product.

MS(FAB): m/z 590 (M+H).

EXAMPLE 16

[7S-(7Alpha, 10aAlpha)]-9-(Aminocarbonyl)-4-(Diethyamino)-7-Dimethylamino)-5,5a,6,6a,7,10,10a,12-Octahydro-1,8,10a,11-Tetrahydroxy-10,12Dioxo- 2-Naphthacenediazonium Chloride Sulfate (2:1)

To a 0° C. solution of 1.85 g 9-amino-7-(diethylamino)-6-demethyl-6-deoxytetracycline, prepared by the procedure described in U.S. patent application Ser. No. 07/771,697, filed Oct. 4, 1991 dissolved in 40 ml of 0.1N methanolic hydrogen chloride is added 1.85 ml of n-butyl nitrite. The reaction mixture is stirred at 0° C. for 2 hours, poured into diethyl ether, the solid is collected and washed with diethyl ether to give 2.1 g of the desired product.

$^1$H NMR(DMSO-d$_6$): ε7.9 (C-8 H).

EXAMPLE 17

[4S-4Alpha, 12aAlpha)]-9-Azido-7-(Diethylamino)-4-(Dimethylamino)-1,4,4a,5,5a,6,11,12a-Octahydro-3,10, 12,12a-Tetrahydroxy-1,11-Dioxo-2-Naphthacenecarboxamide Disulfate To a room temperature solution of 1.192 g of product from Example 16 dissolved in 75 ml of 0.1N methanolic hydrogen chloride is added 0.104 g of sodium azide. The reaction is stirred at room temperature for 2 hours, poured slowly into diethyl ether and collected to give 0.8 g of the desired product.

$^1$H NMR(DMSO-d$_6$): ε7.5 (C-8 H).

EXAMPLE 18

[4S-(4Alpha, 12aAlpha)]-9-Azido-7-(Diethylamino)-4-(Dimethylamino)-1,4,4a,5,5a,6,11,12a-Octahydro-3,10, 12,12a-Tetrahydroxy-1,11-Dioxo-2-Naphthacenecarboxamide Dihydrochloride To a room temperature solution of 0.6 g of product from Example 17 dissolved in water is added solid sodium acetate to achieve pH 5. The mixture is extracted 2 times with chloroform, the organic layer is dried over sodium sulfate and concentrated in vacuo. The residue is redissolved in 5 ml of methanol and 2 drops of concentrated hydrochloric acid is added. The reaction solution is then added dropwise to 120 ml of diethyl ether. The resulting solid is collected to give 0.4 g of the desired product.

IR(KBr): 2100 cm$^{-1}$.

EXAMPLE 19

[4S-(4Alpha, 12aAlpha)]-9-Amino-8-Chloro-7-(Diethylamino)-4-(Dimethylamino)-1,4,4a,5,5a,6,11,12a-Octahydro- 3,10,12,12a-Tetrahydroxy-1,11-Dioxo-2-Naphthacenecarboxamide Sulfate A mixture of 0.23 g of product from Example 18 and 5 ml of concentrated hydrochloric acid is stirred at room temperature for 2 hours. The resulting solid is triturated with isopropanol and diethyl ether. The solid is collected, washed with diethyl ether and dried to give 0.21 g of the desired product.

MS(FAB): m/z 535 (M+H).

EXAMPLE 20

[7S-(7Alpha, 10aAlpha)]-[9-(Aminocarbonyl)-3-Chloro-7-(Dimethylamino)-5,5a,6,6a,7,10,10a,12-Octahydro-1,8,-10a,11-Tetrahydroxy-10,12-Dioxo-2-Naphthacenyl]Carbamic Acid Methyl Ester To a room temperature solution of 0.20 g of product from Example 10, dissolved in 4 ml of 1-methyl- 2-pyrrolidinone, is added 0.30 g of sodium bicarbonate. The mixture is stirred for 5 minutes followed by the addition of 34 μl of methyl chloroformate. The reaction is stirred at room temperature for 1 hour, filtered into 200 ml of diethyl ether and collected to give 0.066 g of the desired product.

MS(FAB): m/z 522 (M+H).

EXAMPLE 21

[4S-(4Alpha, 12aAlpha)]-8-Chloro-4-(Dimethylamino)-9-Hydrazino-1,4,4a,5,5a,6,11,12a-Octahydro-3,10,12, 12a-Tetrahydroxy-1,11-Dioxo-2-Naphthacenecarboxamide Monohydrochloride To 0.30 g of product from Example 10, dissolved in 8 ml of 0.10N methanolic hydrogen chloride, is added 0.60 ml of n-butyl nitrite. The reaction is stirred at ice bath temperature for 1 hour, poured into 200 ml of diethyl ether and collected to give 0.260 g. Fifty milligrams of the collected material is added to 3 ml of 6% sulfurous acid, stirred at room temperature for 1 hour and concentrated in vacuo to give 0.037 g of the desired product.

CI-MS: m/z 479 (M+H).

EXAMPLE 22

4S-(4Alpha, 12aAlpha)]-9-Amino-4,7-Bis(Dimethylamino)-8-Fluoro-1,4,4a,5,5a,6,11,12a-Octahydro-3,10,12, 12a-Tetrahydroxy-1,11-Dioxo-2-Naphthacenecarboxamide Hydrochloride The title compound is prepared by the procedure of Example 3, using the product from Example 2 and liquid hydrogen fluoride.

EXAMPLE 23

[6aS-(6aAlpha, 10Alpha)]-3-Amino-8-(Aminocarbonyl)-10-(Dimethylamino)-5,6a,7,10,10a,11,11a,12-Octahydro-4,6 6a,9-Tetrahydroxy-5,7-Dioxo-2-Naphthacenyl Ester Trifluoromethanesulfonic Acid The title compound is prepared by the procedure of Example 3, using 9-azido-6-demethyl-6-deoxytetracycline prepared by the procedure described in J. Am. Chem. Soc., 84:1426–1430 and trifluoromethanesulfonic acid.

EXAMPLE 24

[4S-(4Alpha, 12aAlpha)]-9-Amino-4-(Dimethyamino)-8-Fluoro-1,4,4a,5,5a,6,11,12a-Octahydro-3,10,12,12a-Tetrahydroxy- 1,11-Dioxo-2-naphthacenecarboxamide Hydrochloride The title compound is prepared by the procedure of Example 22, using 9-azido-6-demethyl-6-deoxytetracycline prepared by the procedure described in the above reference.

EXAMPLE 25

[4S-(4Alpha, 12aAlpha)]-4-(Dimethylamino)-8-Fluoro-9-(Formylamino)-1,4,4a,5,5a,6,11,12a-Octahydro-3,10,12-12a-Tetrahydroxy-1,11-Dioxo-2-Naphthacenecarboxamide Hydrochloride The title compound is prepared by the procedure of Example 4, using the product from Example 24.

EXAMPLE 26

[4S-(4Alpha, 12aAlpha)]-4-(Dimethylamino)-8-Fluoro-1,4,4a,5,5a,6,11,12a-Octahydro-3,10,12,12a-Tetra Hydroxy-1,11-Dioxo-2-Naphthacenecarboxamide Hydrochloride The title compound is prepared by the procedures described in Examples 1 and 5, using the product from Example 24.

EXAMPLE 27

[4S-(4Alpha, 12Alpha)]-4,7-Bis(Dimethylamino)-8-Fluoro-1,4,4a,5,5a,6,11,12a-Octahydro-3,10,12,12a-Tetrahydroxy- 1,11-Dioxo-2-Naphthacenecarboxamide The title compound is prepared by the procedure of Example 5, using the product of Example 22.

EXAMPLE 28

[7-(7Alpha, 10aAlpha)]-[9-(Aminocarbonyl)-7-(Dimethylamino)- 3-Fluoro-5,5a,6,6a,7,10,10a,12-Octahydro-1, 8-10a,11-Tetrahydroxy-10,12-Dioxo-2-Naphthacenyl]Carbamic Acid Methyl Ester The title compound is prepared by the procedure of Example 20, using the product from Example 24.

EXAMPLE 29

[6aS-(6aAlpha, 10aAlpha)]-3-Amino-8-(Aminocarbonyl)-1, 10-Bis(Dimethylamino)-5,6a,7,10,10a,11,11a,12-Octahydro- 4,6,6a,9-Tetrahydroxy-5,7-Dioxo-2-Naphthacenyl Ester Trifluoromethanesulfonic Acid The title compound is prepared by the procedure of Example 3, using the product from Example 3 and trifluoromethanesulfonic acid.

EXAMPLE 30

[4S-(4Alpha, 12aAlpha)]-7-Amino-4-Dimethylamino)-8-Fluoro-1,4,4a,5,5a,6,11,12a-Octahydro-3,10,12,12a-Tetrahydroxy-1,11-Dioxo-2-Naphthacenecarboxamide Hydrochloride The title compound is prepared by the procedure of Example 3, using 7-azido-6-demethyl-6-deoxytetracycline prepared by the procedure described in J. Am. Chem. Soc., 84:1426–1430 and liquid hydrogen fluoride at −30° C.

EXAMPLE 31

[7S-(7Alpha, 10aAlpha)]-[9-(Aminocarbonyl)-3-Chloro-4,7-Bis(Dimethylamino)-5,5a,6,6a,7,10,10a,12-Octahydro-1,8,10a,11-Tetrahydroxy-10,12-Dioxo-2-Naphthacen-Yl] Carbamic Acid 2-(Dimethylamino)Ethyl Ester The title compound is prepared by the procedure of Example 27, using the product from the Example 3 and beta-dimethylaminoethyl chloroformate.

EXAMPLE 32

4S-(4Alpha,12aAlpha)]-8-Chloro-9-[[[(Diethylamino)-Oxy] Carbonyl]Amino]4,7-Bis(Dimethylamino)-1,4,4a,5,-5a,6,11,12a-Octahydro-3,10,12,12a-Tetrahydroxy-1,11 Dioxo-2-Naphthacenecarboxamide The title compound is prepared by the procedure of Example 27, using the product from Example 3 and diethylaminoxy chloroformate.

EXAMPLE 33

[4S-(4Alpha,12aAlpha)]-8-Chloro-7-(Diethylamino)-4-(Dimethylamino)-9-(Formylamino)-1,4,4a,5,5a,6,11, -12a-Octahydro-3,10,12,12a-Tetrahydroxy-1,11-Dioxo-2-Naphthacenecarboxamide Sulfate The title compound is prepared by the procedure of Example 4, using the product from Example 19.

EXAMPLE 34

[6aS-(6aAlpha,10Alpha)]-[8-(Aminocarbonyl)-2-Chloro-10-(Dimethylamino)-5,6a,7,10,10a,11,11a,12-Octahydro-4, 6,6a,9-Tetrahydroxy-5,7-Dioxo-1-Naphthacenyl]-Carbamic Acid Methyl Ester The title compound is prepared by the procedure of Example 20, using the product from Example 6.

EXAMPLE 35

[4S-(4α, 12aα)]-4-(Dimethylamino)-8-Fluoro-7-(Formylamino)-1,4,4a,5,-5a,6,11,12a-Octahydro-3,10,12,12a-Tetrahydroxy-1,11-Dioxo-2-Naphthacenecarboxamide hydrochloride The title compound is prepared by the procedure of Example 4, using the product from Example 8.

EXAMPLE 36

[7-(7Alpha,10aAlpha)]-[9-Aminocarbonyl]-7-(Dimethylamino)-3-Fluoro-5,5a,6,6a,7,10,10a,12-octahydro-1,8,-10a,11-Tetrahydroxy-10,12-Dioxo-2-Naphthacenyl]-Carbamic Acid Methyl Ester The title compound is prepared by the procedure of Example 20, using the product from Example 24.

EXAMPLE 37

[7S-(7Alpha,10aAlpha)]-9-(Aminocarbonyl)-7-(Dimethylamino)-3-Fluoro-5,5a,6,6a,7,10,10a,12Octahydro-1,8,-10a,11-Tetrahydroxy-10,12-Dioxo-Carbamic Acid The title compound is prepared by the procedure of Example 33, using the product of Example 24.

EXAMPLE 38

[6-(6aAlpha,10Alpha)]-8-(Aminocarbonyl)-10-(Dimethylamino)-5,6a,7,10,10a,11,11a,12-octahydro-4,6,6a,9-Tetrahydroxy-3-[(Methoxycarbonyl)Amino]-5,7-Dioxo-2-Naphthacenyl Ester Trifluoromethanesulfonic Acid The title compound is prepared by the procedure of Example 20, using the product from Example 23.

EXAMPLE 39

[4S-(4Alpha,12aAlpha)]-8-Chloro-4-(Dimethylamino)-9-[ [[(Dimethylamino)Oxy]Carbonyl]Amino]-1,4,4a,5,5a,6, -11,12a-Octahydro-3,10,12,12a-Tetrahydroxy-1,11-Dioxo-2-Naphthacenecarboxamide The title compound is prepared by the procedure of Example 20, using the product from Example 10 and dimethylaminoxy chloroformate.

EXAMPLE 40

[4S-(4Alpha,12aAlpha)]-8-Chloro-9-[[[Diethylamino)-Oxy] Carbonyl]Amino]-4-(Dimethylamino)-1,4,4a,5,5a,6,-11,12a-Octahydro-3,10,12,12a-Tetrahydroxy-1,11-Dioxo-2-Naphthacenecarboxamide The title compound is prepared by the procedure of Example 20, using the product from Example 10 and diethylamino chloroformate.

EXAMPLE 42

[4S-(4α,12aα)]- 9-Amino-8-Bromo-4-(Dimethylamino)-1,4,4a,5,5a,6,11, 12a-Octahydro-3,10,12,12a-Tetrahydroxy-1,11-Dioxo-2-Naphthacenecarboxamide Hydrobromide (1:1)

The title compound is prepared by the procedure of Example 3, using 9-azido-6-demethyl-6-deoxytetracycline prepared by the procedure described on J. Am. Chem. Soc., 84:1426–1430 and a solution of hydrogen bromide in acetic acid (30 wt %).

EXAMPLE 42

[4S-(4α,12aα)]- 9-Amino-8-Bromo-4,7-Bis(Dimethylamino)-1,4,4a,5,5a,6, 11,12a-Octahydro-3,10,12,12a-tetrahydroxy-1,11-Dioxo-2-Naphthacenecarboxamine Hydrobromide

EXAMPLE 43

[4S-(4Alpha,12aAlpha)]-9-Amino-4,7-Bis(Dimethylamino)-8-Iodo-1,4,4a,5,5a,6,11,12a-Octahydro-3,10,12,12a-Tetrahydroxy-1,11-Dioxo-2-Naphthacenecarboxamide Hydroiodide The title compound is prepared by the procedure of Example 3, using the product from Example 2 and hydroiodic acid.

EXAMPLE 44

[4S-(4Alpha,12aAlpha)]-9-Amino-4-(Dimethylamino)-8-Iodo-1,4,4a,5,5a,11,12,12a-Octahydro-3,10,12,12a-Tetrahydroxy-1,11-Dioxo-2-Naphthacenecarboxamine Hydroiodide The title compound is prepared by the procedure of Example 3, using 9-azido-6-demethyl-6-deoxytetracycline prepared by the procedure described on J. Am. Chem. Soc., 84:1426–1430 and hydroiodic acid.

EXAMPLE 45

[7-(7Alpha,10aAlpha)]-[9-(Aminocarbonyl)-7-(Dimethylamino)-3-Iodo-5,5a,6,7,10,10a,12-Octahydro-1,8,10a,11-Tetrahydroxy-10,12-Dioxo-2-Naphthacenyl]Carbamic Acid Methyl Ester The title compound is prepared by the procedure of Example 20, using the product from Example 44.

EXAMPLE 46

[7S-(7Alpha,10aAlpha)]-[9-(Aminocarbonyl)-3-Bromo-7-(Dimethylamino)-5,5a,6,7,10,10a,12-Octahydro-1,8,10a,11-Tetrahydroxy-10,12-Dioxo-2-Naphthacenyl]Carbamic Acid Methyl Ester The title compound is prepared by the procedure of Example 20, using the product from Example 41.

We claim:

1. A method for the prevention or treatment of bacterial infections in warm-blooded animals which comprises administering to said animal a pharmacologically effective amount of a compound of the formula:

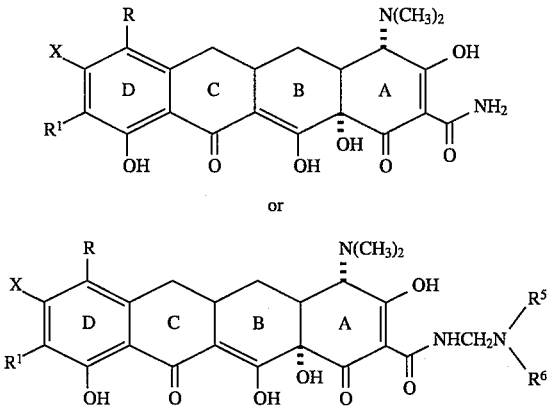

wherein:

X is selected from halogen or trifluoromethylsulfonyloxy; the halogen is selected from bromine, chlorine, or fluorine;

R and $R^1$ are the same or different and are selected from halogen selected from chlorine, bromine, fluorine or iodine; or $-NR^2R^3$;

$R^2$ is selected from hydrogen, methyl, or ethyl and $R^3$ is selected from hydrogen, methyl, ethyl, $R^4(CH_2)_nCO-$ or $R^{4'}(CH_2)_nSO_2-$, n is 0–4, with the proviso that when R or $R^1=NR^2R^3$ and $R^2=$methyl or ethyl; $R^3=$methyl or ethyl, and when R or $R^1=NR^2R^3$ and $R^2=$hydrogen, $R^3$ is selected from hydrogen, $R^4(CH_2)_nCO-$ or $R^{4'}(CH_2)_nSO_2-$; and when $R^3=R^4(CH_2)_nCO-$ and n=0, $R_4$ is selected from hydrogen; $(C_1-C_2)$alkyl group selected from methyl or ethyl; a heterocycle group selected from a five membered aromatic or saturated ring with one N, O, or S heteroatom optionally having a benzo or pyrido ring fused thereto selected from

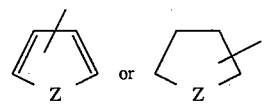

wherein Z = N, O or S wherein Z=N, O or S or a five membered aromatic ring with two N, O or S heteroatoms optionnally having a benzo or pyrido ring fused thereto selected from

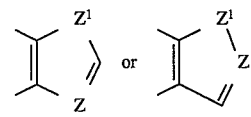

wherein Z or $Z^1$=N, O, or S; $(C_1-C_4)$alkoxygroup; $C_6$-aryloxy group selected from phenoxy or substituted phenoxy with substitution selected from halo, $(C_1-C_4)$alkyl; $(C_7-C_{10})$aralkyloxy; α-aminomethyoxycarbonyl; or halomethoxycarbonyl; and when $R^3=R^4(CH_2)_nCO-$ and n=1–4, $R^4$ is selected from hydrogen; $(C_1-C_2)$alkyl group selected from methyl or ethyl $(C_6-C_{10})$aryl group selected from phenyl, α-naphthyl or β-naphthyl; and when $R^3=R^{4'}(CH_2)_nSO_2-$ and n=0, $R^{4'}$ is selected from $(C_1-C_2)$alkyl group selected from methyl or ethyl; $(C_6-C_{10})$aryl group selected from phenyl, α-naphthyl or β-naphthyl; $R^5$ is selected from hydrogen; straight or branched $(C_1-C_3)$alkyl group selected from methyl, ethyl, n-propyl or 1-methylethyl;

$R^6$ is selected from hydrogen; straight or branched $(C_1-C_3)$alkyl group selected from methyl, ethyl, n-propyl or 1-methylethyl; with the proviso that $R^5$ and $R^6$ cannot both be hydrogen;

or $R^5$ and $R^6$ taken together are $-(CH_2)_2W(CH_2)_2-$, wherein W is selected from $(CH_2)_m$ where m=0–1, $-NH, -N(C_1-C_3)$alkyl straight or branched, $-N(C_1-C_4)$ alkoxy, oxygen, sulfur or substituted congeners selected from (L or D)proline, ethyl (L or D)prolinate, morpholine, pyrrolidine or piperidine; and the pharmacologically acceptable organic and inorganic salts or metal complexes.

* * * * *